United States Patent
Kato et al.

(10) Patent No.: US 11,981,747 B1
(45) Date of Patent: *May 14, 2024

(54) HER2 TARGETING AGENT

(71) Applicants: ONO PHARMACEUTICAL CO., LTD., Osaka (JP); TOHOKU UNIVERSITY, Miyagi (JP)

(72) Inventors: Yukinari Kato, Miyagi (JP); Mika Kaneko, Miyagi (JP); Daisuke Nakayama, Osaka (JP); Masayuki Kurogi, Osaka (JP)

(73) Assignees: ONO PHARMACEUTICAL CO., LTD., Osaka (JP); TOHOKU UNIVERSITY, Sendai (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,828

(22) Filed: Aug. 4, 2023

Related U.S. Application Data

(63) Continuation of application No. 18/038,185, filed as application No. PCT/JP2021/043538 on Nov. 29, 2021.

(30) Foreign Application Priority Data

Nov. 30, 2020 (JP) ................................. 2020-198044
Jul. 2, 2021 (JP) ................................. 2021-110912

(51) Int. Cl.
C07K 16/32 (2006.01)

(52) U.S. Cl.
CPC .......... C07K 16/32 (2013.01); *C07K 2317/34* (2013.01); *C07K 2317/622* (2013.01); *C07K 2317/92* (2013.01)

(58) Field of Classification Search
None
See application file for complete search history.

(56) References Cited

U.S. PATENT DOCUMENTS 9,243,057 B2 * 1/2016 Marks .................... C07K 16/40
2011/0135653 A1 6/2011 Lopez et al.

FOREIGN PATENT DOCUMENTS

JP 2011-121943 A 6/2011
WO WO-2019246021 A1 * 12/2019 ......... C07K 16/1225

OTHER PUBLICATIONS

Yamada, S., et al., "Establishment of H2Mab-119, an Anti-Human Epidermal Growth Factor Receptor 2 Monoclonal Antibody, Against Pancreatic Cancer", Monoclonal Antibodies in Immunodiagnosis and Immunotherapy, (2017), vol. 36, No. 6, pp. 287-290, DOI: 10.1089/mab.2017.0050.
Kato, Y., et al., "A Cancer-specific Monoclonal Antibody Recognizes the Aberrantly Glycosylated Podoplanin", Scientific Reports, (2014), vol. 4, 5924, DOI: 10.1038/srep05924, 9 pages total.
Kaneko, M., K., et al., "A cancer-specific antipodocalyxin monoclonal antibody (60-$mG_{2a}$-f) exerts antitumor effects in mouse xenograft models of pancreatic carcinoma", Biochemistry and Biophysics Reports, (Oct. 10, 2020), vol. 24, 100826, 7 pages total.
Crone, S., A., et al., "ErbB2 is essential in the prevention of dilated cardiomyopathy", Nature Medicine, (2002), vol. 8, No. 5, pp. 459-465, http://medicine.nature.com.
International Search Report (PCT/ISA/210) issued Jan. 11, 2022 from the International Searching Authority in International Application No. PCT/JP2021/043538.
Written Opinion (PCT/ISA/237) issued Jan. 11, 2022 from the International Searching Authority in International Application No. PCT/JP2021/043538.

* cited by examiner

*Primary Examiner* — Daniel E Kolker
*Assistant Examiner* — Maureen Varina Driscoll
(74) *Attorney, Agent, or Firm* — Sughrue Mion, PLLC

(57) ABSTRACT

An antibody or antigen-binding fragment thereof is disclosed. The antibody or antigen-binding fragment thereof binds to HER2 expressed on a cancer cell or a fragment of the HER2. A HER2-targeting agent containing any of the antibody or antigen-binding fragment thereof, and a pharmaceutical composition containing the HER2-targeting agent are disclosed.

2 Claims, 24 Drawing Sheets

Specification includes a Sequence Listing.

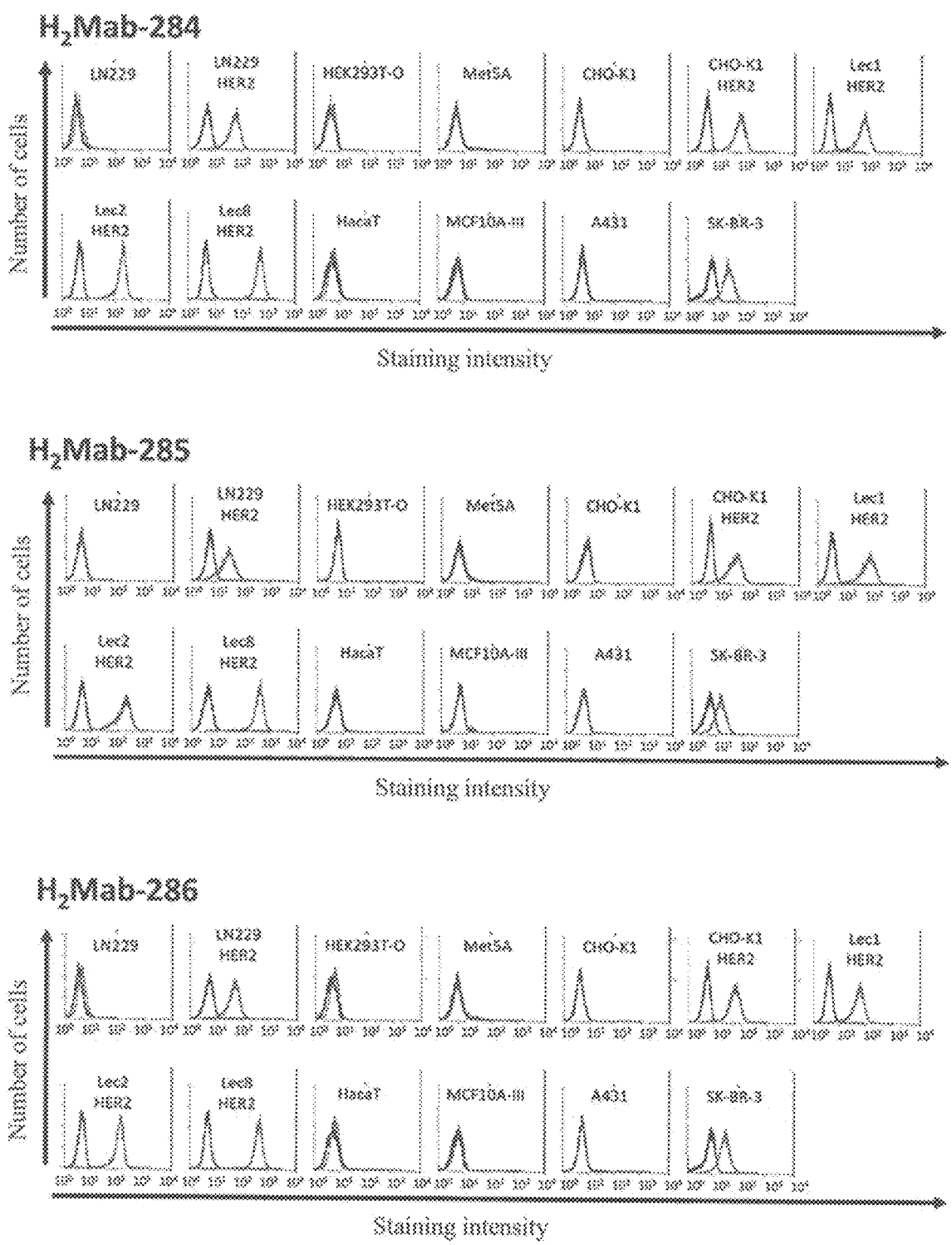

H₂Mab-282

H₂Mab-283

H₂Mab-284

H₂Mab-285

H₂Mab-286

H₂Mab-287

H₂Mab-288

H₂Mab-289

H₂Mab-290

H₂Mab-291

H₂Mab-292

H₂Mab-293

H₂Mab-294

Scale bar: 100 μm

H₂Mab-295

Scale bar: 100 μm

H₂Mab-296

Scale bar: 100 μm

H₂Mab-298

Scale bar: 100 μm

H₂Mab-299

Scale bar: 100 µm

HER2 TARGETING AGENT

CROSS-REFERENCE TO RELATED APPLICATIONS

This application is a Continuation of U.S. application Ser. No. 18/038,185 filed on May 22, 2023, which is a National Phase Entry of PCT International Application No. PCT/JP2021/043538 filed on Nov. 29, 2021, which claims priority to Japanese Patent Application No. 2020-198044 filed on Nov. 30, 2020 and Japanese Patent Application No. 2021-110912 filed on Jul. 2, 2021, the contents of all of which are incorporated herein by reference in their entirety.

TECHNICAL FIELD

The present invention relates to HER2-targeting agents.

REFERENCE TO SEQUENCE LISTING

The content of the electronically submitted sequence listing, file name: Q290224_SEQ_LIS_AS_FILED ST26.xml; size: 279,465 bytes; and date of creation: Aug. 4, 2023, is incorporated herein by reference in its entirety.

BACKGROUND ART

HER2 is a receptor tyrosine kinase, has a structure similar to that of epidermal growth factor receptor (EGFR), and is also called EGFR2, ERBB2, CD340, or NEU. The HER2 protein is also expressed on normal cells and is involved in the regulation of cell proliferation and differentiation. It is known that amplification and/or mutation of the HER2 gene makes it impossible to control the proliferation of cells, thereby causing malignant transformation of cells malignant, and HER2 is expressed on many cancers such as salivary gland cancer, stomach cancer, breast cancer, and ovarian cancer. Trastuzumab is an antibody drug that specifically binds to HER2 expressed on the surface of cancer cells. Trastuzumab can suppress signals that stimulate the proliferation of cancer cells by binding to HER2 on the cancer cells, or induce the action of immunity to destroy cancer cells.

In order to bring about such cell proliferation inhibitory action and cytotoxic action specifically in cancer cells, an antibody that specifically binds only to cancer cells is required. The CasMab method has been developed as a technique for producing an antibody specific to a cancer cell (Non Patent Literatures 1 to 3). In the CasMab method, an antibody is produced using an antigen protein expressed on LN229 cells of a glioblastoma cell line having a specific glycan profile as an immunogen.

CITATIONS LIST

Non Patent Literature

Non Patent Literature 1: Kato and Kaneko, 2014, Sci. Rep., 4: 5924
Non Patent Literature 2: Yamada et al., 2017, Monoclon. Antib. Immunodiagn. Immunother., 36(2): 72
Non Patent Literature 3: Kaneko et al., 2020, Biochem. Biophys. Rep., 24: 100826

SUMMARY OF INVENTION

The present invention provides an antibody or antigen-binding fragment thereof that binds to HER2. The present invention preferably provides an antibody or antigen-binding fragment thereof that specifically binds to HER2. The present invention provides an antibody or antigen-binding fragment thereof that has a binding affinity to HER2 expressed on cancer cells. The present invention more preferably provides an antibody or antigen-binding fragment thereof that can have a stronger binding affinity to HER2 expressed on cancer cells than to HER2 expressed on non-cancer cells. The present invention more preferably provides an antibody or antigen-binding fragment thereof that does not significantly react to HER2 expressed on non-cancer cells, but can specifically react to HER2 expressed on cancer cells. The present invention also provides a method for treating cancer in a patient using the antibody or antigen-binding fragment thereof that binds to HER2. Furthermore, the present invention provides a method for detecting HER2-positive cancer cells, the method including a patient bringing an antibody or antigen-binding fragment thereof that binds to HER2 into contact with a cancer sample obtained from the patient. The present invention also provides a method for determining whether a patient is responsive to a HER2-targeting therapy using the antibody or antigen-binding fragment thereof that binds to HER2.

The present inventors have created an antibody that specifically recognizes HER2 expressed on cancer cells. The present inventors have also found that HER2 expressed on normal cells and HER2 expressed on cancer cells can be distinguished by an antibody, and have created an antibody capable of distinguishing them. The present invention is based on such findings.

According to the present invention, the following embodiments are provided.

[0] An isolated antibody or antigen-binding fragment thereof that has a binding reactivity to HER2 expressed on a cancer cell.

[1] An isolated antibody or antigen-binding fragment thereof that has a stronger binding reactivity to HER2 expressed on a cancer cell than to HER2 expressed on a non-cancer cell.

[2] The antibody or antigen-binding fragment thereof according to [0] or [1] above that (i) binds to a peptide comprising any amino acid sequence selected from the group consisting of the amino acid sequences of SEQ ID NOs: 31 to 37 (for example, the amino acid sequences of SEQ ID NOs: 31 to 36).

[3] The antibody or antigen-binding fragment thereof according to [0], [1], or [2] above that (ii) has a stronger binding affinity (or reactivity) to a peptide consisting of an extracellular domain of HER2 set forth in SEQ ID NO: 3 than to a variant of an extracellular domain of HER2 having one or more amino acid mutations selected from the group consisting of W614A, K615A, and F616A in a peptide consisting of a part (a region of amino acid numbers 603 to 622) of the extracellular domain of HER2 set forth in SEQ ID NO: 2, for example, a stronger reactivity to the peptide consisting of the extracellular domain of HER2 set forth in SEQ ID NO: 3 than to a peptide having a point mutation of W614A or a peptide having a point mutation of K615A or F616A in the peptide consisting of the part (the region of amino acid numbers 603 to 622) of the extracellular domain of HER2 set forth in SEQ ID NO: 2 {in the above, the part of the extracellular domain of HER2 may be a region of amino acid numbers 613 to 622 of the amino acid sequence set forth in SEQ ID NO: 2}.

[4] The antibody or antigen-binding fragment thereof according to any one of [0] and [1] to [3] including:
(iii) a heavy chain variable region including:
a heavy chain CDR1 comprising the amino acid sequence of SEQ ID NO: 18;
a heavy chain CDR2 comprising the amino acid sequence of SEQ ID NO: 19; and
a heavy chain CDR3 comprising the amino acid sequence of SEQ ID NO: 20; as well as
a light chain variable region including:
a light chain CDR1 comprising the amino acid sequence of SEQ ID NO: 21;
a light chain CDR2 comprising the amino acid sequence of SEQ ID NO: 22; and
a light chain CDR3 comprising the amino acid sequence of SEQ ID NO: 23;
(iv) a heavy chain variable region including:
a heavy chain CDR1 comprising the amino acid sequence of SEQ ID NO: 24;
a heavy chain CDR2 comprising the amino acid sequence of SEQ ID NO: 25; and
a heavy chain CDR3 comprising the amino acid sequence of SEQ ID NO: 26; as well as
a light chain variable region including:
a light chain CDR1 comprising the amino acid sequence of SEQ ID NO: 27;
a light chain CDR2 comprising the amino acid sequence of SEQ ID NO: 28; and
a light chain CDR3 comprising the amino acid sequence of SEQ ID NO: 29; or
(iii) or (iv) above in which one or more of the CDRs have at least one substitution, addition, or deletion.
[5] The antibody or antigen-binding fragment thereof according to any one of [0] and [1] to [4], including:
(vii) a heavy chain variable region comprising the amino acid sequence of SEQ ID NO: 14, and
a light chain variable region comprising the amino acid sequence of SEQ ID NO: 15;
(viii) a heavy chain variable region comprising the amino acid sequence of SEQ ID NO: 16, and
a light chain variable region comprising the amino acid sequence of SEQ ID NO: 17; or
(vii) or (viii) above in which each variable region has at least one substitution, addition, or deletion.
[6] The antibody or antigen-binding fragment thereof according to any one of [0] and [1] to [5] above, binding to a peptide that is produced by LN229 cells of a glioblastoma cell line and consists of the extracellular domain of HER2 set forth in SEQ ID NO: 3
[7] The antibody or antigen-binding fragment thereof according to any one of [0] and [1] to [6] above, wherein the cancer cell is an SK-BR-3 cell of a breast cancer cell line, and the non-cancer cell is an HaCaT cell of a normal human epidermal keratinocyte cell line.
[8] A pharmaceutical composition containing, as an active ingredient, an HER2-targeting agent containing the antibody or antigen-binding fragment thereof according to any one of [0] and [1] to [7] above.
[9] The antibody or antigen-binding fragment thereof according to any one of [0] and [1] to [7] above, conjugated with a cytotoxic agent.
[10] A pharmaceutical composition containing, as an active ingredient, the antibody or antigen-binding fragment thereof according to [9] above.
[11] The pharmaceutical composition according to [8] or [10] above, for use in treating cancer.
[12] A cancer treating agent containing, as an active ingredient, the antibody or antigen-binding fragment thereof according to any one of [0] and [1] to [7] above.
[13] A nucleic acid molecule encoding the antibody or antigen-binding fragment thereof according to any one of [2] to [6] above.
[14] An antibody or antigen-binding fragment thereof, specifically binding to an epitope of an extracellular domain of HER2, including:
(iii) a heavy chain variable region including:
a heavy chain CDR1 comprising the amino acid sequence of SEQ ID NO: 18;
a heavy chain CDR2 comprising the amino acid sequence of SEQ ID NO: 19; and
a heavy chain CDR3 comprising the amino acid sequence of SEQ ID NO: 20, as well as
a light chain variable region including:
a light chain CDR1 comprising the amino acid sequence of SEQ ID NO: 21;
a light chain CDR2 comprising the amino acid sequence of SEQ ID NO: 22; and
a light chain CDR3 comprising the amino acid sequence of SEQ ID NO: 23;
(iv) a heavy chain variable region including:
a heavy chain CDR1 comprising the amino acid sequence of SEQ ID NO: 24;
a heavy chain CDR2 comprising the amino acid sequence of SEQ ID NO: 25; and
a heavy chain CDR3 comprising the amino acid sequence of SEQ ID NO: 26, as well as
a light chain variable region including:
a light chain CDR1 comprising the amino acid sequence of SEQ ID NO: 27;
a light chain CDR2 comprising the amino acid sequence of SEQ ID NO: 28; and
a light chain CDR3 comprising the amino acid sequence of SEQ ID NO: 29; or
(iii) or (iv) above in which one or more of the CDRs have at least one substitution, addition, or deletion.
[15] An antibody or antigen-binding fragment thereof that does not significantly react to HER2 expressed on a non-cancer cell, but can specifically react to HER2 expressed on a cancer cell.
[16] A method for producing, selecting or identifying an antibody or an antigen-binding fragment of an antibody, the method including:
producing, selecting or identifying an antibody or an antigen-binding fragment of an antibody that does not significantly react to HER2 expressed on a non-cancer cell, but can specifically react to HER2 expressed on a cancer cell, from a group of antibodies or antigen-binding fragments of antibodies that bind to HER2 or a fragment thereof.
[17] A method for producing, selecting or identifying an antibody or an antigen-binding fragment of an antibody, the method including:
producing, selecting or identifying an antibody or an antigen-binding fragment of an antibody that satisfies at least one selected from the group consisting of (i) to (iii) below, from a group of antibodies or antigen-binding fragments of antibodies that bind to HER2 or a fragment thereof:
(i) binding to a peptide that includes any amino acid sequence selected from the group consisting of the amino acid sequences of SEQ ID NOs: 31 to 37 (for example, the amino acid sequences of SEQ ID NOs: 31 to 36).

(ii) having a stronger binding affinity (or reactivity) to a peptide consisting of an extracellular domain of HER2 set forth in SEQ ID NO: 3 than to a variant of an extracellular domain of HER2 having one or more amino acid mutations selected from the group consisting of W614A, K615A, and F616A in a peptide consisting of a part (a region of amino acid numbers 603 to 622) of the extracellular domain of HER2 set forth in SEQ ID NO: 2, for example, having a stronger reactivity to the peptide consisting of the extracellular domain of HER2 set forth in SEQ ID NO: 3 than to a peptide having a point mutation of W614A or a peptide having a point mutation of K615A or F616A in the peptide consisting of the part of the extracellular domain of HER2 set forth in SEQ ID NO: 2 (the region of amino acid numbers 603 to 622); and (iii) having a stronger binding reactivity to HER2 expressed on a cancer cell than to HER2 expressed on a non-cancer cell.

[18] A method for producing, selecting or identifying an antibody or an antigen-binding fragment of an antibody, the method including:

producing, selecting or identifying an antibody or antigen-binding fragment thereof that binds to HER2 or a fragment thereof, from a group of antibodies or antigen-binding fragments thereof of antibodies that satisfy at least one selected from the group consisting of (i) to (ii) below:

(i) binding to a peptide that includes any amino acid sequence selected from the group consisting of the amino acid sequences of SEQ ID NOs: 31 to 37 (for example, the amino acid sequences of SEQ ID NOs: 31 to 36); and (ii) having a stronger reactivity to a peptide consisting of an extracellular domain of HER2 set forth in SEQ ID NO: 3 than to a peptide having one or more amino acid mutations selected from the group consisting of W614A, K615A, and F616A in a peptide consisting of a part (a region of amino acid numbers 603 to 622) of an extracellular domain of HER2 set forth in SEQ ID NO: 2.

[19] The method according to [17] or [18] above, further including producing, selecting or identifying an antibody or an antigen-binding fragment of an antibody that does not significantly react to HER2 expressed on a non-cancer cell, but can specifically react to HER2 expressed on a cancer cell, from a group of obtained antibodies or a group of antigen-binding fragments of the obtained antibodies.

[20] A method for producing, selecting or identifying an antibody or an antigen-binding fragment of an antibody, the method including:

producing, selecting or identifying an antibody or an antigen-binding fragment of an antibody that does not significantly react to HER2 expressed on a non-cancer cell, but can specifically react to HER2 expressed on a cancer cell, from a group of antibodies or antigen-binding fragments of antibodies that have at least one or more (for example, one to ten, for example, one, two, three, four, five, or six) amino acid mutations selected from the group consisting of substitutions, additions, insertions, and deletions in at least one CDR of any of (iii), (iv), and (xii).

[20-1] The method according to any one of [16] to [19] above, the method including causing an antibody producing cell (for example, a CHO cell) to produce the selected or identified antibody or the selected or identified antigen-binding fragment of the antibody.

[21] An antibody obtained by the method according to [20] above.

[22] The method according to any one of [16] to [20] above, wherein the antibody is a monoclonal antibody (for example, an isolated monoclonal antibody).

[23] A pharmaceutical composition containing an HER2-targeting agent that contains the antibody or antigen-binding fragment thereof according to any one of [1] to [7] above.

[24] A pharmaceutical composition containing the antibody or antigen-binding fragment thereof according to [9] above.

[25] The pharmaceutical composition according to [23] or [24] above, for use in treating cancer.

[101] (xi) The antibody or antigen-binding fragment thereof according to [0] or [1] above that binds to a peptide including the amino acid sequence of SEQ ID NO: 37.

[102] (xii) The antibody or antigen-binding fragment thereof according to any one of [0], [1] to [3], and [101] above, including:

a heavy chain variable region including
a heavy chain CDR1 comprising the amino acid sequence according to SEQ ID NO: 81,
a heavy chain CDR2 comprising the amino acid sequence according to SEQ ID NO: 82, and
a heavy chain CDR3 comprising the amino acid sequence according to SEQ ID NO: 83, as well as
a light chain variable region including
a light chain CDR1 comprising the amino acid sequence according to SEQ ID NO: 84,
a light chain CDR2 comprising the amino acid sequence according to SEQ ID NO: 85, and
a light chain CDR3 comprising the amino acid sequence according to SEQ ID NO: 86;
a heavy chain variable region including
a heavy chain CDR1 comprising the amino acid sequence according to SEQ ID NO: 87,
a heavy chain CDR2 comprising the amino acid sequence according to SEQ ID NO: 88, and
a heavy chain CDR3 comprising the amino acid sequence according to SEQ ID NO: 89, as well as
a light chain variable region including
a light chain CDR1 comprising the amino acid sequence according to SEQ ID NO: 90,
a light chain CDR2 comprising the amino acid sequence according to SEQ ID NO: 91, and
a light chain CDR3 comprising the amino acid sequence according to SEQ ID NO: 92;
a heavy chain variable region including
a heavy chain CDR1 comprising the amino acid sequence according to SEQ ID NO: 93,
a heavy chain CDR2 comprising the amino acid sequence according to SEQ ID NO: 94, and
a heavy chain CDR3 comprising the amino acid sequence according to SEQ ID NO: 95, as well as
a light chain variable region including
a light chain CDR1 comprising the amino acid sequence according to SEQ ID NO: 96,
a light chain CDR2 comprising the amino acid sequence according to SEQ ID NO: 97, and
a light chain CDR3 comprising the amino acid sequence according to SEQ ID NO: 98;

a heavy chain variable region including
a heavy chain CDR1 comprising the amino acid sequence according to SEQ ID NO: 99,
a heavy chain CDR2 comprising the amino acid sequence according to SEQ ID NO: 100, and
a heavy chain CDR3 comprising the amino acid sequence according to SEQ ID NO: 101, as well as
a light chain variable region including
a light chain CDR1 comprising the amino acid sequence according to SEQ ID NO: 102,
a light chain CDR2 comprising the amino acid sequence according to SEQ ID NO: 103, and
a light chain CDR3 comprising the amino acid sequence according to SEQ ID NO: 104;
a heavy chain variable region including
a heavy chain CDR1 comprising the amino acid sequence according to SEQ ID NO: 105,
a heavy chain CDR2 comprising the amino acid sequence according to SEQ ID NO: 106, and
a heavy chain CDR3 comprising the amino acid sequence according to SEQ ID NO: 107, as well as
a light chain variable region including
a light chain CDR1 comprising the amino acid sequence according to SEQ ID NO: 108,
a light chain CDR2 comprising the amino acid sequence according to SEQ ID NO: 109, and
a light chain CDR3 comprising the amino acid sequence according to SEQ ID NO: 110;
a heavy chain variable region including
a heavy chain CDR1 comprising the amino acid sequence according to SEQ ID NO: 111,
a heavy chain CDR2 comprising the amino acid sequence according to SEQ ID NO: 112, and
a heavy chain CDR3 comprising the amino acid sequence according to SEQ ID NO: 113, as well as
a light chain variable region including
a light chain CDR1 comprising the amino acid sequence according to SEQ ID NO: 114,
a light chain CDR2 comprising the amino acid sequence according to SEQ ID NO: 115, and
a light chain CDR3 comprising the amino acid sequence according to SEQ ID NO: 116;
a heavy chain variable region including
a heavy chain CDR1 comprising the amino acid sequence according to SEQ ID NO: 117,
a heavy chain CDR2 comprising the amino acid sequence according to SEQ ID NO: 118, and
a heavy chain CDR3 comprising the amino acid sequence according to SEQ ID NO: 119, as well as
a light chain variable region including
a light chain CDR1 comprising the amino acid sequence according to SEQ ID NO: 120,
a light chain CDR2 comprising the amino acid sequence according to SEQ ID NO: 121, and
a light chain CDR3 comprising the amino acid sequence according to SEQ ID NO: 122;
a heavy chain variable region including
a heavy chain CDR1 comprising the amino acid sequence according to SEQ ID NO: 123,
a heavy chain CDR2 comprising the amino acid sequence according to SEQ ID NO: 124, and
a heavy chain CDR3 comprising the amino acid sequence according to SEQ ID NO: 125, as well as
a light chain variable region including
a light chain CDR1 comprising the amino acid sequence according to SEQ ID NO: 126,
a light chain CDR2 comprising the amino acid sequence according to SEQ ID NO: 127, and
a light chain CDR3 comprising the amino acid sequence according to SEQ ID NO: 128;
a heavy chain variable region including
a heavy chain CDR1 comprising the amino acid sequence according to SEQ ID NO: 129,
a heavy chain CDR2 comprising the amino acid sequence according to SEQ ID NO: 130, and
a heavy chain CDR3 comprising the amino acid sequence according to SEQ ID NO: 131, as well as
a light chain variable region including
a light chain CDR1 comprising the amino acid sequence according to SEQ ID NO: 132,
a light chain CDR2 comprising the amino acid sequence according to SEQ ID NO: 133, and
a light chain CDR3 comprising the amino acid sequence according to SEQ ID NO: 134;
a heavy chain variable region including
a heavy chain CDR1 comprising the amino acid sequence according to SEQ ID NO: 135,
a heavy chain CDR2 comprising the amino acid sequence according to SEQ ID NO: 136, and
a heavy chain CDR3 comprising the amino acid sequence according to SEQ ID NO: 137, as well as
a light chain variable region including
a light chain CDR1 comprising the amino acid sequence according to SEQ ID NO: 138,
a light chain CDR2 comprising the amino acid sequence according to SEQ ID NO: 139, and
a light chain CDR3 comprising the amino acid sequence according to SEQ ID NO: 140;
a heavy chain variable region including
a heavy chain CDR1 comprising the amino acid sequence according to SEQ ID NO: 141,
a heavy chain CDR2 comprising the amino acid sequence according to SEQ ID NO: 142, and
a heavy chain CDR3 comprising the amino acid sequence according to SEQ ID NO: 143, as well as
a light chain variable region including
a light chain CDR1 comprising the amino acid sequence according to SEQ ID NO: 144,
a light chain CDR2 comprising the amino acid sequence according to SEQ ID NO: 145, and
a light chain CDR3 comprising the amino acid sequence according to SEQ ID NO: 146;
a heavy chain variable region including
a heavy chain CDR1 comprising the amino acid sequence according to SEQ ID NO: 147,
a heavy chain CDR2 comprising the amino acid sequence according to SEQ ID NO: 148, and
a heavy chain CDR3 comprising the amino acid sequence according to SEQ ID NO: 149, as well as
a light chain variable region including
a light chain CDR1 comprising the amino acid sequence according to SEQ ID NO: 150,
a light chain CDR2 comprising the amino acid sequence according to SEQ ID NO: 151, and
a light chain CDR3 comprising the amino acid sequence according to SEQ ID NO: 152;
a heavy chain variable region including
a heavy chain CDR1 comprising the amino acid sequence according to SEQ ID NO: 153,
a heavy chain CDR2 comprising the amino acid sequence according to SEQ ID NO: 154, and
a heavy chain CDR3 comprising the amino acid sequence according to SEQ ID NO: 155, as well as a light chain variable region including
a light chain CDR1 comprising the amino acid sequence according to SEQ ID NO: 156,
a light chain CDR2 comprising the amino acid sequence according to SEQ ID NO: 157, and
a light chain CDR3 comprising the amino acid sequence according to SEQ ID NO: 158;
a heavy chain variable region including
a heavy chain CDR1 comprising the amino acid sequence according to SEQ ID NO: 159,
a heavy chain CDR2 comprising the amino acid sequence according to SEQ ID NO: 160, and
a heavy chain CDR3 comprising the amino acid sequence according to SEQ ID NO: 161, as well as
a light chain variable region including
a light chain CDR1 comprising the amino acid sequence according to SEQ ID NO: 162,
a light chain CDR2 comprising the amino acid sequence according to SEQ ID NO: 163, and
a light chain CDR3 comprising the amino acid sequence according to SEQ ID NO: 164;
a heavy chain variable region including
a heavy chain CDR1 comprising the amino acid sequence according to SEQ ID NO: 165,
a heavy chain CDR2 comprising the amino acid sequence according to SEQ ID NO: 166, and
a heavy chain CDR3 comprising the amino acid sequence according to SEQ ID NO: 167, as well as
a light chain variable region including
a light chain CDR1 comprising the amino acid sequence according to SEQ ID NO: 168,
a light chain CDR2 comprising the amino acid sequence according to SEQ ID NO: 169, and
a light chain CDR3 comprising the amino acid sequence according to SEQ ID NO: 170;
a heavy chain variable region including
a heavy chain CDR1 comprising the amino acid sequence according to SEQ ID NO: 171,
a heavy chain CDR2 comprising the amino acid sequence according to SEQ ID NO: 172, and
a heavy chain CDR3 comprising the amino acid sequence according to SEQ ID NO: 173, as well as
a light chain variable region including
a light chain CDR1 comprising the amino acid sequence according to SEQ ID NO: 174,
a light chain CDR2 comprising the amino acid sequence according to SEQ ID NO: 175, and
a light chain CDR3 comprising the amino acid sequence according to SEQ ID NO: 176;
a heavy chain variable region including
a heavy chain CDR1 comprising the amino acid sequence according to SEQ ID NO: 177,
a heavy chain CDR2 comprising the amino acid sequence according to SEQ ID NO: 178, and
a heavy chain CDR3 comprising the amino acid sequence according to SEQ ID NO: 179, as well as
a light chain variable region including
a light chain CDR1 comprising the amino acid sequence according to SEQ ID NO: 180,
a light chain CDR2 comprising the amino acid sequence according to SEQ ID NO: 181, and
a light chain CDR3 comprising the amino acid sequence according to SEQ ID NO: 182;
a heavy chain variable region including
a heavy chain CDR1 comprising the amino acid sequence according to SEQ ID NO: 183,
a heavy chain CDR2 comprising the amino acid sequence according to SEQ ID NO: 184, and
a heavy chain CDR3 comprising the amino acid sequence according to SEQ ID NO: 185, as well as
a light chain variable region including
a light chain CDR1 comprising the amino acid sequence according to SEQ ID NO: 186,
a light chain CDR2 comprising the amino acid sequence according to SEQ ID NO: 187, and
a light chain CDR3 comprising the amino acid sequence according to SEQ ID NO: 188;
a heavy chain variable region including
a heavy chain CDR1 comprising the amino acid sequence according to SEQ ID NO: 189,
a heavy chain CDR2 comprising the amino acid sequence according to SEQ ID NO: 190, and
a heavy chain CDR3 comprising the amino acid sequence according to SEQ ID NO: 191, as well as
a light chain variable region including
a light chain CDR1 comprising the amino acid sequence according to SEQ ID NO: 192,
a light chain CDR2 comprising the amino acid sequence according to SEQ ID NO: 193, and
a light chain CDR3 comprising the amino acid sequence according to SEQ ID NO: 194;
a heavy chain variable region including
a heavy chain CDR1 comprising the amino acid sequence according to SEQ ID NO: 195,
a heavy chain CDR2 comprising the amino acid sequence according to SEQ ID NO: 196, and
a heavy chain CDR3 comprising the amino acid sequence according to SEQ ID NO: 197, as well as
a light chain variable region including
a light chain CDR1 comprising the amino acid sequence according to SEQ ID NO: 198,
a light chain CDR2 comprising the amino acid sequence according to SEQ ID NO: 199, and
a light chain CDR3 comprising the amino acid sequence according to SEQ ID NO: 200;
a heavy chain variable region including
a heavy chain CDR1 comprising the amino acid sequence according to SEQ ID NO: 201,
a heavy chain CDR2 comprising the amino acid sequence according to SEQ ID NO: 202, and
a heavy chain CDR3 comprising the amino acid sequence according to SEQ ID NO: 203, as well as
a light chain variable region including
a light chain CDR1 comprising the amino acid sequence according to SEQ ID NO: 204,
a light chain CDR2 comprising the amino acid sequence according to SEQ ID NO: 205, and
a light chain CDR3 comprising the amino acid sequence according to SEQ ID NO: 206.

[103] (xiii)

(a) An antibody or antigen-binding fragment thereof including a heavy chain variable region comprising the amino acid sequence of SEQ ID NO: 39, and a light chain variable region comprising the amino acid sequence of SEQ ID NO: 40;

(b) An antibody or antigen-binding fragment thereof including a heavy chain variable region comprising the amino acid sequence of SEQ ID NO: 41, and a light chain variable region comprising the amino acid sequence of SEQ ID NO: 42;

(c) An antibody or antigen-binding fragment thereof including a heavy chain variable region comprising the amino acid sequence of SEQ ID NO: 43, and a light chain variable region comprising the amino acid sequence of SEQ ID NO: 44;

(d) An antibody or antigen-binding fragment thereof including a heavy chain variable region comprising the amino acid sequence of SEQ ID NO: 45, and a light chain variable region comprising the amino acid sequence of SEQ ID NO: 46;

(e) An antibody or antigen-binding fragment thereof including a heavy chain variable region comprising the amino acid sequence of SEQ ID NO: 47, and a light chain variable region comprising the amino acid sequence of SEQ ID NO: 48;

(f) An antibody or antigen-binding fragment thereof including a heavy chain variable region comprising the amino acid sequence of SEQ ID NO: 49, and a light chain variable region comprising the amino acid sequence of SEQ ID NO: 50;

(g) An antibody or antigen-binding fragment thereof including a heavy chain variable region comprising the amino acid sequence of SEQ ID NO: 51, and a light chain variable region comprising the amino acid sequence of SEQ ID NO: 52;

(h) An antibody or antigen-binding fragment thereof including a heavy chain variable region comprising the amino acid sequence of SEQ ID NO: 53, and a light chain variable region comprising the amino acid sequence of SEQ ID NO: 54;

(i) An antibody or antigen-binding fragment thereof including a heavy chain variable region comprising the amino acid sequence of SEQ ID NO: 55, and a light chain variable region comprising the amino acid sequence of SEQ ID NO: 56;

(j) An antibody or antigen-binding fragment thereof including a heavy chain variable region comprising the amino acid sequence of SEQ ID NO: 57, and a light chain variable region comprising the amino acid sequence of SEQ ID NO: 58;

(k) An antibody or antigen-binding fragment thereof including a heavy chain variable region comprising the amino acid sequence of SEQ ID NO: 59, and a light chain variable region comprising the amino acid sequence of SEQ ID NO: 60;

(l) An antibody or antigen-binding fragment thereof including a heavy chain variable region comprising the amino acid sequence of SEQ ID NO: 61, and a light chain variable region comprising the amino acid sequence of SEQ ID NO: 62;

(m) An antibody or antigen-binding fragment thereof including a heavy chain variable region comprising the amino acid sequence of SEQ ID NO: 63, and a light chain variable region comprising the amino acid sequence of SEQ ID NO: 64;

(n) An antibody or antigen-binding fragment thereof including a heavy chain variable region comprising the amino acid sequence of SEQ ID NO: 65, and a light chain variable region comprising the amino acid sequence of SEQ ID NO: 66;

(o) An antibody or antigen-binding fragment thereof including a heavy chain variable region comprising the amino acid sequence of SEQ ID NO: 67, and a light chain variable region comprising the amino acid sequence of SEQ ID NO: 68;

(p) An antibody or antigen-binding fragment thereof including a heavy chain variable region comprising the amino acid sequence of SEQ ID NO: 69, and a light chain variable region comprising the amino acid sequence of SEQ ID NO: 70;

(q) An antibody or antigen-binding fragment thereof including a heavy chain variable region comprising the amino acid sequence of SEQ ID NO: 71, and a light chain variable region comprising the amino acid sequence of SEQ ID NO: 72;

(r) An antibody or antigen-binding fragment thereof including a heavy chain variable region comprising the amino acid sequence of SEQ ID NO: 73, and a light chain variable region comprising the amino acid sequence of SEQ ID NO: 74;

(s) An antibody or antigen-binding fragment thereof including a heavy chain variable region comprising the amino acid sequence of SEQ ID NO: 75, and a light chain variable region comprising the amino acid sequence of SEQ ID NO: 76;

(t) An antibody or antigen-binding fragment thereof including a heavy chain variable region comprising the amino acid sequence of SEQ ID NO: 77, and a light chain variable region comprising the amino acid sequence of SEQ ID NO: 78;

(u) An antibody or antigen-binding fragment thereof including a heavy chain variable region comprising the amino acid sequence of SEQ ID NO: 79, and a light chain variable region comprising the amino acid sequence of SEQ ID NO: 80; or (xiv) The antibody or antigen-binding fragment thereof according to any one of [0], [1] to [3], [101] and [102] above, having at least one substitution, addition or deletion in each of at least one or more of variable regions of the antibody or antigen-binding fragment thereof according to any one of (xiii) (a) to (u).

[104] A method for producing, selecting or identifying an antibody or an antigen-binding fragment of an antibody, the method including:

producing, selecting or identifying an antibody or an antigen-binding fragment thereof that satisfies (xi) below, from a group of antibodies or antigen-binding fragments thereof that bind to HER2 or a fragment thereof.

[105] A method for producing, selecting or identifying an antibody or antigen-binding fragment thereof, the method including:

producing, selecting or identifying an antibody or an antigen-binding fragment thereof that satisfies (xii) below, from a group of antibodies or antigen-binding fragments thereof that bind to HER2 or a fragment thereof.

[106] A method for producing, selecting or identifying an antibody or antigen-binding fragment thereof, the method including:

producing, selecting or identifying an antibody or an antigen-binding fragment thereof that satisfies (xiii) below, from a group of antibodies or antigen-binding fragments thereof that bind to HER2 or a fragment thereof.

[107] A method for producing, selecting or identifying an antibody or antigen-binding fragment thereof, the method including:

producing, selecting or identifying an antibody or an antigen-binding fragment thereof that satisfies (xiv) below, from a group of antibodies or antigen-binding fragments thereof that bind to HER2 or a fragment thereof.

[110] The method according to any one of [101] to [103] above, the method including causing an antibody producing cell (for example, a CHO cell) to produce the selected or identified antibody or antigen-binding fragment thereof.

[111] An antibody obtained by the method according to any one of [104] to [107] above.

[112] The method according to any one of [104] to [107] above, wherein the antibody is a monoclonal antibody (for example, an isolated monoclonal antibody).

[113] A pharmaceutical composition containing an HER2-targeting agent that contains the antibody or antigen-binding fragment thereof according to any one of [101] to [103] above.

[114] A pharmaceutical composition containing the antibody or antigen-binding fragment thereof according to any one of [101] to [103] above.

[115] The pharmaceutical composition according to [113] or [114] above, for use in treating cancer.

[120] The method according to any one of [104] to [107] above, wherein the HER2 is an HER2 expressed on an LN229 cell.

[121] The method according to any one of [104] to [107] above, wherein a fragment of the HER2 is a peptide consisting of any amino acid sequence selected from the group consisting of the amino acid sequences according to SEQ ID NOs: 31 to 37 (for example, the amino acid sequences according to SEQ ID NOs: 31 to 36).

According to the present invention, the antibody or antigen-binding fragment thereof of the present invention can be used as an HER2-targeting agent. According to the present invention, the antibody or antigen-binding fragment thereof of the present invention can be used, for example, for detection of a cancer cell and/or treatment of cancer.

BRIEF DESCRIPTION OF DRAWINGS

FIGS. 7A to 7G show flow cytometry (FACS) analysis results of the antibody group acquired in Example 6.

DESCRIPTION OF EMBODIMENTS

<Definitions>

Figure 1A:
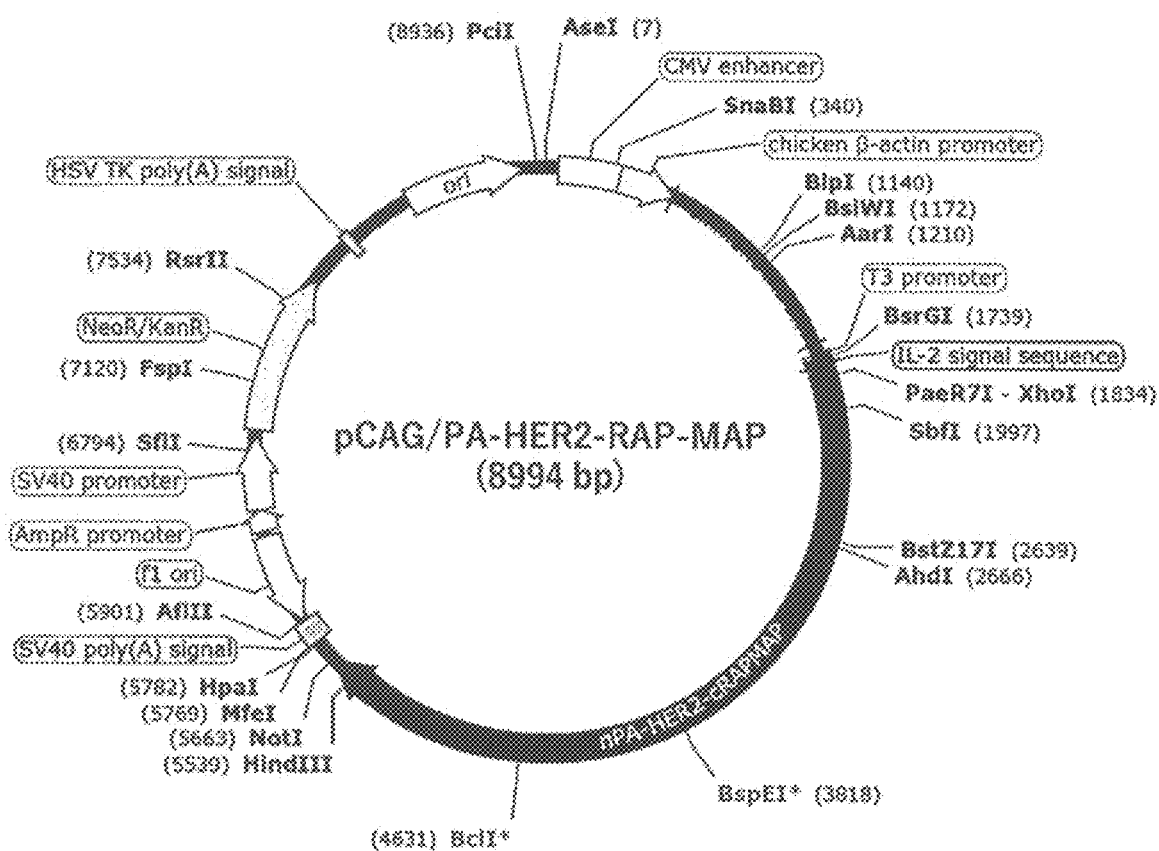
FIG. 1A is a vector map of pCAG/PA-HER2-RAP-MAP used in Examples.

As used herein, a "subject" may be a mammal and is preferably a "patient" as a human subject. More preferably, the subject may be a "cancer patient" suffering from or at risk of a tumor or cancer.

As used herein, the term "antibody" means an immunoglobulin, and refers to a protein having a structure in which two heavy chains (H chains) and two light chains (L chains) stabilized by disulfide bonds are associated with each other. The heavy chain consists of a heavy chain variable region VH, heavy chain constant regions CH1, CH2, and CH3, as well as a hinge region located between CH1 and CH2. The light chain consists of a light chain variable region VL and a light chain constant region CL. Among them, the variable region fragment (Fv) composed of VH and VL is a region directly involved in antigen binding and giving diversity to the antibody. An antigen binding region composed of VL, CL, VH, and CH1 is referred to as a Fab region, and a region composed of a hinge region, CH2, and CH3 is referred to as an Fc region.

Among the variable regions, a region that directly contacts an antigen has a particularly large change, and is called a complementarity-determining region (CDR). A portion having a relatively small variation other than the CDR is referred to as a framework region (FR). Three CDRs exist in each of the variable regions of the light chain and the heavy chain, and are referred to as heavy chains CDR1 to CDR3 and light chains CDR1 to CDR3, respectively, in order from the N-terminal side. The antibody may be a recombinant protein (recombinant antibody) and may be produced in an animal cell, e.g., a Chinese hamster ovary cell (CHO cell). The origin of the antibody is not particularly limited, and examples thereof include a non-human animal antibody, a non-human mammal antibody (for example, a mouse antibody, a rat antibody, a camel antibody), and a human antibody. The antibody may also be a chimeric antibody, a humanized antibody, and a fully human antibody. The antibody may be a polyclonal antibody or a monoclonal antibody, and is preferably a monoclonal antibody. The term "chimeric antibody" is an antibody in which a heavy chain constant region and a light chain constant region are linked to a heavy chain variable region and a light chain variable region of different species, respectively. A humanized antibody means an antibody in which a human antibody has substitutions with corresponding amino acid sequences characteristic of an antibody derived from a non-human. Examples of such an antibody include an antibody that includes the heavy chains CDR1 to CDR3 and the light chains CDR1 to CDR3 of an antibody produced by immunizing a mouse or a rat, in which all other regions including four framework regions (FR) of each of the heavy chain and the light chain are derived from a human antibody. Such an antibody may also be referred to as a CDR-grafted antibody. The term "humanized antibody" may also include a human chimeric antibody. The term "human chimeric antibody" is such an antibody that, in a non-human-derived antibody, the constant region of a non-human-derived antibody is substituted with the constant region of a human antibody. In the human chimeric antibody, from the viewpoint of enhancing the ADCC activity, for example, the subtype of the human antibody used for the constant region can be IgG1. The term "fully human antibody" means an antibody whose variable regions composed of FRs and CDRs and constant regions both are derived from a human antibody. The antibody can also be in the form of an antibody-drug conjugate for the purpose of enhancing the cytotoxicity of the antibody. The antibody may also be a multispecific antibody, e.g., a bispecific antibody, or a trispecific antibody. The antibody may be an isolated antibody or a purified antibody.

As used herein, the term "antigen-binding fragment" means a part of an antibody that maintains binding to an antigen. The antigen-binding fragment may include a heavy chain variable region or a light chain variable region or both of the same of the antibody of the present invention. The antigen-binding fragment may be chimerized or humanized. Examples of the antigen-binding fragment include Fab, Fab', F(ab')$_2$, and Fv. Antibody-binding fragments may also contain recombinantly produced conjugates or functional equivalents (for example, other parts of the antibody in a form of scFv (single chain Fv), diabody, scDb, tandem scFv, leucine zipper type, sc(Fv)$_2$ (single chain (Fv)$_2$), and the like)). The antigen-binding fragment of such an antibody is not particularly limited, but can be obtained, for example, by treating the antibody with an enzyme. For example, the antibody may be digested with papain to obtain a Fab. Alternatively, the antibody may be digested with pepsin to yield F(ab')$_2$, which can be further reduced to yield Fab'. In the present specification, antigen-binding fragments of such antibodies can be used. In scFv, VL and VH may be linked with an artificial polypeptide linker to maintain the same antigen specificity as that of the original antibody. VL and VH may be linked from the N-terminal side in the order of VH and VL, or VL and VH. The linker has a length of about 10 to 25 amino acids, is rich in glycine, and may contain amino acids such as serine and threonine for the purpose of enhancing water solubility.

As used herein, the "binding rate constant" (ka) and the "dissociation rate constant" (kd) are rate constants in a binding/dissociation reaction of two molecules. ka and kd are constants well known to those skilled in the art and can be determined as appropriate using well known techniques, for example, the surface plasmon resonance method. The binding dissociation constant ($K_D$) of an antibody is determined by kd/ka. The antibody may have a $K_D$ value for a target molecule of, for example, $10^{-7}$ M or less, $10^{-1}$ M or less, $10^{-9}$ M or less, $10^{-10}$ M or less, $10^{-12}$ M or less, or $10^{-12}$ M or less.

As used herein, "having a strong (or high) binding affinity" means strongly binding to an antigen, for example, a relatively small $K_D$ value. Weak (or low) binding affinity means weakly binding to an antigen, and, when the binding partner is a cell, the level of the binding affinity may be, for example, the level of the labeled amount of the labeled antibody binding to the cell by flow cytometry.

Herein, the antibody that binds HER2 (or a fragment thereof) may be an antibody that specifically binds to HER2 (or a fragment thereof). Here, "specific" means that the binding affinity when an antibody binds to a defined molecule (for example, HER2) is stronger than the binding affinity when the antibody binds to another molecule (other types of molecules, variants, molecules with other modifications, or molecules without modifications). The specifically binding antibody may have a $K_D$ value of, for example, $10^{-7}$ M or less, $10^{-1}$ M or less, $10^{-9}$ M or less, $10^{-10}$ M or less, $10^{-11}$ M or less, or $10^{-12}$ M or less with respect to HER2. From the viewpoint of the strength of binding affinity, the binding affinity to HER2 may be 2 times or more, 3 times or more, 4 times or more, 5 times or more, 6 times or more, 7 times or more, 8 times or more, 9 times or more, 10 times or more, 100 times or more, 1,000 times or more, 10,000 times or more, or 100,000 times or more in terms of $K_D$ value, and may be stronger than the binding affinity to any of the variants specified below. The strength of binding affinity may be a statistically significant difference (for example, $p<0.05$, $p<0.01$, $p<0.005$, or $p<0.0001$).

As used herein, the "antibody-drug conjugate" (ADC) means a substance in which an antibody and a drug are linked (conjugated). In the ADC, a monoclonal antibody or an antigen-binding fragment thereof may be advantageously used as the antibody. In an ADC, the monoclonal antibody and the drug can be linked via a suitable linker. The ADC binds to a membrane component (for example, a transmembrane protein such as a receptor) on a cell membrane, is taken up into a cell by endocytosis or internalization, is separated from the antibody, and is released into the cell. By introducing a cleavable linker between the antibody and the drug in the cell, it is possible to cleave the linker in the cell, for example, in an endosome, to release the drug from the antibody and release the drug into cytoplasm. As a drug, a cytotoxic agent can be used to kill cells to which the drug has been delivered. Chemotherapeutic agents, radioactive isotopes, and toxins can be used as cytotoxic agents.

As used herein, the term "HER2-targeting agent" means an agent that contains a molecule binding to HER2 or a fragment thereof (for example, a fusion protein containing an antibody that binds to HER2 or a fragment thereof or an antigen-binding fragment of the antibody), and that produces its medicinal effect targeted to HER2. Examples of the HER2-targeting agent include antibodies or antigen-binding fragments thereof that bind to HER2 or a fragment thereof, or agents including any of these. The agent may be the antibody itself having ADCC activity. The agent may be, for example, a cytotoxic agent. The agent may also be a cell having cytotoxic activity (for example, immune cells (for example, T cells, NK cells, and the like)).

As used herein, the term "nucleic acid" means a polymer obtained by connection of nucleotides such as ribonucleic acid (RNA) and deoxyribonucleic acid (DNA). A protein is encoded by DNA and translated from mRNA. The protein-encoding DNA can be operably linked with a control sequence (for example, a promoter). The DNA encoding protein, which is operably linked to a control sequence, may be incorporated into a gene expression vector. The protein-encoding DNA may be cDNA produced by reverse transcription from mRNA. The protein-encoding mRNA may have an m7G cap at the 5' terminal and a poly (A) chain at the 3' terminal. A ribosome binds to the protein-encoding mRNA, and the protein is translated from the mRNA.

As used herein, the term "cancer" is a disease characterized by uncontrolled proliferation of cells. Cancer cells include those that spread locally and those that spread systemically through the bloodstream or lymphatic system. Non-limiting examples of cancer include solid tumors. Non-limiting examples of cancer include hematopoietic tumors. Examples of the solid tumor include lung cancer, pancreas cancer, head and neck cancer, prostate cancer, bladder cancer, breast cancer, esophagus cancer, stomach cancer, colon cancer, uterine cancer, ovarian cancer, skin cancer, thyroid cancer, thymus cancer, kidney cancer, testicular cancer, penile cancer, liver cancer, biliary cancer, brain tumor, bone and soft tissue tumor, retroperitoneal tumor, hemangiosarcomas/lymphangiosarcomas and these metastatic cancers (for example, metastatic solid tumors). Examples of the hematopoietic tumor include leukemia, acute leukemia, chronic leukemia, polycythemia vera, lymphoma, Hodgkin's disease, non-Hodgkin lymphoma (asymptomatic and high grade), multiple myeloma, Waldenstrom's macroglobulinemia, heavy chain disease, myelodysplastic syndrome, ciliary cell leukemia, and myelodysplasia. Examples of acute leukemias include acute lymphocytic leukemia, acute myeloid acute leukemia, acute myeloid leukemia, myeloblastic, promyelocytic, myelomonocytic, monocytic leukemia, and erythroleukemia. Examples of chronic leukemia include chronic myelocytic (granulocytic) leukemia, chronic myelogenous leukemia, and chronic lymphocytic leukemia. The cancer may in particular be a HER2-positive cancer. Whether cells are HER2-positive can be appropriately determined by those skilled in the art using a well-known method. Whether cells are HER2 positive may be determined using the antibody or antigen-binding fragment thereof of the present invention.

As used herein, "treating" encompasses preventive treatment and therapeutic treatment, and means reducing or eliminating the cause of a disease in a patient with the disease, delaying or stopping the progression of the disease, reducing, alleviating, improving, and/or eliminating its symptoms, or suppressing the exacerbation of its symptoms. When the disease is "cancer", it also encompasses suppressing cancer from spreading.

As used herein, "HER2" can be, for example, human HER2. Human HER2 can be encoded, for example, by the base sequence (SEQ ID NO: 1) registered in Genebank accession number: X03363. Human HER2 may also have the amino acid sequence (SEQ ID NO: 2) as registered under the UniprotKB ID: P04626. In human HER2, in the amino acid sequence of SEQ ID NO: 2, the amino acid region of amino acid numbers 1 to 22 is a signal peptide, the amino acid region of amino acid numbers 23 to 652 is an extracellular domain (which may have the amino acid sequence of SEQ ID NO: 3), the amino acid region of amino acid numbers 653 to 675 is a transmembrane domain, and the amino acid region of amino acid numbers 676 to 1255 is a cytoplasmic domain. Examples of HER2 may include naturally found variants of HER2. Because HER2 is a target, it may have reduced or lost its function, but may retain or enhance its function. HER2 that can be recognized as an epitope can be those having, for example, an amino acid region (MPIWKFPD: SEQ ID NO: 34) of amino acid numbers 611 to 618 of the amino acid sequence of SEQ ID NO: 2. HER2 that can be recognized as an epitope can be those having, for example, an amino acid region (PIWKFPD: SEQ ID NO: 35) of amino acid numbers 612 to 618 of the amino acid sequence of SEQ ID NO: 2. As used herein, a peptide consisting of the amino acid region of amino acid numbers 23 to 652 of the amino acid sequence of SEQ ID NO: 2 (SEQ ID NO: 3) is referred to as "HER2ec".

HER2 can be examined for its expression or gene amplification by immunohistochemistry (IHC) or fluorescence in situ hybridization (FISH).

In the IHC method, the expression level can be scored based on the 2018 ASCO/CAP guideline (See Wolff A C, et al: J Clin Oncol 36 (20), 2018: 2105-2122). According to the 2018 ASCO/CAP guidelines, the expression level of HER2 can be scored with four scores as follows:

3+: More than 10% of tumor cells show strong full circumferential membrane staining;
2+: More than 10% of tumor cells show weak to moderate circumferential membrane staining;
1+: More than 10% of tumor cells show faint/barely discernible incomplete membrane staining; and
0: no staining image is seen, or 10% or less of tumor cells show incomplete faint/barely discernible membrane staining.

In FISH, the degree of gene amplification can be evaluated based on the 2007 ASCO/CAP guideline. The HER2 gene is present on chromosome 17 and thus the degree of gene amplification can be assessed by measuring the ratio of the HER2 gene to the number of centromeres of chromosome 17. The test for HER2 can be performed using a commercially available kit.

As used herein, "an amino acid sequence corresponding to . . . " means a corresponding amino acid sequence when aligned.

For the alignment of two amino acid sequences, for example, two or more amino acid sequences can be aligned with default parameters using the CLUSTAL W algorithm. Regarding the alignment algorithm, the fast alignment algorithm and the slow alignment algorithm can be used, and preferably the slow alignment algorithm can be used. The default parameters may satisfy one or more or all parameters selected from the group consisting of, for example, GAP OPEN: 10, GAP EXTENSION: 0.1, KTUP: 1, WINDOW LENGTH: 5, TOPDIAG: 5, and PAIRGAP: 3. Thereby, the corresponding amino acid sequence can be identified. Thus, the identity of the amino acid sequence can be determined.

As used herein, "antibodies compete in the binding to HER2" means that both antibodies cannot bind to HER2 at the same time because the binding sites (epitopes) on HER2 overlap and compete for the binding site of HER2. Whether antibodies compete in the binding to HER2 can be determined by an antibody competition test.

As used herein, an "epitope" means a site on the surface of a target molecule to which an antibody binds.

<Antibody or Antigen-Binding Fragment Thereof of the Present Invention>

An antibody or antigen-binding fragment thereof of the present invention is an antibody or antigen-binding fragment thereof that binds to HER2 or a fragment thereof. Examples of the antibody or antigen-binding fragment thereof of the present invention may include an antibody or antigen-binding fragment thereof having a mutation selected from the group consisting of insertion, deletion, addition and substitution of one to several amino acids. In a certain embodiment, provided are antibodies or antigen-binding fragments thereof including at least one CDR, at least two, at least three, or more CDRs that are substantially identical to at least one CDR, at least two, at least three, or more CDRs in an antibody or antigen-binding fragment thereof of the present invention. In another embodiment, an antibody or antigen-binding fragment thereof is provided that includes an antibody having at least two, three, four, five, or six CDRs that are substantially identical to at least two, three, four, five, or six CDRs in or derived from the antibody or antigen-binding fragment thereof of the present invention. In a certain embodiment, an antibody or antigen-binding fragment thereof is provided that includes at least one, two, three, four, five, or six CDRs that are at least about 85%, 86%, 87%, 88%, 89%, 90%, 95%, 96%, 97%, 98%, or 99% identical to at least one, two, or three CDRs in the antibody or antigen-binding fragment thereof of the present invention. In another embodiment, in the at least one, two, three, four, five, or six CDRs, at least one insertion, deletion, addition, or substitution is included in at least one, two, three, four, five, or six CDRs in or derived from the antibody or antigen-binding fragment thereof of the present invention. Examples of the antibody or antigen-binding fragment thereof of the present invention may include an antibody or antigen-binding fragment thereof having an amino acid sequence identity of 80% or more, 85% or more, 90% or more, or 95% or more and having antigenic specificity. Examples of the antibody or antigen-binding fragment thereof of the present invention may include an antibody or antigen-binding fragment thereof having a mutation selected from the group consisting of insertion, deletion, addition and substitution of one to several amino acids in a framework (FR) region of the heavy chain variable region or the light chain variable region.

The antibody or antigen-binding fragment thereof of the present invention may be preferably an antibody that specifically binds to HER2. The antibody or antigen-binding fragment thereof of the present invention has a binding affinity (or reactivity) for HER2 expressed on cancer cells. Therefore, it can be used for targeting cancer cells. The antibody or antigen-binding fragment thereof of the present invention can more preferably have a stronger binding affinity (or reactivity) to HER2 expressed on cancer cells than to HER2 expressed on non-cancer cells. Therefore, it can be used for specifically targeting cancer cells. The antibody or antigen-binding fragment thereof of the present invention further preferably does not significantly react (for example, does not react at all, or does not substantially react) with HER2 expressed on non-cancer cells, but can specifically react to HER2 expressed on cancer cells. Therefore, it can be used for targeting (particularly, specifically targeting) cancer cells.

The antibody or antigen-binding fragment thereof of the present invention may be preferably a monoclonal antibody from the viewpoint of being used as a pharmaceutical component. The antibody or antigen-binding fragment thereof of the present invention is preferably an isolated monoclonal antibody or an antigen-binding fragment of an isolated monoclonal antibody from the viewpoint of being used as a pharmaceutical component. According to the present invention, a pharmaceutical composition containing an isolated monoclonal antibody or an antigen-binding fragment of an isolated monoclonal antibody, and a pharmaceutically acceptable additive, may be provided.

The antibody or antigen-binding fragment thereof of the present invention is:
  (i) an antibody or antigen-binding fragment thereof that binds to a peptide including any amino acid sequence selected from the group consisting of the amino acid sequences of SEQ ID NOs: 31 to 37 (for example, the amino acid sequences of SEQ ID NOs: 31 to 36);
  (ii) An antibody or antigen-binding fragment thereof that has a stronger binding affinity (or reactivity) to a peptide consisting of an extracellular domain of HER2 set forth in SEQ ID NO: 3 than to a variant of an extracellular domain of HER2 set forth in SEQ ID NO: 2 having one or more amino acid mutations selected from the group consisting of W614A, K615A, and F616A in a peptide consisting of a part (a region of amino acid numbers 603 to 622) of the extracellular domain of HER2, for example, a stronger binding affinity (or reactivity) to the peptide consisting of the extracellular domain of HER2 set forth in SEQ ID NO: 3 than to a variant of the extracellular domain of HER2 having a point mutation of W614A, a variant of the extracellular domain of HER2 having a point mutation of F616A, a variant of the extracellular domain of HER2 having two point mutations of W614A and F616A, or a variant of the extracellular domain of HER2 having two point mutations of K615A and F616A, in the peptide consisting of the part of the extracellular domain of HER2 set forth in SEQ ID NO: 2 (the region of amino acid numbers 603 to 622) {in the above, the part of the extracellular domain of HER2 may be a region of amino acid numbers 613 to 622 of the amino acid sequence set forth in SEQ ID NO: 2}.

Here, W614A means that the amino acid residue corresponding to tryptophan (W) of amino acid number 614 in the amino acid sequence of HER2 set forth in SEQ ID NO: 2 is substituted with alanine (A); K615A means that the amino acid residue corresponding to lysine (K) of amino acid number 615 in the amino acid sequence of HER2 set forth in SEQ ID NO: 2 is substituted with alanine (A); and F616A means that the amino acid residue corresponding to phenylalanine (F) of amino acid number 616 in the amino acid sequence of HER2 described in SEQ ID NO: 2 is substituted with alanine (A). The peptide may be a synthetic polypeptide. The peptide is not glycosylated in a preferred embodiment.

The binding reactivity to HER2 can also be assessed by enzyme-linked immunosorbent assay (ELISA). In ELISA, for example, the presence or amount of an enzyme linked to an antibody can be assessed according to the amount of a reactant of a substrate to the enzyme. For example, when horseradish peroxidase (HRP) is used as an enzyme and 3,3',5,5'-tetramethylbenzidine (TMB) is used as a substrate, TMB is oxidized to develop a blue color having maximum absorption at 370 nm and 652 nm. When the reaction stop solution containing sulfuric acid is further brought into contact, a yellow color having a maximum absorption at 450 nm is developed. For example, by measuring the absorption at 652 nm, the amount of reacted antibody can be estimated, and the reactivity of the antibody to an antigen can be assessed based on the amount of reacted antibody. Then, it can be assessed that the reactivity of the antibody to an antigen is higher as the amount of the reacted antibody is larger. The reactivity to HER2 of the antibody of the present invention can be 1.5 times or more, 2 times or more, 3 times or more, 4 times or more, 5 times or more, 6 times or more, 7 times or more, 8 times or more, 9 times or more, 10 times or more, 100 times or more, 1,000 times or more, 10,000 times or more, or 100,000 times or more stronger than the binding affinity to any of the variants above, in terms of the binding reactivity (the amount of reacted antibody). The strength of binding reactivity may be a statistically significant difference (for example, $p<0.05$, $p<0.01$, $p<0.005$, or $p<0.0001$).

The antibody or antigen-binding fragment thereof of the present invention is described in detail below.

Any of the antibodies or antigen-binding fragments thereof of the present invention binds to HER2 expressed on cancer cells (for example, LN229 cells). The antibody or antigen-binding fragment thereof of the present invention is preferably has a stronger binding reactivity to HER2 expressed on cancer cells than to HER2 expressed on non-cancer cells. In one embodiment, the antibody or antigen-binding fragment thereof of the present invention binds to HER2 expressed on cancer cells (for example, LN229 cells) and does not show significant binding to HER2 expressed on non-cancer cells (for example, normal cells).

The antibody or antigen-binding fragment thereof of the present invention can be:
  (i) an antibody or antigen-binding fragment thereof that binds to a peptide including any amino acid sequence selected from the group consisting of the amino acid sequences of SEQ ID NOs: 31 to 37 (for example, the amino acid sequences of SEQ ID NOs: 31 to 36). The peptide including any amino acid sequence selected from the group consisting of the amino acid sequences of SEQ ID NOs: 31 to 37 (for example, the amino acid sequences of SEQ ID NOs: 31 to 36) can be a partial peptide of the amino acid sequence of SEQ ID NO: 2.

The peptide including any amino acid sequence selected from the group consisting of the amino acid sequences of SEQ ID NOs: 31 to 37 (for example, the amino acid sequences of SEQ ID NOs: 31 to 36) is a partial peptide of the amino acid sequence of SEQ ID NO: 2, and can be 10 to 20 amino acids in length, 11 to 19 amino acids in length, 12 to 18 amino acids in length, 13 to 17 amino acids in length, 14 to 16 amino acids in length, or about 15 amino acids in length. The peptide including any amino acid sequence selected from the group consisting of the amino acid sequences of SEQ ID NOs: 31 to 37 (for example, the amino acid sequences of SEQ ID NOs: 31 to 36) can be a peptide of the amino acid sequence selected from the group consisting of the amino acid sequences of SEQ ID NOs: 31 to 37 (for example, the amino acid sequences of SEQ ID NOs 31 to 36). This region is believed to have a configuration accessible to an antibody at HER2 expressed on cancer cell membranes, and thus an antibody targeting this region may bind to cancer cells with a stronger binding affinity (or reactivity) than to non-cancer cells. In a certain preferable embodiment, an antibody targeting this region does not significantly react to HER2 expressed on non-cancer cells, but can specifically react to HER2 expressed on cancer cells. It is not necessary that the peptide itself should have a sugar chain modification, and the peptide does not have to have a sugar chain modification.

Here, the peptide is not particularly limited, but may be preferably a synthetic peptide.

The antibody or antigen-binding fragment thereof of the present invention can:

(ii) have a stronger binding affinity (or reactivity) to a peptide consisting of an extracellular domain of HER2 set forth in SEQ ID NO: 3 than to a variant of an extracellular domain of HER2 set forth in SEQ ID NO: 2 having one or more amino acid mutations selected from the group consisting of W614A, K615A, and F616A in a peptide consisting of a part (a region of amino acid numbers 603 to 622) of the extracellular domain of HER2; or have a stronger binding affinity (or reactivity) to a peptide consisting of an extracellular domain of HER2 set forth in SEQ ID NO: 3 than to a variant of an extracellular domain of HER2 having a point mutation of W614A in the peptide consisting of the part (the region of amino acid numbers 603 to 622) of the extracellular domain of HER2 set forth in SEQ ID NO: 2, or a variant of an extracellular domain of HER2 having a mutation consisting of two point mutations of K615A and F616A in the same peptide; or have a stronger binding affinity (or reactivity) to a peptide consisting of an extracellular domain of HER2 set forth in SEQ ID NO: 3 than to a variant peptide of an extracellular domain of HER2 having a point mutation of K615A, or to a variant peptide of an extracellular domain of HER2 having a point mutation of F616A, or to a variant peptide of an extracellular domain of HER2 having a mutation consisting of two point mutations of W614A and F616A in the peptide consisting of the part of the extracellular domain of HER2 set forth in SEQ ID NO: 2 (the region of amino acid numbers 603 to 622). Antibodies that bind to or around this region may bind to cancer cells with a stronger binding affinity (or reactivity) to cancer cells than to non-cancer cells. In the above, the part of the extracellular domain of HER2 may be a region of amino acid numbers 613 to 622 of the amino acid sequence set forth in SEQ ID NO: 2.

Here, the extracellular domain may be a peptide expressed on a non-cancer cell or a cancer cell, or a synthetic peptide. The extracellular domain may preferably be a synthetic peptide. These antibodies may also compete with each other in the binding to a peptide consisting of the part of the extracellular domain of HER2 (the region of amino acid numbers 603 to 622). These antibodies may also compete with each other in the binding to HER2 expressed on cancer cells (for example, LN229 cells).

The antibody or antigen-binding fragment thereof of the present invention can be:

(iii) an antibody or antigen-binding fragment including:
a heavy chain variable region including:
a heavy chain CDR1 comprising the amino acid sequence of SEQ ID NO: 18;
a heavy chain CDR2 comprising the amino acid sequence of SEQ ID NO: 19; and
a heavy chain CDR3 comprising the amino acid sequence of SEQ ID NO: 20; as well as
a light chain variable region including:
a light chain CDR1 comprising the amino acid sequence of SEQ ID NO: 21;
a light chain CDR2 comprising the amino acid sequence of SEQ ID NO: 22, and
a light chain CDR3 comprising the amino acid sequence according to SEQ ID NO: 23;

(iv) a heavy chain variable region including:
a heavy chain CDR1 comprising an amino acid sequence of SEQ ID NO: 24;
a heavy chain CDR2 comprising an amino acid sequence of SEQ ID NO: 25, and
a heavy chain CDR3 comprising an amino acid sequence of SEQ ID NO: 26, as well as
a light chain variable region including:
a light chain CDR1 comprising an amino acid sequence of SEQ ID NO: 27, and
a light chain CDR2 comprising an amino acid sequence of SEQ ID NO: 28; and
a light chain CDR3 comprising an amino acid sequence of SEQ ID NO: 29;

(v) an antibody or antigen-binding fragment thereof that competes with the antibody of (iii) above in the binding to HER2; or (vi) an antibody or antigen-binding fragment thereof that competes with the antibody of (iv) above in the binding to HER2. The antibody or antigen-binding fragment thereof of the present invention may also be an antibody or antigen-binding fragment thereof of the present invention that has at least one or more (for example, several, for example two, three, four, or five) amino acid mutations selected from the group consisting of substitution, addition, insertion, and deletion in at least one CDR of any of (iii) or (iv) above. These antibodies or antigen-binding fragments thereof can bind to cancer cells with a stronger binding affinity than to non-cancer cells. These antibodies or antigen-binding fragments thereof preferably do not significantly react to HER2 expressed on non-cancer cells, but can specifically react to HER2 expressed on cancer cells. The antibody or antigen-binding fragment thereof of the present invention can be a non-human animal antibody or antigen-binding fragment thereof. The non-human animal may be, for example, a rodent, for example, a mouse. The antibody or antigen-binding fragment thereof of the present invention may be preferably a chimeric antibody or a human chimeric antibody. The antibody or antigen-binding fragment thereof of the present invention can be more preferably a humanized antibody or an antigen-binding fragment of a humanized antibody.

The antibody or antigen-binding fragment thereof of the present invention can be:

(vii) an antibody or antigen-binding fragment thereof including a heavy chain variable region comprising an amino acid sequence of the heavy chain variable region of SEQ ID NO: 14, and a light chain variable region comprising an amino acid sequence of the light chain variable region of SEQ ID NO: 15;

(viii) an antibody or antigen-binding fragment thereof including a heavy chain variable region comprising an amino acid sequence of the heavy chain variable region of SEQ ID NO: 16, and a light chain variable region comprising an amino acid sequence of the light chain variable region of SEQ ID NO: 17;

(ix) an antibody or antigen-binding fragment thereof that competes with the antibody of (vii) for binding to HER2 (for example, a peptide consisting of a part of the extracellular domain of HER2 (region of amino acid numbers 603 to 622), or HER2 expressed on LN229 cells}; or (x) an antibody or antigen-binding fragment thereof that competes with the antibody of (viii) in the binding to HER2 (for example, a peptide consisting of a part of the extracellular domain of HER2 (region of amino acid numbers 603 to 622), or HER2 expressed on LN229 cells}; or The antibody or antigen-binding fragment thereof of the present invention may also be an antibody or antigen-binding fragment thereof of the present invention that has at least one or more (for example, several) amino acid mutations selected from the group consisting of at least one of substitution, addition, insertion, and deletion in each variable region of (vii) or (viii) above. In a certain embodiment, at least one or more (for example, several) amino acid mutations selected from the group consisting of substitutions, additions, insertions, and deletions in each variable region can be mutations other than CDRs.

The antibody or antigen-binding fragment thereof of the present invention can be:

(xi) an antibody or antigen-binding fragment thereof that binds to a peptide including an amino acid sequence of SEQ ID NO: 37.

The antibody or antigen-binding fragment thereof of the present invention can be an antibody or antigen-binding fragment thereof that includes:

(xii) a heavy chain variable region including
a heavy chain CDR1 comprising an amino acid sequence according to SEQ ID NO: 81,
a heavy chain CDR2 comprising an amino acid sequence according to SEQ ID NO: 82,
a heavy chain CDR3 comprising the amino acid sequence according to SEQ ID NO: 83, as well as
a light chain variable region including
a light chain CDR1 comprising an amino acid sequence according to SEQ ID NO: 84,
a light chain CDR2 comprising an amino acid sequence according to SEQ ID NO: 85, and
a light chain CDR3 comprising the amino acid sequence according to SEQ ID NO: 86;
a heavy chain variable region including
a heavy chain CDR1 comprising an amino acid sequence according to SEQ ID NO: 87,
a heavy chain CDR2 comprising an amino acid sequence according to SEQ ID NO: 88, and
a heavy chain CDR3 comprising the amino acid sequence according to SEQ ID NO: 89, as well as
a light chain variable region including
a light chain CDR1 comprising an amino acid sequence according to SEQ ID NO: 90,
a light chain CDR2 comprising an amino acid sequence according to SEQ ID NO: 91, and
a light chain CDR3 comprising the amino acid sequence according to SEQ ID NO: 92;
a heavy chain variable region including
a heavy chain CDR1 comprising an amino acid sequence according to SEQ ID NO: 93,
a heavy chain CDR2 comprising an amino acid sequence according to SEQ ID NO: 94, and
a heavy chain CDR3 comprising the amino acid sequence according to SEQ ID NO: 95, as well as
a light chain variable region including
a light chain CDR1 comprising an amino acid sequence according to SEQ ID NO: 96,
a light chain CDR2 comprising an amino acid sequence according to SEQ ID NO: 97, and
a light chain CDR3 comprising the amino acid sequence according to SEQ ID NO: 98;
a heavy chain variable region including
a heavy chain CDR1 comprising an amino acid sequence according to SEQ ID NO: 99,
a heavy chain CDR2 comprising an amino acid sequence according to SEQ ID NO: 100, and
a heavy chain CDR3 comprising the amino acid sequence according to SEQ ID NO: 101, as well as
a light chain variable region including
a light chain CDR1 comprising an amino acid sequence according to SEQ ID NO: 102,
a light chain CDR2 comprising an amino acid sequence according to SEQ ID NO: 103, and
a light chain CDR3 comprising the amino acid sequence according to SEQ ID NO: 104;
a heavy chain variable region including
a heavy chain CDR1 comprising an amino acid sequence according to SEQ ID NO: 105,
a heavy chain CDR2 comprising an amino acid sequence according to SEQ ID NO: 106, and
a heavy chain CDR3 comprising the amino acid sequence according to SEQ ID NO: 107, as well as
a light chain variable region including
a light chain CDR1 comprising an amino acid sequence according to SEQ ID NO: 108,
a light chain CDR2 comprising an amino acid sequence according to SEQ ID NO: 109, and
a light chain CDR3 comprising the amino acid sequence according to SEQ ID NO: 110;
a heavy chain variable region including
a heavy chain CDR1 comprising an amino acid sequence according to SEQ ID NO: 111,
a heavy chain CDR2 comprising an amino acid sequence according to SEQ ID NO: 112, and
a heavy chain CDR3 comprising the amino acid sequence according to SEQ ID NO: 113, as well as
a light chain variable region including
a light chain CDR1 comprising an amino acid sequence according to SEQ ID NO: 114,
a light chain CDR2 comprising an amino acid sequence according to SEQ ID NO: 115, and
a light chain CDR3 comprising the amino acid sequence according to SEQ ID NO: 116;

a heavy chain variable region including
a heavy chain CDR1 comprising an amino acid sequence according to SEQ ID NO: 117,
a heavy chain CDR2 comprising an amino acid sequence according to SEQ ID NO: 118, and
a heavy chain CDR3 comprising the amino acid sequence according to SEQ ID NO: 119, as well as
a light chain variable region including
a light chain CDR1 comprising an amino acid sequence according to SEQ ID NO: 120,
a light chain CDR2 comprising an amino acid sequence according to SEQ ID NO: 121, and
a light chain CDR3 comprising the amino acid sequence according to SEQ ID NO: 122;
a heavy chain variable region including
a heavy chain CDR1 comprising an amino acid sequence according to SEQ ID NO: 123,
a heavy chain CDR2 comprising an amino acid sequence according to SEQ ID NO: 124, and
a heavy chain CDR3 comprising the amino acid sequence according to SEQ ID NO: 125, as well as
a light chain variable region including
a light chain CDR1 comprising an amino acid sequence according to SEQ ID NO: 126,
a light chain CDR2 comprising an amino acid sequence according to SEQ ID NO: 127, and
a light chain CDR3 comprising the amino acid sequence according to SEQ ID NO: 128;
a heavy chain variable region including
a heavy chain CDR1 comprising an amino acid sequence according to SEQ ID NO: 129,
a heavy chain CDR2 comprising an amino acid sequence according to SEQ ID NO: 130, and
a heavy chain CDR3 comprising the amino acid sequence according to SEQ ID NO: 131, as well as
a light chain variable region including
a light chain CDR1 comprising an amino acid sequence according to SEQ ID NO: 132,
a light chain CDR2 comprising an amino acid sequence according to SEQ ID NO: 133, and
a light chain CDR3 comprising the amino acid sequence according to SEQ ID NO: 134;
a heavy chain variable region including
a heavy chain CDR1 comprising an amino acid sequence according to SEQ ID NO: 135,
a heavy chain CDR2 comprising an amino acid sequence according to SEQ ID NO: 136, and
a heavy chain CDR3 comprising the amino acid sequence according to SEQ ID NO: 137, as well as
a light chain variable region including
a light chain CDR1 comprising an amino acid sequence according to SEQ ID NO: 138,
a light chain CDR2 comprising an amino acid sequence according to SEQ ID NO: 139, and
a light chain CDR3 comprising the amino acid sequence according to SEQ ID NO: 140;
a heavy chain variable region including
a heavy chain CDR1 comprising an amino acid sequence according to SEQ ID NO: 141,
a heavy chain CDR2 comprising an amino acid sequence according to SEQ ID NO: 142, and
a heavy chain CDR3 comprising the amino acid sequence according to SEQ ID NO: 143, as well as
a light chain variable region including
a light chain CDR1 comprising an amino acid sequence according to SEQ ID NO: 144,
a light chain CDR2 comprising an amino acid sequence according to SEQ ID NO: 145, and
a light chain CDR3 comprising the amino acid sequence according to SEQ ID NO: 146;
a heavy chain variable region including
a heavy chain CDR1 comprising an amino acid sequence according to SEQ ID NO: 147,
a heavy chain CDR2 comprising an amino acid sequence according to SEQ ID NO: 148, and
a heavy chain CDR3 comprising the amino acid sequence according to SEQ ID NO: 149, as well as
a light chain variable region including
a light chain CDR1 comprising an amino acid sequence according to SEQ ID NO: 150,
a light chain CDR2 comprising an amino acid sequence according to SEQ ID NO: 151, and
a light chain CDR3 comprising the amino acid sequence according to SEQ ID NO: 152;
a heavy chain variable region including
a heavy chain CDR1 comprising an amino acid sequence according to SEQ ID NO: 153,
a heavy chain CDR2 comprising an amino acid sequence according to SEQ ID NO: 154, and
a heavy chain CDR3 comprising the amino acid sequence according to SEQ ID NO: 155, as well as
a light chain variable region including
a light chain CDR1 comprising an amino acid sequence according to SEQ ID NO: 156,
a light chain CDR2 comprising an amino acid sequence according to SEQ ID NO: 157, and
a light chain CDR3 comprising the amino acid sequence according to SEQ ID NO: 158;
a heavy chain variable region including
a heavy chain CDR1 comprising an amino acid sequence according to SEQ ID NO: 159,
a heavy chain CDR2 comprising an amino acid sequence according to SEQ ID NO: 160, and
a heavy chain CDR3 comprising the amino acid sequence according to SEQ ID NO: 161, as well as
a light chain variable region including
a light chain CDR1 comprising an amino acid sequence according to SEQ ID NO: 162,
a light chain CDR2 comprising an amino acid sequence according to SEQ ID NO: 163, and
a light chain CDR3 comprising the amino acid sequence according to SEQ ID NO: 164;
a heavy chain variable region including
a heavy chain CDR1 comprising an amino acid sequence according to SEQ ID NO: 165,
a heavy chain CDR2 comprising an amino acid sequence according to SEQ ID NO: 166, and
a heavy chain CDR3 comprising the amino acid sequence according to SEQ ID NO: 167, as well as
a light chain variable region including
a light chain CDR1 comprising an amino acid sequence according to SEQ ID NO: 168,
a light chain CDR2 comprising an amino acid sequence according to SEQ ID NO: 169, and
a light chain CDR3 comprising the amino acid sequence according to SEQ ID NO: 170;
a heavy chain variable region including
a heavy chain CDR1 comprising an amino acid sequence according to SEQ ID NO: 171,
a heavy chain CDR2 comprising an amino acid sequence according to SEQ ID NO: 172, and
a heavy chain CDR3 comprising the amino acid sequence according to SEQ ID NO: 173, as well as a light chain variable region including
a light chain CDR1 comprising an amino acid sequence according to SEQ ID NO: 174,
a light chain CDR2 comprising an amino acid sequence according to SEQ ID NO: 175, and
a light chain CDR3 comprising the amino acid sequence according to SEQ ID NO: 176;
a heavy chain variable region including
a heavy chain CDR1 comprising an amino acid sequence according to SEQ ID NO: 177,
a heavy chain CDR2 comprising an amino acid sequence according to SEQ ID NO: 178, and
a heavy chain CDR3 comprising the amino acid sequence according to SEQ ID NO: 179, as well as
a light chain variable region including
a light chain CDR1 comprising an amino acid sequence according to SEQ ID NO: 180,
a light chain CDR2 comprising an amino acid sequence according to SEQ ID NO: 181, and
a light chain CDR3 comprising the amino acid sequence according to SEQ ID NO: 182;
a heavy chain variable region including
a heavy chain CDR1 comprising an amino acid sequence according to SEQ ID NO: 183,
a heavy chain CDR2 comprising an amino acid sequence according to SEQ ID NO: 184, and
a heavy chain CDR3 comprising the amino acid sequence according to SEQ ID NO: 185, as well as
a light chain variable region including
a light chain CDR1 comprising an amino acid sequence according to SEQ ID NO: 186,
a light chain CDR2 comprising an amino acid sequence according to SEQ ID NO: 187, and
a light chain CDR3 comprising the amino acid sequence according to SEQ ID NO: 188;
a heavy chain variable region including
a heavy chain CDR1 comprising an amino acid sequence according to SEQ ID NO: 189,
a heavy chain CDR2 comprising an amino acid sequence according to SEQ ID NO: 190, and
a heavy chain CDR3 comprising the amino acid sequence according to SEQ ID NO: 191, as well as
a light chain variable region including
a light chain CDR1 comprising an amino acid sequence according to SEQ ID NO: 192,
a light chain CDR2 comprising an amino acid sequence according to SEQ ID NO: 193, and
a light chain CDR3 comprising the amino acid sequence according to SEQ ID NO: 194;
a heavy chain variable region including
a heavy chain CDR1 comprising an amino acid sequence according to SEQ ID NO: 195,
a heavy chain CDR2 comprising an amino acid sequence according to SEQ ID NO: 196, and
a heavy chain CDR3 comprising the amino acid sequence according to SEQ ID NO: 197, as well as
a light chain variable region including
a light chain CDR1 comprising an amino acid sequence according to SEQ ID NO: 198,
a light chain CDR2 comprising an amino acid sequence according to SEQ ID NO: 199, and
a light chain CDR3 comprising the amino acid sequence according to SEQ ID NO: 200;
a heavy chain variable region including
a heavy chain CDR1 comprising an amino acid sequence according to SEQ ID NO: 201,
a heavy chain CDR2 comprising an amino acid sequence according to SEQ ID NO: 202, and
a heavy chain CDR3 comprising the amino acid sequence according to SEQ ID NO: 203, as well as
a light chain variable region including
a light chain CDR1 comprising an amino acid sequence according to SEQ ID NO: 204,
a light chain CDR2 comprising an amino acid sequence according to SEQ ID NO: 205, and
a light chain CDR3 comprising the amino acid sequence according to SEQ ID NO: 206.

The antibody or antigen-binding fragment thereof of the present invention can be:

(xiii)
(a) an antibody or antigen-binding fragment thereof including a heavy chain variable region comprising an amino acid sequence of the heavy chain variable region of SEQ ID NO: 39, and a light chain variable region comprising an amino acid sequence of the light chain variable region of SEQ ID NO: 40;
(b) an antibody or antigen-binding fragment thereof including a heavy chain variable region comprising an amino acid sequence of the heavy chain variable region of SEQ ID NO: 41, and a light chain variable region comprising an amino acid sequence of the light chain variable region of SEQ ID NO: 42;
(c) an antibody or antigen-binding fragment thereof including a heavy chain variable region comprising an amino acid sequence of the heavy chain variable region of SEQ ID NO: 43, and a light chain variable region comprising an amino acid sequence of the light chain variable region of SEQ ID NO: 44;
(d) an antibody or antigen-binding fragment thereof including a heavy chain variable region comprising an amino acid sequence of the heavy chain variable region of SEQ ID NO: 45, and a light chain variable region comprising an amino acid sequence of the light chain variable region of SEQ ID NO: 46;
(e) an antibody or antigen-binding fragment thereof including a heavy chain variable region comprising an amino acid sequence of the heavy chain variable region of SEQ ID NO: 47, and a light chain variable region comprising an amino acid sequence of the light chain variable region of SEQ ID NO: 48;
(f) an antibody or antigen-binding fragment thereof including a heavy chain variable region comprising an amino acid sequence of the heavy chain variable region of SEQ ID NO: 49, and a light chain variable region comprising an amino acid sequence of the light chain variable region of SEQ ID NO: 50;
(g) an antibody or antigen-binding fragment thereof including a heavy chain variable region comprising an amino acid sequence of the heavy chain variable region of SEQ ID NO: 51, and a light chain variable region comprising an amino acid sequence of the light chain variable region of SEQ ID NO: 52;
(h) an antibody or antigen-binding fragment thereof including a heavy chain variable region comprising an amino acid sequence of the heavy chain variable region of SEQ ID NO: 53, and a light chain variable region comprising an amino acid sequence of the light chain variable region of SEQ ID NO: 54;
(i) an antibody or antigen-binding fragment thereof including a heavy chain variable region comprising an amino acid sequence of the heavy chain variable region of SEQ ID NO: 55, and a light chain variable region comprising an amino acid sequence of the light chain variable region of SEQ ID NO: 56;

(j) an antibody or antigen-binding fragment thereof including a heavy chain variable region comprising an amino acid sequence of the heavy chain variable region of SEQ ID NO: 57, and a light chain variable region comprising an amino acid sequence of the light chain variable region of SEQ ID NO: 58;

(k) an antibody or antigen-binding fragment thereof including a heavy chain variable region comprising an amino acid sequence of the heavy chain variable region of SEQ ID NO: 59, and a light chain variable region comprising an amino acid sequence of the light chain variable region of SEQ ID NO: 60;

(l) an antibody or antigen-binding fragment thereof including a heavy chain variable region comprising an amino acid sequence of the heavy chain variable region of SEQ ID NO: 61, and a light chain variable region comprising an amino acid sequence of the light chain variable region of SEQ ID NO: 62;

(m) an antibody or antigen-binding fragment thereof including a heavy chain variable region comprising an amino acid sequence of the heavy chain variable region of SEQ ID NO: 63, and a light chain variable region comprising an amino acid sequence of the light chain variable region of SEQ ID NO: 64;

(n) an antibody or antigen-binding fragment thereof including a heavy chain variable region comprising an amino acid sequence of the heavy chain variable region of SEQ ID NO: 65, and a light chain variable region comprising an amino acid sequence of the light chain variable region of SEQ ID NO: 66;

(o) an antibody or antigen-binding fragment thereof including a heavy chain variable region comprising an amino acid sequence of the heavy chain variable region of SEQ ID NO: 67, and a light chain variable region comprising an amino acid sequence of the light chain variable region of SEQ ID NO: 68;

(p) an antibody or antigen-binding fragment thereof including a heavy chain variable region comprising an amino acid sequence of the heavy chain variable region of SEQ ID NO: 69, and a light chain variable region comprising an amino acid sequence of the light chain variable region of SEQ ID NO: 70;

(q) an antibody or antigen-binding fragment thereof including a heavy chain variable region comprising an amino acid sequence of the heavy chain variable region of SEQ ID NO: 71, and a light chain variable region comprising an amino acid sequence of the light chain variable region of SEQ ID NO: 72;

(r) an antibody or antigen-binding fragment thereof including a heavy chain variable region comprising an amino acid sequence of the heavy chain variable region of SEQ ID NO: 73, and a light chain variable region comprising an amino acid sequence of the light chain variable region of SEQ ID NO: 74;

(s) an antibody or antigen-binding fragment thereof including a heavy chain variable region comprising an amino acid sequence of the heavy chain variable region of SEQ ID NO: 75, and a light chain variable region comprising an amino acid sequence of the light chain variable region of SEQ ID NO: 76;

(t) an antibody or antigen-binding fragment thereof including a heavy chain variable region comprising an amino acid sequence of the heavy chain variable region of SEQ ID NO: 77, and a light chain variable region comprising an amino acid sequence of the light chain variable region of SEQ ID NO: 78;

(u) an antibody or antigen-binding fragment thereof including a heavy chain variable region comprising an amino acid sequence of the heavy chain variable region of SEQ ID NO: 79, and a light chain variable region comprising an amino acid sequence of the light chain variable region of SEQ ID NO: 80;

(xiv) an antibody or antigen-binding fragment thereof that competes with each antibody of (xii)(a) to (u) for binding to HER2 (for example, a peptide consisting of a part of the extracellular domain of HER2 (region of amino acid numbers 603 to 622), or HER2 expressed on LN229 cells}; or As will be apparent to those skilled in the art, the following description of the antibody or antigen-binding fragment thereof of the present invention can be applied to the antibodies (xi) to (xiv) or the antigen-binding fragments thereof.

The antibody or antigen-binding fragment thereof of the present invention is an isolated antibody or antigen-binding fragment thereof that has a stronger binding affinity (or reactivity) to HER2 expressed on cancer cells than for HER2 expressed on non-cancer cells, and more preferably, it is an isolated monoclonal antibody or antigen-binding fragment thereof that does not significantly react to HER2 expressed on non-cancer cells, but can specifically react to HER2 expressed on cancer cells, and that satisfies any one of the above (i) to (xiv).

In this embodiment, the antibody or antigen-binding fragment thereof of the present invention may have the profile of any one or more of the above (i) and (ii). More specifically, the antibody or antigen-binding fragment thereof of the present invention may have the profile of only the above (i), only the above (ii), or the above (i) and (ii).

In this embodiment, the antibody or antigen-binding fragment thereof of the present invention may satisfy the above (i) and one or more selected from the group consisting of the above (v), (vi), (ix), (x), (xi), (xii), (xiii), and (xiv). In this embodiment, the antibody or antigen-binding fragment thereof of the present invention may satisfy the above (ii) and one or more selected from the group consisting of the above (v), (vi), (ix), (x), (xi), (xii), (xiii), and (xiv). In this embodiment, the antibody or antigen-binding fragment thereof of the present invention may satisfy the above (i) and (ii) as well as one or more selected from the group consisting of the above (v), (vi), (ix), (x), (xi), (xii), (xiii), and (xiv). These antibodies or antigen-binding fragments thereof can bind to cancer cells with a stronger binding affinity (or reactivity) than to non-cancer cells. These antibodies or antigen-binding fragments thereof preferably do not significantly react to HER2 expressed on non-cancer cells, but can specifically react to HER2 expressed on cancer cells.

The antibody or antigen-binding fragment thereof of the present invention may be an antibody or antigen-binding fragment thereof that satisfies any one of the above (i) to (xiv).

In this embodiment, the antibody or antigen-binding fragment thereof of the present invention may have the profile of any one or more of the above (i) and (ii). More specifically, the antibody or antigen-binding fragment thereof of the present invention may have the profile of only the above (i), only the above (ii), or the above (i) and (ii). These antibodies or antigen-binding fragments thereof can bind to cancer cells with a stronger binding affinity (or reactivity) than to non-cancer cells. These antibodies or antigen-binding fragments thereof preferably do not significantly react to HER2 expressed on non-cancer cells, but can specifically react to HER2 expressed on cancer cells.

In this embodiment, the antibody or antigen-binding fragment thereof of the present invention may satisfy the above (i) and one or more selected from the group consisting of the above (v), (vi), (ix), (x), (xi), (xii), (xiii), and (xiv). In this embodiment, the antibody or antigen-binding fragment thereof of the present invention may satisfy the above (ii) and one or more selected from the group consisting of the above (v), (vi), (ix), (x), (xi), (xii), (xiii), and (xiv). In this embodiment, the antibody or antigen-binding fragment thereof of the present invention may satisfy the above (i) and (ii) as well as one or more selected from the group consisting of the above (v), (vi), (ix), (x), (xi), (xii), (xiii), and (xiv).

The antibody of the present invention may have antibody-dependent cellular cytotoxicity (ADCC) activity and/or complement-dependent cytotoxicity (CDC) activity. The ADCC activity means an activity in which, when the antibody of the present invention binds to a cell surface antigen of a target cell, an Fcγ receptor-bearing cell (effector cell) binds to an Fc portion thereof via an Fcγ receptor and damages the target cell.

The ADCC activity can be evaluated by mixing target cells expressing HER2 (cancer cells, for example, LN229 cells or SK-BR-3 cells), effector cells, and the antibody of the present invention, and measuring the degree of ADCC. As the effector cells, for example, mouse splenocytes, human peripheral blood, and monocyte nuclei separated from bone marrow can be used. As the target cell, for example, HER2-positive breast cancer cells can be used. Target cells are previously labeled with $^{51}$Cr or the like, and the antibody of the present invention is added thereto and incubated, and then effector cells (effector cells may be activated) are added at an appropriate ratio to the target cells and incubated. After the incubation, supernatant is collected, and the label in the supernatant is counted, whereby the measurement can be performed. The CDC activity means cytotoxic activity by the complement system. The CDC activity can be measured by using complement instead of effector cells in the test of ADCC activity.

The antibody of the present invention may be an antibody in which one or more N-linked sugar chains bind to an Fc region and fucose does not bind to N-acetylglucosamine at the reducing terminals of the N-linked glycans. For example, the Fc region of an IgG antibody has therein two binding sites of an N-linked sugar chain, to which sites a complex-type sugar chain has been bound. The term "N-linked sugar chain" means a sugar chain to be bound to Asn of an Asn-X-Ser/Thr sequence and has a common structure Man3GlcNAc2-Asn. It is classified into a high mannose type, a hybrid type, a complex type, or the like, depending on the kind of the sugar chain bound to two mannoses (Man) at the non-reducing terminal. Although fucose may be bound to N-acetylglucosamine (GlcNAc) at the reducing end of the N-linked sugar chain, it is known that an ADCC activity shows a remarkable increase when fucose is not bound thereto compared with when fucose is bound thereto. This is described, for example, in the pamphlet of WO 2002/031140, the disclosure of which is incorporated herein by reference in its entirety. Since a remarkable improvement in the ADCC activity may lead to a reduction of a dose of an antibody when it is used as a drug, adverse side effects can be alleviated and at the same time, medical expenses can be reduced. For enhancing the ADCC activity, the subtype of the human antibody used for the constant region can be IgG1.

<Antibody-Drug Conjugate>

According to the present invention, a conjugate of a drug and an antibody or antigen-binding fragment thereof of the present invention (antibody-drug conjugate; ADC) is provided. In the ADC of the present invention, the antibody or antigen-binding fragment thereof, and the drug (for example, a component having a property of damaging a cell, for example, a cytotoxic agent) may be linked via a linker. In the ADC of the present invention, examples of the cytotoxic agent include chemotherapeutic agents (for example, anticancer agents such as commercially available anticancer agents, for example, auristatin (auristatin E, auristatin F phenylenediamine (AFP), monomethylauristatin E, monomethylauristatin F and their derivatives), maytansinoid DM1, DM4, and their derivatives), camptothecin (SN-38, topotecan, exotecan, and their derivatives), DNA minor groove binder (enediyne, lexitropsin, duocarmycin, and their derivatives), taxanes (paclitaxel and docetaxel and their derivatives), polyketides (discodermolide and its derivatives), anthraquinones (mitoxantrone and its derivatives), benzodiazepines (pyrrolobenzodiazepine, indolinobenzodiazepine, and oxazolidinobenzodiazepine and their derivatives), vinca alkaloids (vincristine, vinblastine, vindesine, and vinorelbine and their derivatives), doxorubicins (doxorubicin, morpholino-doxorubicin, and cyanomorpholino-doxorubicin and their derivatives), Cardiac glycosides (digitoxin and its derivatives), calekiamycin, epothilone, cryptophycin, semadotin, rhizoxin, netropsin, combretastatin, eleutherobin, etoposide, T67 (churalic) and nocodazole), radioisotopes (for example, $^{32}$P, $^{60}$C, $^{90}$Y, $^{111}$In, $^{131}$J, $^{125}$J, $^{153}$Sm, $^{186}$Re, $^{188}$Re, and $^{212}$Bi), and toxins (e.g., diphtheria toxin A, Pseudomonas endotoxin, ricin, saporin and the like). These can be used as cytotoxic agents in the ADC of the present invention. Any of the cytotoxic agents can be used for treating cancer.

The antibody is desirably an antibody that is internalized in a cancer cell, but an antibody that is not internalized can also be used. This is because cancer can be killed by the bystander effect as long as an anticancer agent is delivered to the tissue surrounding the cancer.

In a certain embodiment of the present invention, the linker may be a non-cleavable linker or a cleavable linker. The bond between the antibody and the linker can be achieved by, for example, a sulfhydryl group of the antibody via a maleimide group. The linker may include a polyethylene glycol block as required.

Examples of the cleavable linker include peptide linkers such as a valine-citrulline (Val-Cit) linker and a phenylalanine-lysine (Phe-lys) linker, as well as hydrazone linkers that cleave in a pH-dependent manner. Examples of the cleavable linker also include linkers including a carbamate linkage or an ester linkage, which can be enzymatically degraded inside cells. These linkers may be used in combination.

In a certain embodiment of the present invention, the antibody and the cytotoxic agent can be linked by a maleimide group-PEG-Val-Cit. In a certain embodiment of the present invention, a linker (for example, the maleimide group-PEG-Val-Cit-PABA-cytotoxic agent) used in Examples of the present application can be used.

A spacer may be interposed between the linker and the cytotoxic agent.

<Method for Producing Antibody of the Present Invention>

The antibody of the present invention can be obtained by administering, to an animal, (i) a peptide as an immunogen including one or more amino acid sequences selected from the group consisting of the amino acid sequences of SEQ ID NOs: 31 to 37 (for example, the amino acid sequences of SEQ ID NOs: 31 to 36). In a certain embodiment, the antibody of the present invention may be obtained by administering a peptide consisting of the amino acid sequence of SEQ ID NO: 31 as an immunogen to an animal. In a certain embodiment, the antibody of the present invention may be obtained by administering a peptide consisting of the amino acid sequence of SEQ ID NO: 32 as an immunogen to an animal. In a certain embodiment, the antibody of the present invention may be obtained by administering a peptide consisting of the amino acid sequence of SEQ ID NO: 33 as an immunogen to an animal. In a certain embodiment, the antibody of the present invention may be obtained by administering a peptide consisting of the amino acid sequence of SEQ ID NO: 34 as an immunogen to an animal. In a certain embodiment, the antibody of the present invention may be obtained by administering a peptide consisting of the amino acid sequence of SEQ ID NO: 35 as an immunogen to an animal. In a certain embodiment, the antibody of the present invention may be obtained by administering a peptide consisting of the amino acid sequence of SEQ ID NO: 36 as an immunogen to an animal. In addition, the antibody of the present invention may be obtained by administering a peptide consisting of the amino acid sequence of SEQ ID NO: 37 as an immunogen to an animal. The peptide may be a synthetic peptide.

The antibody of the present invention may also be obtained by administering an extracellular domain portion of HER2, such as HER2ec, as an immunogen to an animal. The antibody of the present invention may also be obtained by methods well known to those skilled in the art, such as phage display. The extracellular domain portion of HER2 may be a synthetic peptide. The extracellular domain portion of HER2 may be obtained by expression in a cell, e.g., a non-cancer cell or a cancer cell, e.g., a cancer cell line (For example, LN229 cells).

Immunizing an animal with an immunogen can be performed by methods well known to those skilled in the art. Whether or not an antibody against HER2 or a partial peptide thereof has been produced can be confirmed, for example, by using a body fluid (for example, blood, plasma, or serum) or immune cells (for example, spleen cells) obtained from an immunized animal. The monoclonal antibody can be produced by a person skilled in the art using a well-known method such as a hybridoma method. Hybridomas can be produced by methods well known to those skilled in the art. After generation, the hybridoma is made into a single clone by ultradilution. The monoclonal antibody may be secreted into the hybridoma supernatant. Whether the monoclonal antibody has a desired binding property can be confirmed by a person skilled in the art by a binding assay (binding test).

For example, a person skilled in the art can easily test whether or not an antibody binds to a cancer cell with a stronger binding affinity than to a non-cancer cell, that is, whether or not the antibody does not significantly react to HER2 expressed on a non-cancer cell but can specifically react to HER2 expressed on a cancer cell. The test may preferably be an in vitro test. For the test, for example, a cancer cell line, particularly a HER2-positive cancer cell line (for example, SK-BR-3 cells), can be used as the cancer cells. The test may also employ, for example, a non-cancer cell line or a normal cell line, in particular an HER2-positive non-cancer cell line or normal cell line (For example, HaCaT cells), as non-cancer cells. For example, cells can be subjected to unicellularization and analyzed for interaction with the labeled antibody by flow cytometry to determine whether they bind to cancer cells with a stronger binding affinity than to non-cancer cells. As to labeling, a label well known to those skilled in the art such as a fluorescent label can be used. The binding reactivity to HER2-expressing cancer cells can be 1.5 times or more, 2 times or more, 3 times or more, 4 times or more, 5 times or more, 6 times or more, 7 times or more, 8 times or more, 9 times or more, 10 times or more, 100 times or more, 1,000 times or more, 10,000 times or more, or 100,000 times or more stronger than the binding affinity to any of the HER2-expressing normal cells, in terms of the binding reactivity (the amount of reacted antibody). The strength of binding reactivity may be a statistically significant difference (for example, $p<0.05$, $p<0.01$, $p<0.005$, or $p<0.0001$). The binding reactivity to cancer cells can be assessed using, for example, flow cytometry. When the binding affinity or reactivity is determined by flow cytometry, for example, peak values can be compared. That an antibody shows no significant binding to non-cancer cells (for example, normal cells) can be determined by testing whether the antibody shows significant binding to a non-cancer cell line (for example, a normal cell line, in particular an HER2-positive non-cancer cell line or normal cell line (for example, HaCaT cells)).

For example, whether or not the antibody or antigen-binding fragment thereof of the present invention satisfies the above (i) can be tested by an assay on whether or not a hybridoma supernatant and each of the peptides having any amino acid sequence selected from the group consisting of the amino acid sequences of SEQ ID NOs: 31 to 37 (for example, the amino acid sequences of SEQ ID NOs: 31 to 36) bind to each other. For example, the peptide is immobilized by a conventional method, whether the antibody in the hybridoma supernatant binds to this peptide is assayed, and the antibody produced by the hybridoma can be detected using a labeled secondary antibody that specifically reacts to the same. Surface plasmon resonance (SPR) may be used for detection. Similarly, whether or not the antibody or antigen-binding fragment thereof of the present invention satisfies the above (ii) can be determined by the following testing: testing, by an assay, whether or not the antibody in the hybridoma supernatant binds to a peptide having one or more amino acid mutations selected from the group consisting of W614A, K615A, and F616A (for example, variants of the extracellular domain of HER2 with a point mutation consisting of W614A; a variant of the extracellular domain of HER2 with a mutation consisting of two point mutations of K615A and F616A; a mutant of the extracellular domain of HER2 having a point mutation consisting of K615A; a mutant of the extracellular domain of HER2 having a point mutation consisting of F616A, or a mutant of the extracellular domain of HER2 having a mutation consisting of two point mutations of W614A and F616A) in the peptide consisting of a part (a region of amino acid numbers 603 to 622) of the extracellular domain of HER2 set forth in SEQ ID NOs: 2; and by testing, by an assay, whether or not the antibody in the hybridoma supernatant binds to the peptide consisting of the extracellular domain of HER2 set forth in SEQ ID NO: 3. For example, the binding dissociation constant ($K_D$) can be determined using surface plasmon resonance (SPR), and whether or not the above (ii) is satisfied can be easily determined using the magnitude of $K_D$ as an index. Therefore, according to the present invention, there can be provided a method for selecting or identifying an antibody or antigen-binding fragment thereof, the method including selecting or identifying an antibody or antigen-binding fragment thereof satisfying the above (i) from a group of antibodies or antigen-binding fragments thereof, for example, a group of antibodies or antigen-binding fragments thereof that bind to HER2 or a fragment thereof. According to the present invention, there can be also provided a method for selecting or identifying an antibody or antigen-binding fragment thereof, the method including selecting or identifying an antibody or antigen-binding fragment thereof satisfying the above (ii), from a group of antibodies or antigen-binding fragments thereof, for example, a group of antibodies or antigen-binding fragments thereof that bind to HER2 or a fragment thereof. These methods may include further selecting or identifying an antibody or antigen-binding fragment thereof that has a stronger binding reactivity to HER2 expressed on cancer cells than for HER2 expressed on non-cancer cells, that is, an antibody or antigen-binding fragment thereof that does not significantly react to HER2 expressed on a non-cancer cell, but can specifically react to HER2 expressed on a cancer cell, from the group of the antibodies or antigen-binding fragments thereof selected or identified by these methods described above. In the above description, when a part of the extracellular domain of HER2 is a region of amino acid numbers 603 to 622 of the amino acid sequence set forth in SEQ ID NO: 2, an antibody or an antigen-binding fragment thereof can be tested by a similar assay using a variant having the above-described point mutations in the peptide.

The competition assay can verify that the antibodies compete in the binding to HER2 and that the antibodies have similar binding properties to each other. An antibody that competes with a certain antibody in the binding to an antigen (for example, HER2 or a fragment thereof) can be obtained by a competition assay or the like well known to those skilled in the art. When an antibody is capable of blocking the binding of the desired antibody in a competition assay, for example, at at least 20%, preferably at least 20 to 50%, further preferably at least 50%, more preferably 60% or more, more preferably 70% or more, more preferably 80% or more, and especially preferably 90% or more, these can be considered to be antibodies that compete for binding to the same antigen. The competing antibodies can be confirmed by cross-blocking assay, flow cytometry, fluorescence energy transfer assay (FRET) or fluorescent microvolume assay technology (FMAT (registered trademark)), or preferably competitive ELISA assay. In cross-blocking assay, an antigen is coated, for example, on a microtiter plate, where the presence of a candidate competitive antibody is added and incubated to form a bond between the antigen and the candidate antibody. Then, after labeling the desired antibody, it is further added to the well, incubated, and washed, and then, the binding amount of the desired antibody is quantified to determine whether or not the antibody has competed. If competing, there should be less label remaining in the well.

Generally, in competition assay, even if an antibody A dissociates the binding between an antibody B and an antigen, the antibody B does not necessarily dissociate the binding between the antibody A and the antigen. This can be easily understood considering the case where the antibody A exhibits extremely stronger binding to the antigen than the antibody B. In order to obtain an antibody having close binding characteristics, it is only required to confirm that the antibody A dissociates the binding between the antibody B and the antigen and the antibody B dissociates the binding between the antibody A and the antigen, and in the present specification, such a competitive state is referred to as "the antibody A and the antibody B compete with each other in the binding between the antibody A and the antigen".

Therefore, whether or not the antibody or antigen-binding fragment thereof of the present invention satisfies any one of the above (v), (vi), (ix), and (x) can be determined by confirming whether or not the antibody or antigen-binding fragment thereof of the present invention competes with the antibody of any one of the above (iii), (iv), (vii), (viii), and (xiii) in the binding to HER2 or a fragment thereof (such as a peptide including an epitope). Therefore, according to the present invention, there can be provided a method for selecting or identifying an antibody or antigen-binding fragment thereof, the method including selecting or identifying an antibody or antigen-binding fragment thereof that competes with any antibody of the above (iii), (iv), (vii), (viii), and (xiii) in the binding to HER2 or a fragment thereof (such as a peptide including an epitope), from the antibodies or antigen-binding fragments thereof binding to HER2 or a fragment thereof. This method may include further selecting or identifying an antibody or antigen-binding fragment thereof that has a stronger binding reactivity to HER2 expressed on cancer cells than for HER2 expressed on non-cancer cells, from the group of the antibodies or antigen-binding fragments thereof selected or identified by these methods described above. As the fragment of HER2, a peptide that includes any amino acid sequence selected from the group consisting of the amino acid sequences of SEQ ID NOs: 31 to 37 (for example, the amino acid sequences of SEQ ID NOs: 31 to 36) can be used. As the fragment of HER2, HER2ec can be used. As HER2, HER2 expressed on the LN229 cell membrane can be used. According to the present invention, in this way, the antibody or antigen-binding fragment thereof of the present invention can be obtained.

In this way, a monoclonal antibody having the binding characteristics of the antibody of the present invention can be selected and obtained. The amino acid sequence of the obtained monoclonal antibody can be determined after obtaining the antibody. For example, by extracting RNA from a hybridoma producing the monoclonal antibody and synthesizing cDNA thereby determining the sequence of cDNA encoding an immunoglobulin. the base sequence of the gene encoding the obtained monoclonal antibody can be determined. The amino acid sequence of the obtained monoclonal antibody can be determined from the base sequence. From the amino acid sequence of the monoclonal antibody, the amino acid sequences of the heavy chains CDR1 to CDR3 and the amino acid sequences of the light chains CDR 1 to CDR3 can be estimated. CDR estimation can be performed by, for example, the Kabat numbering system (Kabat E. A. et al., (1991) Sequences of proteins of immunological interest. NIH Publication 91-3242)), Chothia (Al-lazikani et al., (1997) J. Mol. Biol. 273: 927-948), Aho, IMGT, CCG, or the like, or a combination of these techniques. It is also a well-known fact that the estimated CDR regions can vary depending on the numbering system. In this way, an antibody having the amino acid sequences of the heavy chains CDR1 to CDR3 and the amino acid sequences of the light chains CDR1 to CDR3 can be designed or produced.

The antigen-binding fragment of the antibody can be produced by a method well known to those skilled in the art. For example, a Fab fragment can be produced by digesting an antibody with papain. For example, F(ab')$_2$ can be produced by digesting an antibody with pepsin. For example, Fab' can be produced by treating F(ab')$_2$ with a reducing agent. For example, scFv can be constructed in a variety of ways. For example, the C-terminal of the heavy chain variable region can be linked to the N-terminal of the light chain variable region. Typically, a linker (for example, (GGGGS)$_4$, SEQ ID NO: 38) is placed between the heavy and light chain variable regions. However, the order in which the chains may be linked can be reversed and the C-terminal of the light chain variable region can be linked to the N-terminus of the heavy chain variable region. Tags that facilitate detection or purification of the scFv (for example, a Myc tag, a His tag, or a FLAG tag) can be included.

According to the present invention, a method for producing an antibody or antigen-binding fragment thereof is provided. The production method of the present invention may include administering, to an animal, the following as an immunogen:

a peptide of HER2 (for example, a peptide consisting of any of the amino acid sequences of SEQ ID NOs: 31 to 37, for example, a peptide consisting of the amino acid sequences of SEQ ID NOs: 31 to 36, for example, a peptide consisting of the amino acid sequence set forth in SEQ ID NO: 31, for example, a peptide consisting of the amino acid sequence set forth in SEQ ID NO: 32, for example, a peptide consisting of the amino acid sequence set forth in SEQ ID NO: 33, for example, a peptide consisting of the amino acid sequence set forth in SEQ ID NO: 34, for example, a peptide consisting of the amino acid sequence set forth in SEQ ID NO: 35, for example, a peptide consisting of the amino acid sequence set forth in SEQ ID NO: 36, for example, a peptide consisting of the amino acid sequence set forth in SEQ ID NO: 37); or HER2 expressed on cancer cells (for example, the extracellular domain of HER2). The production method of the present invention may also include testing (or confirming) that the obtained antibody exhibits a stronger reactivity to HER2 expressed on cancer cells than to HER2 expressed on non-cancer cells. The production method of the present invention may also include testing (or confirming) that the obtained antibody does not significantly react to HER2 expressed on non-cancer cells, but can specifically react to HER2 expressed on cancer cells. The production method of the present invention may also include testing (or confirming) that the obtained antibody is an antibody of the present invention (has the binding characteristics of the antibody of the present invention). When it is confirmed that the obtained antibody exhibits a stronger reactivity to HER2 expressed on cancer cells than to HER2 expressed on non-cancer cells, does not significantly react to HER2 expressed on non-cancer cells, and can specifically react to HER2 expressed on cancer cells, and/or is the antibody of the present invention (has the binding characteristics of the antibody of the present invention), the antibody can be selected. Antibodies can be produced using recombinant antibody-producing cells (for example, CHO cells and the like) including nucleic acids encoding the antibody. In the production method of the present invention, the produced antibody can be purified when required.

According to the present invention, there is provided a method of selecting or identifying an antibody or an antigen-binding fragment of an antibody, the method including selecting or identifying an antibody or antigen-binding fragment thereof that does not significantly react to HER2 expressed on non-cancer cells, but has a specific reactivity to HER2 expressed on cancer cells, from the group of antibodies or antigen-binding fragments thereof that bind to HER2 (for example, HER2 expressed on LN229 cells, a peptide consisting of any of the amino acid sequences of SEQ ID NOs: 31 to 37, for example, a peptide consisting of the amino acid sequences of SEQ ID NOs: 31 to 36). In a certain embodiment, the group of antibodies or antigen-binding fragments thereof that bind to HER2 or a fragment thereof can bind to the HER2ec protein produced by LN229 cells. In a certain embodiment, the group of antibodies or antigen-binding fragments thereof binding to HER2 or a fragment thereof can bind to a peptide consisting of any or amino acid sequences of the amino acid sequences of SEQ ID NOs: 31 to 37 (for example, the amino acid sequences of SEQ ID NOs: 31 to 36).

According to the present invention, there is provided a method of selecting or identifying an antibody or an antigen-binding fragment of an antibody, the method including selecting or identifying an antibody or an antigen-binding fragment of an antibody that does not significantly react to HER2 expressed on non-cancer cells, but has a specific reactivity to HER2 expressed on cells of a cancer cell line (for example, LN229 cells), from any of the above-described antibodies or antigen-binding fragments of the antibodies.

For example, according to the present invention, there is provided a method of selecting or identifying an antibody or an antigen-binding fragment of an antibody, the method including selecting or identifying an antibody or antigen-binding fragment thereof that does not significantly react to HER2 expressed on non-cancer cells, but has a specific reactivity to HER2 expressed on cancer cells, from the group of antibodies or antigen-binding fragments thereof that can bind to HER2ec protein produced by LN229 cells.

According to the present invention, there is also provided a method of selecting or identifying an antibody or an antigen-binding fragment of an antibody, the method including selecting or identifying an antibody or antigen-binding fragment thereof that does not significantly react to HER2 expressed on non-cancer cells, but has a specific reactivity to HER2 expressed on cancer cells, from the group of antibodies or antigen-binding fragments thereof that can bind to a peptide including any amino acid sequence selected from the group consisting of the amino acid sequences of SEQ ID NOs: 31 to 37 (for example, the amino acid sequences of SEQ ID NOs: 31 to 36).

According to the present invention, there is also provided a method of selecting or identifying an antibody or an antigen-binding fragment of an antibody, the method including selecting or identifying an antibody or antigen-binding fragment thereof that does not significantly react to HER2 expressed on non-cancer cells, but has a specific reactivity to HER2 expressed on cancer cells, from the group of antibodies or the group of antigen-binding fragments of the antibodies that have a strong binding affinity (or reactivity) to a peptide consisting of a part (a region of amino acid numbers 603 to 622) of an extracellular domain of HER2 set forth in SEQ ID NO: 2 than to a variant of an extracellular domain of HER2 set forth in SEQ ID NO: 2 having one or more amino acid mutations selected from the group consisting of W614A, K615A and F616A in a peptide consisting of a part (a region of amino acid numbers 603 to 622) of the extracellular domain of HER2.

According to the present invention, there is also provided a method of selecting or identifying an antibody or an antigen-binding fragment of an antibody, the method including selecting or identifying an antibody or antigen-binding fragment thereof that does not significantly react to HER2 expressed on non-cancer cells, but has a specific reactivity to HER2 expressed on cancer cells, from the group of antibodies or the group of antigen-binding fragments of the antibodies that have a strong binding affinity (or reactivity) to a peptide consisting of a part (a region of amino acid numbers 603 to 622) of an extracellular domain of HER2 set forth in SEQ ID NO: 2 than to a peptide having a point mutation consisting of W614A, or to a peptide having a point mutation consisting of K615A or F616A, in the peptide consisting of the part of the extracellular domain of HER2 set forth in SEQ ID NO: 2 (the region of amino acid numbers 603 to 622).

According to the present invention, there is also provided a method of selecting or identifying an antibody or an antigen-binding fragment of an antibody, the method including selecting or identifying an antibody or antigen-binding fragment thereof that does not significantly react to HER2 expressed on non-cancer cells, but has a specific reactivity to HER2 expressed on cancer cells, from the group of antibodies or the group of antigen-binding fragments of the antibodies that have a strong binding affinity (or reactivity) to a peptide consisting of a part (a region of amino acid numbers 603 to 622) of an extracellular domain of HER2 set forth in SEQ ID NO: 2 than to a variant of the extracellular domain of HER2 having a point mutation consisting of F616A, or to a peptide having two point mutations of W614A and F616A, in the peptide consisting of the part of the extracellular domain of HER2 set forth in SEQ ID NO: 2 (the region of amino acid numbers 603 to 622).

The antibody or antigen-binding fragment thereof of the present invention can be obtained by selecting an antibody or antigen-binding fragment thereof that does not significantly react to HER2 expressed on a non-cancer cell, but has a specific reactivity to HER2 expressed on a cancer cell, from a group of antibodies or antigen-binding fragments thereof that have at least one or more (for example, several) amino acid mutations selected from the group consisting of substitutions, additions, insertions, and deletions in at least one CDR of any of (iii), (iv), and (xii). Therefore, according to the present invention, there is provided method of selecting or identifying an antibody or an antigen-binding fragment of an antibody, the method including selecting or identifying an antibody or antigen-binding fragment thereof that does not significantly react to HER2 expressed on a non-cancer cell, but has a specific reactivity to HER2 expressed on a cancer cell, from a group of antibodies or antigen-binding fragments thereof that have at least one or more (for example, several) amino acid mutations selected from the group consisting of substitutions, additions, insertions, and deletions in at least one CDR of any of (iii), (iv), and (xii).

The antibody or antigen-binding fragment thereof of the present invention can be obtained by selecting an antibody or antigen-binding fragment thereof that does not significantly react to HER2 expressed on a non-cancer cell, but has a specific reactivity to HER2 expressed on a cancer cell, from a group of antibodies or antigen-binding fragments thereof that have at least one or more (for example, several) amino acid mutations selected from the group consisting of substitutions, additions, insertions, and deletions in at least one variable region of any of (vii), (viii), and (xiii). Therefore, according to the present invention, there is provided method of selecting or identifying an antibody or an antigen-binding fragment of an antibody, the method including selecting or identifying an antibody or antigen-binding fragment thereof that does not significantly react to HER2 expressed on a non-cancer cell, but has a specific reactivity to HER2 expressed on a cancer cell, from a group of antibodies or antigen-binding fragments thereof that have at least one or more (for example, several) amino acid mutations selected from the group consisting of substitutions, additions, insertions, and deletions in at least one variable region of any of (vii), (viii), and (xiii).

In this way, the antibody or the antigen-binding fragment of the antibody of the present invention can be selected or identified. After the antibody or the antigen-binding fragment of the antibody of the present invention is selected or identified, genes encoding them can be introduced into antibody-producing cells (for example, CHO cells and the like) to recover the antibody or the antigen-binding fragment of the antibody from the antibody-producing cells. The antibody or the antigen-binding fragment of the antibody of the present invention can be humanized as required. The antibody or the antigen-binding fragment of the antibody of the present invention can be isolated, for example, by using a protein A column or a protein G column. Furthermore, the isolated antibody or the isolated antigen-binding fragment of the antibody of the present invention may be mixed with a pharmaceutically acceptable excipient. Alternatively, the isolated antibody or the isolated antigen-binding fragment of the antibody of the present invention may be conjugated with a drug (for example, a cytotoxic agent). This allows the antibody or the antigen-binding fragment of the antibody of the present invention to target drugs to cancer cells expressing HER2.

According to the present invention, there can be provided a method for selecting or identifying an antibody or an antigen-binding fragment of an antibody, the method including:

selecting or identifying an antibody or an antigen-binding fragment of an antibody that does not significantly react to HER2 expressed on a non-cancer cell, but can have a specific reactivity to HER2 expressed on a cancer cell, from a group of antibodies or antigen-binding fragments of antibodies that can bind to HER2 (for example, HER2 expressed on an LN229 cell) or a fragment of HER2.

According to the present invention, there can be provided a method for selecting or identifying an antibody or an antigen-binding fragment of an antibody, the method including:

selecting or identifying an antibody or an antigen-binding fragment of an antibody that satisfies at least one selected from (i) or (ii) shown below, from a group of antibodies or antigen-binding fragments of antibodies that can bind to HER2 or a fragment thereof:

(i) binding to a peptide that includes any amino acid sequence selected from the group consisting of the amino acid sequences of SEQ ID NOs: 31 to 37 (for example, the amino acid sequences of SEQ ID NOs: 31 to 36); or (ii) having a stronger binding affinity (or reactivity) to a peptide consisting of an extracellular domain of HER2 set forth in SEQ ID NO: 3 than to a variant of an extracellular domain of HER2 set forth in SEQ ID NO: 2 having one or more amino acid mutations selected from the group consisting of W614A, K615A, and F616A in a peptide consisting of a part (a region of amino acid numbers 603 to 622) of the extracellular domain of HER2; or having a stronger reactivity to a peptide consisting of an extracellular domain of HER2 set forth in SEQ ID NO: 3 than to a peptide having a point mutation consisting of W614A, or a peptide having a point mutation of K615A or F616A, in a peptide consisting of a part (a region of amino acid numbers 603 to 622) of an extracellular domain of HER2 set forth in SEQ ID NO: 2.

According to the present invention, there is further provided a method for selecting or identifying an antibody or an antigen-binding fragment of an antibody, the method including:

selecting or identifying an antibody or antigen-binding fragment thereof that binds to HER2 or a fragment thereof, from a group of antibodies that satisfies at least one selected from (i) or (ii) shown below or from a group of antigen-binding fragments thereof that satisfies at least one selected from (i) or (ii) shown below:

(i) binding to a peptide that includes any amino acid sequence selected from the group consisting of the amino acid sequences of SEQ ID NOs: 31 to 37 (for example, the amino acid sequences of SEQ ID NOs: 31 to 36); or (ii) having a stronger binding affinity (or reactivity) to a peptide consisting of an extracellular domain of HER2 set forth in SEQ ID NO: 3 than to a variant of an extracellular domain of HER2 set forth in SEQ ID NO: 2 having one or more amino acid mutations selected from the group consisting of W614A, K615A, and F616A in a peptide consisting of a part (a region of amino acid numbers 603 to 622) of the extracellular domain of HER2; or having a stronger reactivity to a peptide consisting of an extracellular domain of HER2 set forth in SEQ ID NO: 3 than to a peptide having a point mutation consisting of W614A, or a peptide having a point mutation of K615A or F616A, in a peptide consisting of a part (a region of amino acid numbers 603 to 622) of an extracellular domain of HER2 set forth in SEQ ID NO: 2.

In these embodiments, the present invention may further include selecting or identifying an antibody or an antigen-binding fragment of an antibody that does not significantly react to HER2 expressed on a non-cancer cell, but has a specific reactivity to HER2 expressed on a cancer cell, from a group of obtained antibodies or a group of antigen-binding fragments of the obtained antibodies.

According to the present invention, there is also provided a method for selecting or identifying an antibody or an antigen-binding fragment of an antibody, the method including:

selecting or identifying an antibody or an antigen-binding fragment of an antibody that does not significantly react to HER2 expressed on a non-cancer cell, but has a specific reactivity to HER2 expressed on a cancer cell, from a group of antibodies or antigen-binding fragments of antibodies that have at least one or more amino acid mutations selected from the group consisting of substitutions, additions, insertions, and deletions in at least one CDR of any of the above (iii) or (iv).

According to the present invention, there is also provided a method for selecting or identifying an antibody or an antigen-binding fragment of an antibody, the method including:

selecting or identifying an antibody or an antigen-binding fragment of an antibody that does not significantly react to HER2 expressed on a non-cancer cell, but has a specific reactivity to HER2 expressed on a cancer cell, from a group of antibodies or antigen-binding fragments of antibodies that have at least one or more amino acid mutations selected from the group consisting of substitutions, additions, insertions, and deletions in at least one variable region of any of the above (vii) or (viii).

According to the present invention, there is also provided a method for selecting or identifying an antibody or an antigen-binding fragment of an antibody, the method including:

selecting or identifying an antibody or an antigen-binding fragment of an antibody that does not significantly react to HER2 expressed on a non-cancer cell, but has a specific reactivity to HER2 expressed on a cancer cell, from a group of antibodies or antigen-binding fragments of antibodies that have at least one or more amino acid mutations selected from the group consisting of substitutions, additions, insertions, and deletions in at least one CDR or variable region of any of the above (xii) or (xiii).

The method for selecting or identifying the antibody or the antigen-binding fragment of the antibody of the present invention may be a method for selecting or identifying a humanized antibody or an antigen-binding fragment of a humanized antibody, or a human antibody or an antibody-binding fragment of a human antibody. The method for selecting or identifying the antibody or the antigen-binding fragment of the antibody of the present invention may be a method for selecting or identifying an isolated and/or purified antibody or an antigen-binding fragment of an isolated and/or purified antibody.

According to the present invention, there is provided a method for producing an antibody or an antigen-binding fragment of an antibody, including selecting or identifying the antibody or the antigen-binding fragment of the antibody of the present invention described above. In this production method, an antibody or an antigen-binding fragment of an antibody can be produced from an antibody-producing cell by introducing a gene encoding the antibody or the antigen-binding fragment into the antibody-producing cell. An antibody or an antigen-binding fragment of an antibody can be also humanized so as to be a humanized antibody or an antigen-binding fragment of a humanized antibody. An antibody or an antigen-binding of an antibody can be isolated and/or purified and used in applications. For example, an antibody or an antigen-binding fragment of an antibody may be mixed with a pharmaceutically acceptable excipient, formulated, and made into a pharmaceutical composition.

<Pharmaceutical Composition of the Present Invention>

According to the present invention, a pharmaceutical composition containing the antibody or antigen-binding fragment thereof of the present invention is provided. The pharmaceutical composition of the present invention may contain a pharmaceutically acceptable carrier or additive with the antibody or antigen-binding fragment thereof of the present invention. Examples of carriers and additives include, but are not limited to, pharmaceutically acceptable organic solvents such as water, saline, phosphate buffer, dextrose, glycerol, and ethanol, as well as collagen, polyvinyl alcohol, polyvinylpyrrolidone, carboxyvinyl polymer, sodium carboxymethylcellulose, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin, mannitol, sorbitol, lactose, surfactants, and the like.

According to the present invention, a pharmaceutical composition containing a HER2-targeting agent (also referred to as a HER2-targeting therapeutic agent) containing the antibody or antigen-binding fragment thereof of the present invention can be provided. The pharmaceutical composition of the present invention can be used for treating cancer.

According to the present invention, a targeting agent containing the antibody or antigen-binding fragment thereof of the present invention, and a pharmaceutical composition containing the targeting agent, are provided. For example, according to the present invention, a pharmaceutical composition containing an antibody-drug conjugate (ADC) of the antibody or antigen-binding fragment thereof of the present invention and a drug (for example, a cytotoxic agent) is provided. The pharmaceutical composition of the present invention can be used for treating cancer.

<Others>

According to the present invention, there is provided a method for detecting HER2-positive cancer cells in a cancer sample obtained from a subject, the method including bringing the cancer sample and the antibody or antibody or antigen-binding fragment thereof of the present invention into contact with each other. In this method, when HER2 in a biological sample and an anti-HER2 antibody or antigen-binding fragment thereof form a complex, it can be determined that HER2-positive cancer cells are detected. According to the present invention, there can also be provided a method for determining the efficacy of a HER2-targeting therapy with a HER2-targeting agent containing the antibody or antibody or antigen-binding fragment thereof of the present invention, the method including:

bringing a biological sample obtained from a subject into contact with an anti-HER2 antibody or an antigen-binding fragment thereof (preferably, the antibody of antigen-binding fragment thereof of the present invention); and determining that the HER2-targeting therapy is effective for the subject when HER2 in the biological sample and the anti-HER2 antibody or the antigen-binding fragment thereof form a complex. According to the present invention, there can also be provided a method for determining the efficacy of a HER2-targeting therapy with a HER2-targeting agent containing the antibody or antibody or antigen-binding fragment thereof of the present invention, the method including:

bringing a biological sample obtained from a subject into contact with an anti-HER2 antibody or an antigen-binding fragment thereof (preferably, the antibody of antigen-binding fragment thereof of the present invention) to cause HER2 in the biological sample and the anti-HER2 antibody or the antigen-binding fragment thereof to form a complex; and detecting the complex, wherein the detection of the complex indicates that the HER2-targeting therapy is effective for the subject. Here, when the biological sample is a biopsy, the complex formation can be detected based on the binding of the biological sample to the biopsy sample, and when the biological sample is a liquid sample, the complex formation can be determined by a method well known to those skilled in the art, such as ELISA. In this embodiment, the method may be an in vitro method. In this embodiment, the method is an industrially applicable method. In this embodiment, the method is capable of not including a step of diagnosis. According to the present invention, a diagnostic agent or a diagnostic kit including the HER2 antibody or antigen-binding fragment thereof of the present invention for use in the method can be provided. The HER2 antibody or antigen-binding fragment thereof of the present invention may be labeled to detect the HER2 antibody or antigen-binding fragment thereof of the present invention, or the HER2 antibody or antigen-binding fragment thereof of the present invention may be detected by a labeled secondary antibody that recognizes the HER2 antibody or antigen-binding fragment thereof of the present invention. Thus, the diagnostic kit may further include a labeled secondary antibody that recognizes the HER2 antibody or antigen-binding fragment thereof of the present invention. The label may be a label used in an enzyme labeling method such as alkaline phosphatase or horseradish peroxidase, and the presence of the label can be detected using a chromogenic substrate for these. Thus, the diagnostic kit may further include a chromogenic substrate.

According to the present invention, there may be provided a pharmaceutical composition containing an HER2-targeting agent containing the antibody or antigen-binding fragment thereof of the present invention for use in treating cancer in a subject for which HER2-targeting therapy has been determined to be effective by the method described above. According to the present invention, there may be provided a pharmaceutical composition containing an HER2-targeting agent containing the antibody or antigen-binding fragment thereof of the present invention for use in treating cancer in a subject having a HER2-positive tumor that is reactive to the antibody or antibody or antigen-binding fragment thereof of the present invention. The HER2-targeting agent of the present invention can be used in combination with another anticancer agent and the like.

According to the present invention, there may be provided a method for treating cancer in a subject, the method including administering, to the subject, a therapeutically effective amount of a HER2-targeting agent containing the antibody or antigen-binding fragment thereof of the present invention. According to the present invention, there may be also provided a HER2-targeting agent containing the antibody or antigen-binding fragment thereof of the present invention for treating cancer in a subject to a subject for use in treating cancer in the subject. According to the present invention, there may be further provided use of a HER2-targeting agent containing the antibody or antigen-binding fragment thereof of the present invention in the manufacture of a medicament for use in a method of treating cancer in a subject. In these embodiments, the subject may be a subject for which the HER2-targeting therapy has been determined to be effective by the method described above. The subject may also be a subject having a HER2-positive tumor that is reactive to the antibody or antibody or antigen-binding fragment thereof of the present invention. A therapeutically effective amount is an amount of a pharmaceutical component that provides a medically significant benefit.

According to the present invention, there may be provided a method for causing the antibody or antigen-binding fragment thereof to bind to cancer cells of a HER2-positive cancer in a subject having the cancer, the method including administering, to the subject, an effective amount of the antibody or antigen-binding fragment thereof of the present invention. According to the present invention, there may be provided a method for causing a HER2-targeting agent containing the antibody or antigen-binding fragment thereof to bind to cancer cells of a HER2-positive cancer in a subject having the cancer, the method including administering, to the subject, an effective amount of the HER2-targeting agent containing the antibody or antigen-binding fragment thereof of the present invention.

EXAMPLES

Examples are described below. As the reagents used in the following examples, specifically, the products described in the examples were used, but equivalent products of other manufacturers (Sigma-Aldrich, FUJIFILM Wako Pure Chemical Corporation, Nacalai Tesque, R & D Systems, USCN Life Science INC., etc.) can be substituted.

Example 1: Production of CasMab Anti-HER2 Antibodies (1) Cells

Figure 1B:
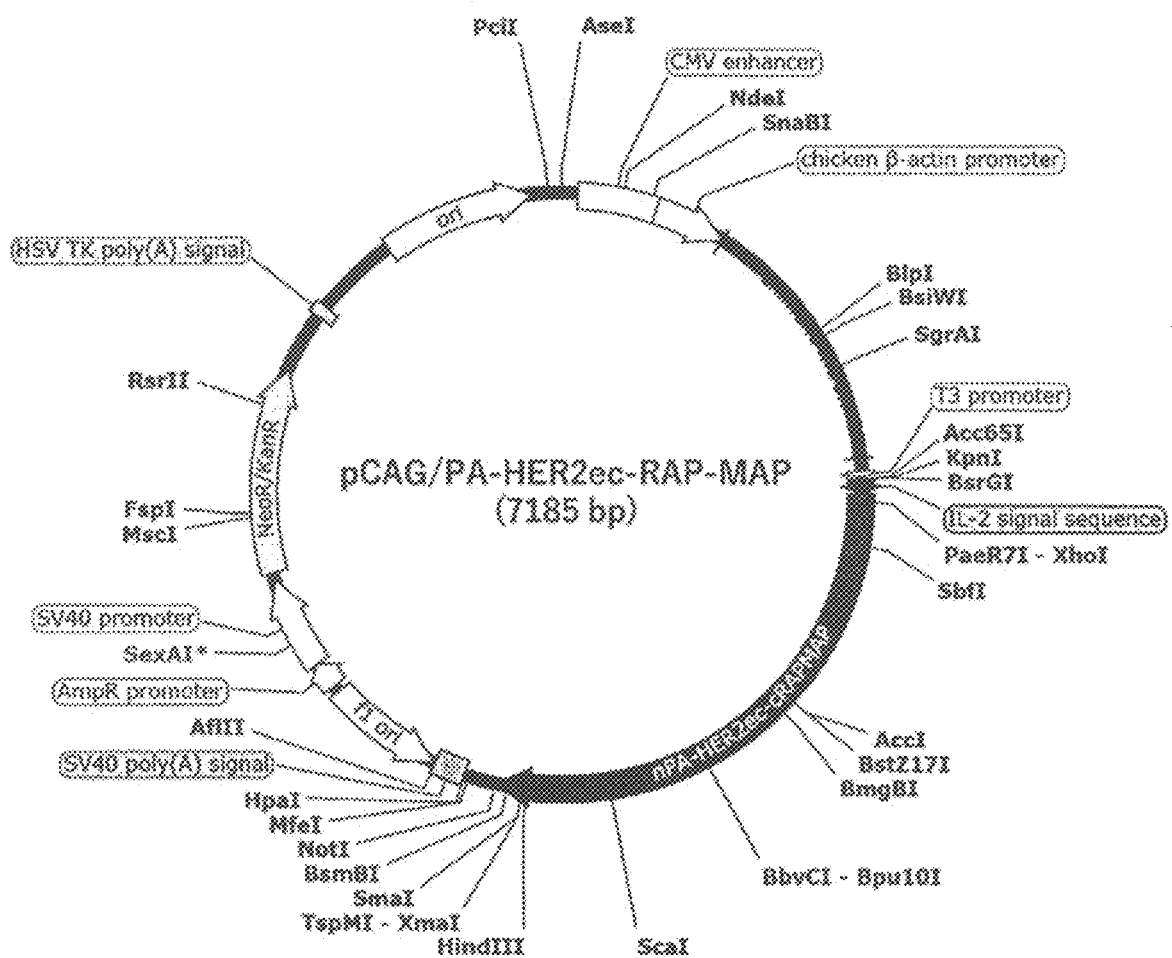
FIG. 1B is a vector map of pCAG/PA-HER2ec-RAP-MAP used in Examples.

The human glioblastoma cell line LN229, the human breast cancer cell line SK-BR-3, the Chinese Hamster Ovary (CHO)—K1 and the mouse myeloma cell line P3U1 were purchased from American Type Culture Collection (ATCC). The normal human epidermal keratinocyte cell line HaCaT was purchased from Cosmo Bio. As HER2, human HER2 having the amino acid sequence of SEQ ID NO: 2 was used. As HER2ec, an extracellular domain of human HER2 having the amino acid sequence of SEQ ID NO: 3 (secretory HER2) was used. An expression plasmid of a HER2 protein (pCAG/PA-HER2-RAP-MAP; Fujii et al., 2016, above; see FIG. 1A) obtained by adding a PA tag (Protein Expr Purif, 95, 240-247, 2014) to the N terminus, a RAP tag (Fujii et al., Monoclon. Antib. Immunodiagn. Immunother. April; 36 (2): 68-71, 2017) and a MAP tag (Fujii et al., Monoclon. Antib. Immunodiagn. Immunother., 35 (6), 293-299. 2016) to the C terminus, using Lipofectamine LTX (Thermo Fisher Scientific, Inc.) was transfected to CHO-K1. The HER2-expressing cells were sorted with an anti-PA tag antibody (Protein Expr Purif, 95, 240-247, 2014), and then a stably expressing cell line CHO/HER2 was established under drug selection. Using Neon transfection system (Thermo Fisher Scientific, Inc.), an expression plasmid (pCAG/PA-HER2-RAP-MAP or pCAG/PA-HER2ec-RAP-MAP) was introduced into LN229. The expression plasmids were an expression plasmid of HER2 protein (PA-HER2-RAP-MAP) in which a PA tag was added to the N terminus as well as a RAP tag and a MAP tag were added to the C terminus, and an expression plasmid of HER2ec (PA-HER2ec-RAP-MAP; Fujii et al. above, 2016; see FIG. 1B) in which a PA tag was added to the N terminus as well as a RAP tag and a MAP tag were added to the C terminus. PA-HER2-RAP-MAP-expressing cells were sorted with an anti-PA tag antibody, and then a stably expressing cell line LN229/HER2 was produced under drug selection. In addition, for the highly HER2ec expressing cell line, the culture supernatant was screened by sandwich ELISA of an antibody against RAP tag (PMab-2) and an antibody against PA tag (NZ-1) to produce LN229/HER2ec (secretory type). For CHO-K1, CHO/HER2, and P3U1, a RPMI 1640 medium (Nacalai Tesque, Inc.) was used as a basal medium. For LN229, LN229/HER2ec, LN229/HER2, SK-BR-3 and HaCaT, Dulbecco's Modified Eagle's Medium (Nacalai Tesque, Inc.) was used as a basal medium. 10% fetal bovine serum (Thermo Fisher Scientific, Inc.), penicillin (100 units/mL), streptomycin (100 units/mL) and amphotericin B (0.25 mg/mL) were added to the medium, and the mixture was cultured at 37° C., 5% $CO_2$.

(2) Generation of Monoclonal Antibodies

BALB/c mice (4 weeks old, female) used as immune animals were purchased from CLEA Japan. An antibody was produced using the CasMab method (Kato and Kaneko, Sci. Rep., 4: 5924, 2014). The HER2ec protein produced by LN229 cells was affinity-purified with an anti-MAP tag antibody (Fujii et al., 2016 above). Then, the BALB/c mice were initially immunized with 100 μg HER2ec protein mixed with Imject™ Alum (Thermo Fisher Scientific, Inc.). As additional immunization (3 times in total), 100 μg of HER2ec protein purified from LN229/HER2ec was intraperitoneally administered weekly. Thereafter, 100 μg of HER2ec was administered as the final immunization two days before the splenectomy. Splenocytes prepared from the excised spleen were cell fused with P3U1 using PEG 1500 (Roche Diagnostics). After cell fusion, cells were cultured in RPMI 1640 supplemented with hypoxanthine, aminopterin, and thymidine (Thermo Fisher Scientific, Inc.), and primary screening of the culture supernatant was performed by the below-described ELISA method using HER2ec. Hybridomas positive in the primary screening were cloned by limiting dilution. Monoclonal antibodies were prepared using a hybridoma supernatant cultured in a serum-free medium (Hybridoma-SFM; Thermo Fisher Scientific, Inc.) and purified using Protein G Sepharose 4 Fast Flow (GE Healthcare UK Ltd). Flow cytometry, Western blot, and immunohistochemistry staining were then performed as described below. As a result, from about 250 clones including the control antibody, the $H_2$Mab-119 antibody, a plurality of clones of cancer-specific antibodies considered to recognize cancer-specific HER2 were obtained through narrowing by flow cytometry, Western blot, and immunohistochemical staining. Hereinafter, the two clones were designated as $H_2$Mab-214 and $H_2$Mab-250 (hereinafter, the antibody may be collectively abbreviated as the antibody of the present invention), respectively. The antibodies obtained from the clone are referred to as a $H_2$Mab-214 antibody and a $H_2$Mab-250 antibody, respectively.

(3) ELISA

HER2ec (diluted with phosphate buffered saline (PBS)) was immobilized on a 96 well plate at a concentration of 1 μg/ml for 30 minutes at 37° C. Blocking was performed by reacting 1% bovine serum albumin (BSA)/0.05% Tween 20 in PBS (PBST) at 37° C. for 30 minutes. Thereafter, the culture supernatant was reacted at 37° C. for 30 minutes, and then washed 3 times using 0.05% PBST. Further, a secondary antibody (1/2000 dilution; Agilent Technologies, Inc.) was reacted at 37° C. for 30 minutes and washed 3 times using 0.05% PBST. Finally, color was developed by 1-Step Ultra TMB-ELISA (Thermo Fisher Scientific, Inc.), and absorbance was measured at an OD of 655 nm of a microplate reader.

(4) Flow Cytometry

Various adherent cells were collected using 0.25% trypsin/1 mM EDTA (Nacalai Tesque, Inc.), washed with 0.1% BSA/PBS, and then reacted at 4° C. with the antibody (1 μg/mL) prepared in the above (2). The cells were washed with 0.1% BSA/PBS, and then reacted with an Oregon green labeled anti-mouse IgG antibody (1000 fold dilution; Thermo Fisher Scientific, Inc.) for 30 minutes. The fluorescence intensity was measured with an EC800 cell Analyzer (Sony Corp.).

(5) Western Blot

A cell lysate prepared with an SDS sample buffer (Nacalai Tesque, Inc.) containing 2-mercaptoethanol was electrophoresed with a 5-20% polyacrylamide gel (FUJIFILM Wako Pure Chemical Corporation), and transferred onto a polyvinylidene fluoride (PVDF) film (Merck KGaA). The polyvinylidene fluoride PDVF film was blocked with 4% skim milk-added PBST, and then reacted with the antibody (5 µg/mL) prepared in the above (2) or the anti-b-actin antibody (clone AC-15; Sigma-Aldrich Corp.). Thereafter, the cells were reacted with a peroxidase-labeled anti-mouse IgG antibody (1000 dilution; Agilent Technologies, Inc.). For detection, a chemiluminescent reagent (ImmunoStar LD; FUJIFILM Wako Pure Chemical Corporation) was used, and a signal was detected with a Sayaca-Imager (DRC Corporation).

(6) Immunohistochemical Staining A breast cancer tissue (Catalog No.: B 904111) purchased from BioChain Institute, Inc. and a normal mammary gland tissue (Catalog No.: B 803077) purchased from BioChain Institute, Inc. were used. The tissue sections were deparaffinized and dehydrated with xylene, immersed in a citrate buffer (pH 6.0; Agilent Technologies, Inc.), and autoclaved for 20 minutes. Next, the tissue sections were reacted with the antibody (1 µg/mL) prepared in the above (2), at room temperature for 1 hour, and then treated with Envision+ kit, mouse (Agilent Technologies, Inc.) for 30 minutes. They were treated with 3,3'-diaminobenzidine tetrahydrochloride for 2 minutes to develop color, and counterstained with hematoxylin. Staining intensity was assessed with 0, 1+, 2+, and 3+ based on the 2018 ASCO/CAP guidelines described above.

Example 2: Sequencing of CasMab Anti-HER2 Antibodies (1) Determination of amino acid sequences and base sequences of $H_2$Mab-214 antibody and $H_2$Mab-250 antibody Total RNA was extracted from $H_2$Mab-214 and $H_2$Mab-250 hybridoma cells, $1 \times 10^6$, using RNeasy Plus mini kit (QIAGEN). cDNA synthesis was performed from 5 µg of total RNA, using SuperScript IV cDNA Syntheses System (Thermo Fisher Scientific, Inc.). cDNA was used as a template in the following experiments.

The following primers were used for amplification of the heavy chain (H chain).

InF.HindIII-H2-214H (SEQ ID NO: 4)

InF.HindIII-H2-250H (SEQ ID NO: 5)

InFr.IgG1 terNotI (SEQ ID NO: 6)

HotStar HiFidelity DNA polymerase (QIAGEN) was used for the PCR reaction.

Regarding the temperature conditions, a cycle of, first, 95° C. for 5 minutes, then 94° C. for 15 seconds, 50° C. for 1 minute, and 72° C. for 1 minute was repeated 35 times, followed by 72° C. for 10 minutes finally. The amplified PCR product was purified by FastGene Gel/PCR Extraction (Nippon Genetics Co., Ltd.).

The PCR product of the $H_2$Mab-214 antibody H chain was subcloned into a pCAG vector, which had been treated with the restriction enzymes HindIII and NotI at 37° C. for 1 hour and purified by FastGene Gel/PCR Extraction kit (Nippon Genetics Co., Ltd.), using InFusion-HD cloning kit (Takara Bio Inc.), and the base sequence was confirmed from the vector primer.

The PCR product of the $H_2$Mab-250 antibody H chain was subcloned into a pCAG vector, which had been treated with the restriction enzymes HindIII and NotI at 37° C. for 1 hour and purified by FastGene Gel/PCR Extraction kit (Nippon Genetics Co., Ltd.), using InFusion-HD cloning kit (Takara Bio Inc.), and the base sequence was confirmed from the vector primer.

The following primers were used for amplification of the light chain (L chain).

InF.HindIII-H2-214L (SEQ ID NO: 7)

InF.HindIII-H2-250L (SEQ ID NO: 8)

InF.mIgCKterNotI (SEQ ID NO: 9)

HotStar HiFidelity DNA polymerase (QIAGEN) was used for the PCR reaction. Regarding the temperature conditions, a cycle of, first, 95° C. for 5 minutes, then 94° C. for 15 seconds, 50° C. for 1 minute, and 72° C. for 1 minute was repeated 35 times, followed by 72° C. for 10 minutes finally. The amplified PCR product was purified by FastGene Gel/PCR Extraction (Nippon Genetics Co., Ltd.).

The PCR product of the $H_2$Mab-214 antibody L chain was subcloned into a pCAG vector, which had been treated with the restriction enzymes HindIII and NotI at 37° C. for 1 hour and purified by FastGene Gel/PCR Extraction kit (Nippon Genetics Co., Ltd.), using InFusion-HD cloning kit (Takara Bio Inc.), and the base sequence was confirmed from the vector primer.

The PCR product of the $H_2$Mab-250 antibody L chain was subcloned into a pCAG vector, which had been treated with the restriction enzymes HindIII and NotI at 37° C. for 1 hour and purified by FastGene Gel/PCR Extraction kit (Nippon Genetics Co., Ltd.), using InFusion-HD cloning kit (Takara Bio Inc.), and the base sequence was confirmed from the vector primer.

As a result, the base sequence of the DNA encoding the H chain of the $H_2$Mab-214 antibody was as shown in SEQ ID NO: 10, and the base sequence of the DNA encoding the L chain of the $H_2$Mab-214 antibody was as shown in SEQ ID NO: 11. Similarly, the base sequence of the DNA encoding the H chain of the $H_2$Mab-250 antibody was as shown in SEQ ID NO: 12, and the base sequence of the DNA encoding the L chain of the $H_2$Mab-250 antibody was as shown in SEQ ID NO: 13.

The amino acid sequence was predicted from each base sequence of the $H_2$Mab-214 antibody. The H-chain amino acid sequence of the $H_2$Mab-214 antibody was as shown in SEQ ID NO: 14, and the L-chain amino acid sequence of the $H_2$Mab-214 antibody was as shown in SEQ ID NO: 15. Similarly, the amino acid sequence was predicted from each base sequence of the $H_2$Mab-250 antibody. The H-chain amino acid sequence of the $H_2$Mab-250 antibody was as shown in SEQ ID NO: 16, and the L-chain amino acid sequence of the $H_2$Mab-250 antibody was as shown in SEQ ID NO: 17.

(2) Determination of CDRs (Complementarity Determining Regions) of $H_2$Mab-214 Antibody and $H_2$Mab-250 Antibody Based on the base sequences determined in the above (1), portions of CDRs were identified by an immunoglobulin predicting application provided at a website at the following URL (abYsis; http://www.abysis.org/abysis/index.html) (Kabat numbering).

As a result, the amino acid sequences of the heavy chain CDRs 1 to 3 and the light chain CDRs 1 to 3 of the $H_2$Mab-214 antibody were identified as shown in SEQ ID NOs: 18 to 20 and SEQ ID NOs: 21 to 23, respectively. Similarly, the amino acid sequences of the heavy chain CDRs 1 to 3 and the light chain CDRs 1 to 3 of the $H_2$Mab-250 antibody were identified as shown in SEQ ID NOs: 24 to 26 and SEQ ID NOs: 27 to 29, respectively.

Example 3: Assessment of CasMab Anti-HER2 Antibodies (1) Flow Cytometry

Flow cytometry analysis was performed on a normal human epidermal keratinocyte cell line HaCaT (Cosmo Bio) and a breast cancer cell line SK-BR-3 (ATCC) by the following method.

Various adherent cells were collected using 0.25% trypsin/1 mM EDTA (Nacalai Tesque, Inc.), washed with 0.1% BSA/PBS, and then reacted at 4° C. with various anti-HER2 monoclonal antibodies (control antibody ((H$_2$Mab-119 antibody; see Monoclon. Antib. Immunodiagn. Immunother., vol. 36 (6), 287-290, 2017), H$_2$Mab-214 antibody, and H$_2$Mab-250 antibody, each culture supernatant). The cells were washed with 0.1% BSA/PBS, and then reacted with an Oregon green labeled anti-mouse IgG antibody (1000 fold dilution; Thermo Fisher Scientific, Inc.) for 30 minutes. The fluorescence intensity was measured with an EC800 cell Analyzer (Sony Corp.).

Figure 2:
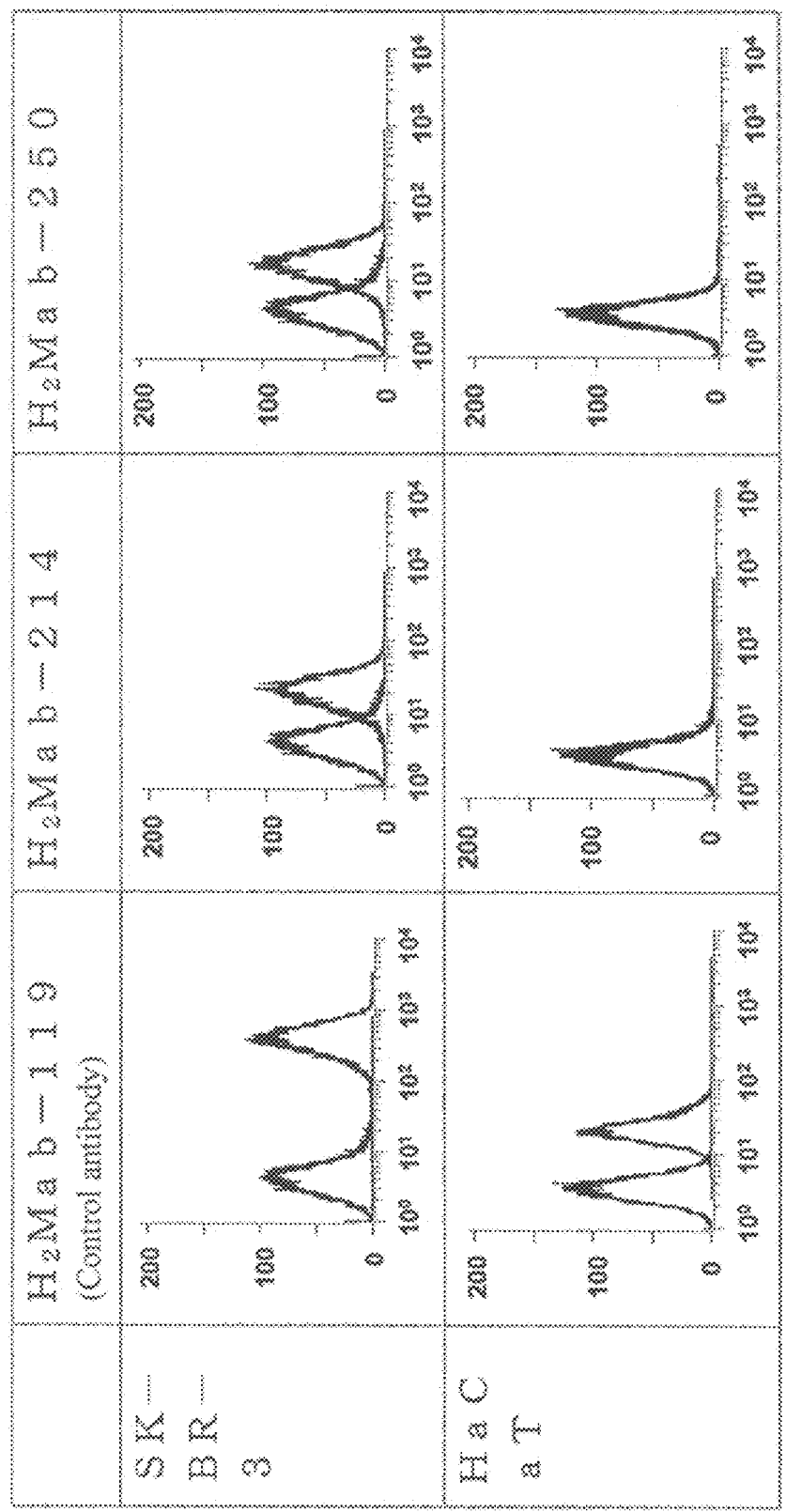
FIG. 2 shows that exemplary antibodies of the present invention (H$_2$Mab-214 and H$_2$Mab-250) bind to HER2 expressed on cells of a breast cancer cell line (SK-BR-3 cells), but does not react at all to HER2 expressed on cells of a normal human epidermal keratinocyte cell line (HaCaT cells).

As a result, as shown in FIG. 2, the control antibody (H$_2$Mab-119 antibody) not only reacted to the cancer cell line SK-BR-3, but also showed a moderate reactivity to the normal cell line HaCaT. On the other hand, the antibody of the present invention showed a moderate reactivity to the cancer cell line SK-BR-3, but did not react at all to the normal cell line HaCaT.

From this, it was shown that the antibody of the present invention has a cancer specificity.

(2) Immunohistochemical Staining

Immunohistochemical staining was performed on a HER2-negative breast cancer tissue microarray (catalog number: B904111) obtained from BioChain, Inc. by the following method.

The tissue sections were deparaffinized and dehydrated with xylene, immersed in a citrate buffer (pH 6.0; Agilent Technologies, Inc.), and autoclaved for 20 minutes. Next, the tissue sections were reacted with the antibody (1 μg/mL) of the present invention, at room temperature for 1 hour, and then treated with Envision+ kit, (Agilent Technologies, Inc.) for 30 minutes. They were treated with 3,3'-diaminobenzidine tetrahydrochloride for 2 minutes to develop color, and counterstained with hematoxylin. The staining intensity was assessed with 0, 1+, 2+, and 3+ as described above.

Figure 3:
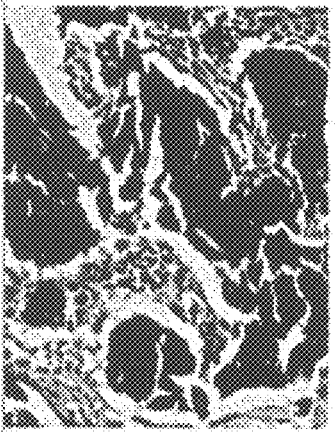
FIG. 3 shows results of immunohistochemistry (IHC) staining showing that the exemplary antibodies of the present invention (H$_2$Mab-214 and H$_2$Mab-250) stain cancer cells that have been diagnosed as HER2-negative by a conventional diagnostic agent for examining the HER2 expression status of cancer cells.

As a result, as shown in FIG. 3 below, the control antibody (H$_2$Mab-119 antibody) was negative for breast cancer (HER2-negative breast cancer) tissues determined to be HER2-negative by a diagnostic agent that examines the HER2 expression status of cancer cells using immunohistochemical staining (IHC). On the other hand, the antibodies of the present invention had cores showing positive images of 1+ to 3+ for HER2-negative breast cancer tissues. From this, it was found that the antibody of the present invention exhibits a high sensitivity in immunohistochemical staining.

Example 4: Epitope Analysis of CasMab Anti-HER2 Antibody (1)

The antibodies of the present invention reacted to all of the following mutants: deletion mutant produced by a conventional method (WT-dN23 (mutant of human HER2 (SEQ ID NO: 2) with deletion of a region from the N-terminus to amino acid number 22); dN200 (deletion mutant of human HER2 (SEQ ID NO: 2) with deletion of a region from the N-terminus to amino acid number 199); dN300 (deletion mutant of human HER2 (SEQ ID NO: 2) with deletion of a region from the N-terminus to amino acid number 299); dN400 (deletion mutant of human HER2 (SEQ ID NO: 2) with deletion of a region from the N-terminus to amino acid number 399); dN500 (deletion mutant of human HER2 (SEQ ID NO: 2) with deletion of a region from the N-terminus to amino acid number 499); and dN600 (deletion mutant of human HER2 (SEQ ID NO: 2) with deletion of a region from the N-terminus to amino acid number 599). It was therefore predicted that the antibody recognized the amino acid sequence of amino acid numbers 600-652 (SEQ ID NO: 30) of human HER2 (SEQ ID NO: 2). On the other hand, the control antibody (H$_2$Mab-119 antibody) reacted to WT-dN23 but not to dN200, dN300, dN400, dN500 and dN600. It was therefore expected that the antibody recognized the amino acid region up to amino acid numbers 23-199 of human HER2. The amino acid numbers in this example and the following examples are indicated as the positions of amino acids in the amino acid sequence of SEQ ID NO: 2.

Next, reactivities of the antibodies of the present invention to synthetic peptides consisting of the following amino acid regions of HER2ec(23-652) and HER2ec were confirmed by ELISA: 23-42, 33-52, 43-62, 53-72, 63-82, 73-92, 83-102, 93-112, 103-122, 113-132, 123-142, 133-152, 143-162, 153-172, 163-182, 173-192, 183-202, 193-212, 203-222, 213-232, 223-242, 233-252, 243-262, 253-272, 263-282, 273-292, 283-302, 293-312, 303-322, 313-332, 323-342, 333-352, 343-362, 353-372, 363-382, 373-392, 383-402, 393-412, 403-422, 413-432, 423-442, 433-452, 443-462, 453-472, 463-482, 473-492, 483-502, 493-512, 503-522, 513-532, 523-542, 533-552, 543-562, 553-572, 563-582, 573-592, 583-602, 593-612, 603-622, 613-632, 623-642, and 633-652 (here, the foregoing amino acid numbers indicate amino acid numbers in the amino acid sequence of SEQ ID NO: 2. That is, each peptide was immobilized on a 96 well plate at a concentration of 10 μg/ml for 30 minutes at 37° C. By causing 1% BSA/0.05% PBST to react with the same at 37° C. for 30 minutes, blocking was performed. Thereafter, 10 g/ml of each antibody of the present invention was reacted at 37° C. for 30 minutes, and then washed 3 times using 0.05% PBST. Further, a secondary antibody (1/2000 dilution; Agilent Technologies, Inc.) was reacted at 37° C. for 30 minutes and washed 3 times using 0.05% PBST. Finally, color was developed by 1-Step Ultra TMB-ELISA (Thermo Fisher Scientific, Inc.) for 15 minutes, and absorbance was measured at an OD of 655 nm of a microplate reader (Bio-Rad).

As a result, since the H$_2$Mab-214 antibody and the H$_2$Mab-250 antibody strongly reacted with peptides of 603 to 622 and peptides of 613 to 632, it was considered that the epitope of the antibody of the present invention was an amino acid region of 603-622 of human HER2 (SEQ ID NO: 31), an amino acid region of 613 to 632 of human HER2 (SEQ ID NO: 32), particularly an amino acid region of 613 to 622 (SEQ ID NO: 33).

Then, 20 types of mutated peptides were prepared by substituting 20 amino acids of the 603 to 622 peptides of human HER2 with alanine, respectively, and reactivities of the antibodies of the present invention to the 20 types of mutated peptides were confirmed by the ELISA method, with HER2ec being used as a positive control.

As a result, the reactivities of the H$_2$Mab-214 antibody to the K615A peptide and the F616A peptide obtained by substituting K615 and F616 in the amino acids of 603 to 622 of human HER2 with alanine, respectively, were weaker than the reactivities thereof to the wild-type HER2 peptide (603 to 622 amino acids of human HER2), and thus it was found that the two amino acids of K615 and F616 and their surroundings were epitopes of the H$_2$Mab-214 antibody.

In addition the reactivity of the H$_2$Mab-250 antibody to the W614A peptide obtained by substituting W614 in human HER2 with alanine was weaker than the reactivity thereof to the wild-type HER2 peptide, and thus it was found that the amino acid of W614 and surroundings thereof were an epitope of the H$_2$Mab-250 antibody.

Figure 4:
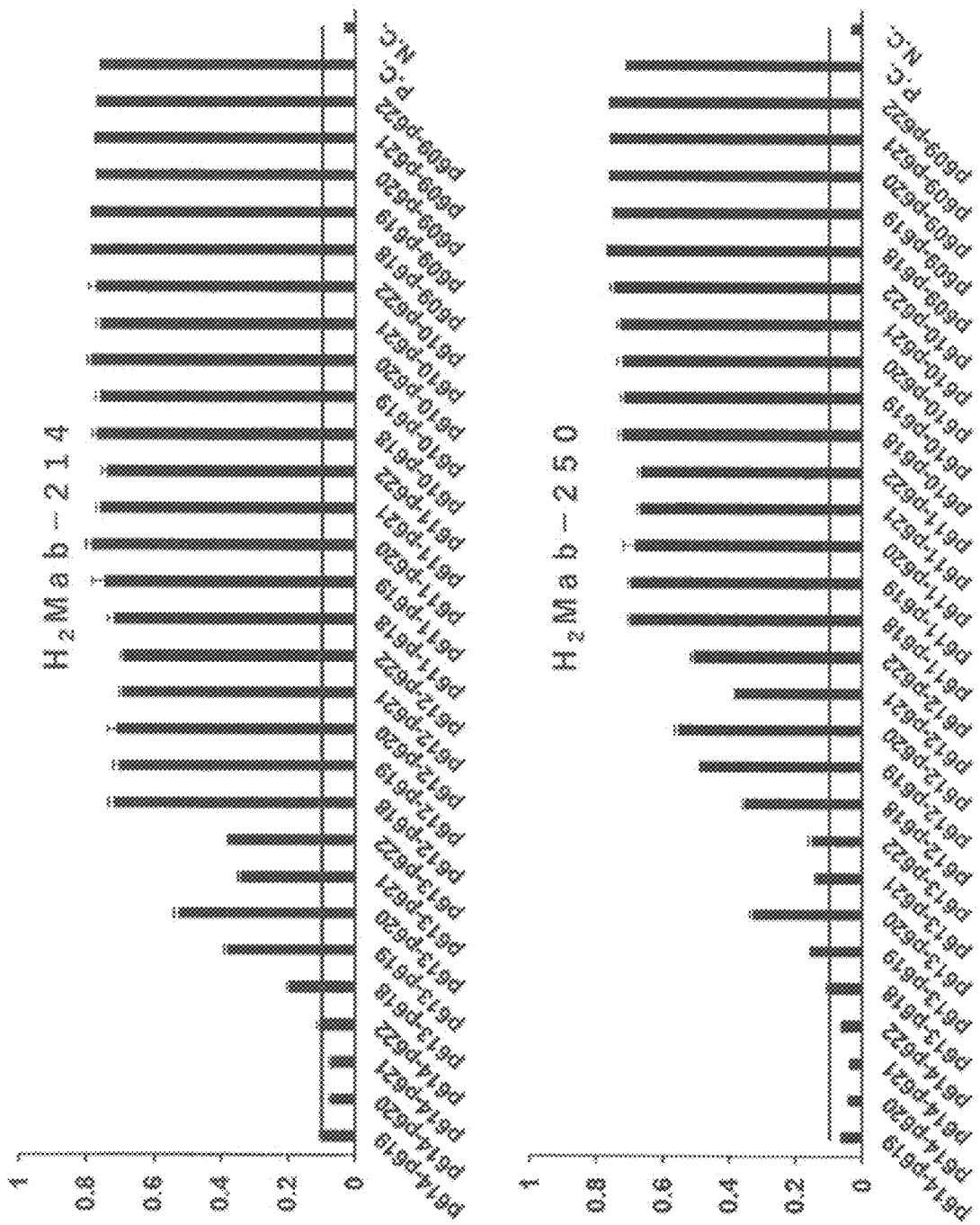
FIG. 4 shows binding of H$_2$Mab-214 and H$_2$Mab-250 to various partial peptides of HER2.

Epitopes of the H$_2$Mab-214 antibody and the H$_2$Mab-250 antibody were examined in more detail. Reactivities of the antibodies of the present invention to synthetic peptides (various deletion mutants) consisting of the following amino acid regions of human HER2 were confirmed by ELISA: 614-619, 614-620, 614-621, 614-622, 613-618, 613-619, 613-620, 613-621, 613-622, 612-618, 612-619, 612-620, 612-621, 612-622, 611-618, 611-619, 611-620, 611-621, 611-622, 610-618, 610-619, 610-620, 610-621, 610-622, 609-618, 609-619, 609-620, 609-621, and 609-622 (here, the foregoing amino acid numbers indicates amino acid numbers in the amino acid sequence of SEQ ID NO. 2). ELISA was performed in the same manner as described above. As the primary antibody, each antibody of the present invention was used at 50 µL/well, and as the secondary antibody, rabbit anti-mouse IgG/HRP (Agilent Technologies, Inc., 1% BSA/PBS-T, 1/2,000 dilution, 50 µL/well) was used. For detection, ELISA POD substrate TMB kit (Nacalai Tesque, Inc.) was used. Absorbance at an OD of 655 nm was measured using iMark Microplate Reader. The results were as shown in FIG. 4. In FIG. 4, the amino acid number is preceded by "p". In FIG. 4, P.C. represents a positive control, and N.C. represents a negative control.

As shown in FIG. 4, the H$_2$Mab-214 antibody showed a strong reactivity to a peptide composed of an amino acid region of 612 to 618 (SEQ ID NO: 35), and showed a reactivity equivalent to that of a longer peptide including an amino acid region of 612 to 618. As shown in FIG. 4, the H$_2$Mab-250 antibody showed a strong reactivity to a peptide composed of an amino acid region of 611 to 618 (SEQ ID NO: 34), and showed a reactivity equivalent to that of a longer peptide including an amino acid region of 611 to 618.

Furthermore, as shown in FIG. 4, when those having an OD value of more than 0.1 were evaluated as reactive, both the H$_2$Mab-214 antibody and the H$_2$Mab-250 antibody showed a reactivity to a peptide composed of an amino acid region of 613 to 619 (SEQ ID NO: 36). However, since the reactivity was weaker than the reactivity to the peptide consisting of an amino acid region of 612 to 618 (SEQ ID NO: 35) or the peptide consisting of an amino acid region of 611 to 618 (SEQ ID NO: 34), it was revealed that the reactivity of the antibody of the present invention to a partial peptide of HER2 was strongly affected by the 612th amino acid (and/or the 611th amino acid).

Example 5: Epitope Analysis of CasMab Anti-HER2 Antibody (2)

(1) Flow Cytometry

Epitope analysis of the H$_2$Mab-214 antibody or the H$_2$Mab-250 antibody was performed by flow cytometry (FACS) analysis using alanine-substituted variants. The HER2 (human HER2 having the amino acid sequence of SEQ ID NO: 2) gene in which the amino acid at the target position was substituted with alanine was produced using QuikChange Lightning Site-Directed Mutagenesis Kit (Agilent Technologies, Inc.), and the introduction of mutation was confirmed by determining the base sequence. The HER2 gene including the intended alanine substitution mutation was incorporated into an expression vector by adding a PA tag at the N-terminus, as well as a RAP tag and a MAP tag at the C-terminus, similarly to the wild-type HER2 gene (see Example 1). This plasmid was transferred to CHO-K1 cells using Neon Transfection system (Thermo Fisher Scientific, Inc.), followed by cell sorting with an anti-PA antibody (Cell Sorter SA3800, Sony Corp.), and then, drug selection with Zeocin (0.5 mg/mL, InVivogen), whereby a stably expressing cell line was established.

CHO-K1 cells forcibly and stably expressing the HER2 gene in which the amino acid at the target position was substituted with alanine were collected from a culture dish using a 0.25% trypsin/1 mM EDTA solution (Nacalai Tesque, Inc.) and washed with 0.1% BSA (Nacalai Tesque, Inc.)/PBS. A primary antibody (H$_2$Mab-214 antibody or H$_2$Mab-250 antibody) was adjusted to 10 µg/mL with 0.1% BSA/PBS, added to the collected cells, mixed, and reacted on ice for 30 minutes. Thereafter, the cells were washed with 0.1% BSA/PBS. Subsequently, a fluorescently-labeled secondary antibody (1/1000 dilution, anti-Mouse IgG Alexa Fluor 488, Thermo Fisher Scientific, Inc.) was adjusted with 0.1% BSA/PBS, and reacted on ice for 30 minutes. Thereafter, the cells were again washed with 0.1% BSA/PBS. Reactivity of the antibody was detected with a cell analyzer EC800 (Sony Corp.).

Figure 5:
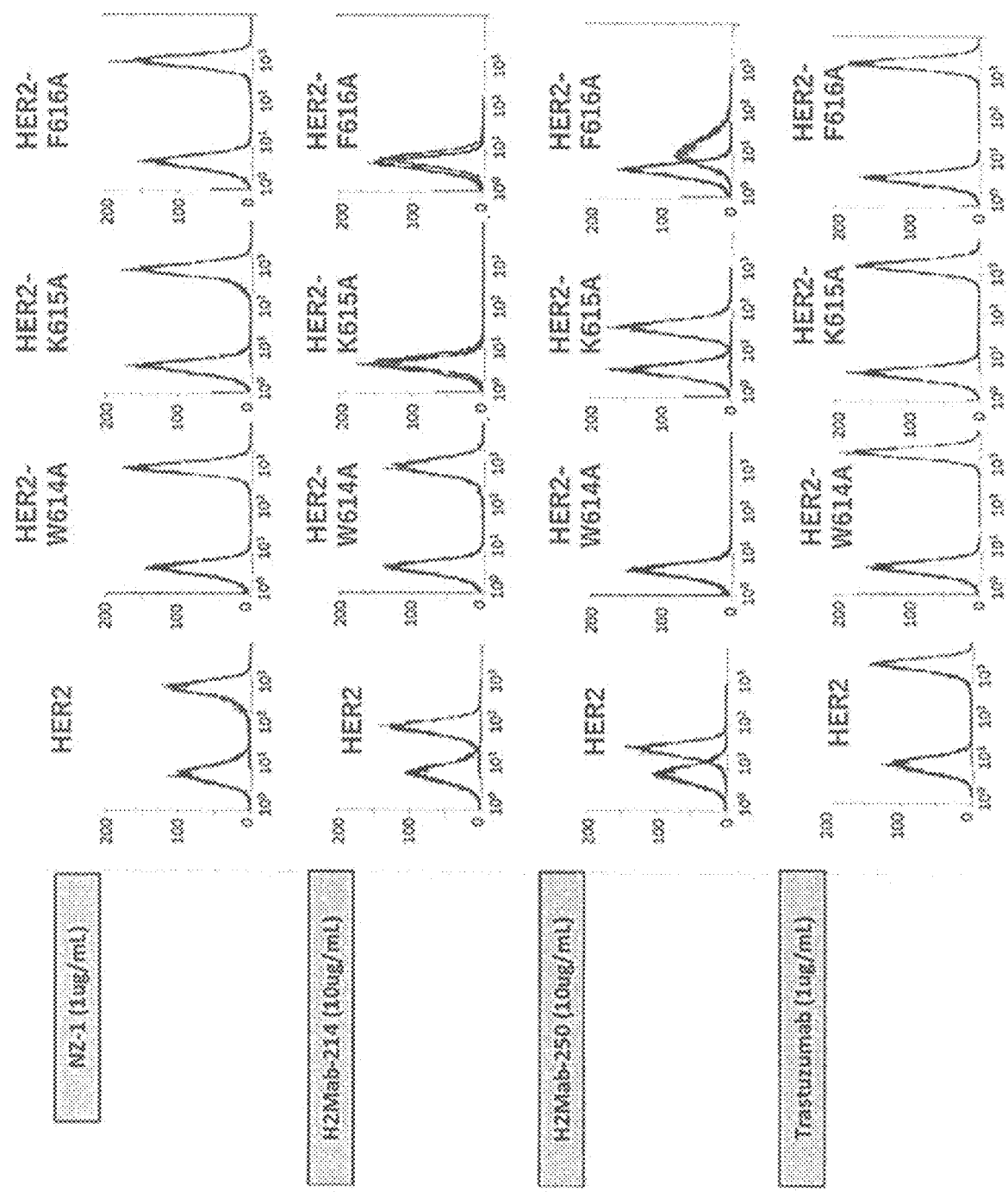
FIG. 5 shows flow cytometry (FACS) analysis results of an antibody against a PA tag (NZ-1), an H$_2$Mab-214 antibody, an H$_2$Mab-250 antibody, and a positive control antibody (trastuzumab), using CHO-K1 cells expressing various alanine-substituted variants of HER2 (W614A, K615A, F616A), respectively. On the leftmost side, CHO-K1 cells expressing wild-type HER2 were used as a positive control of the cells.
Figure 6A:
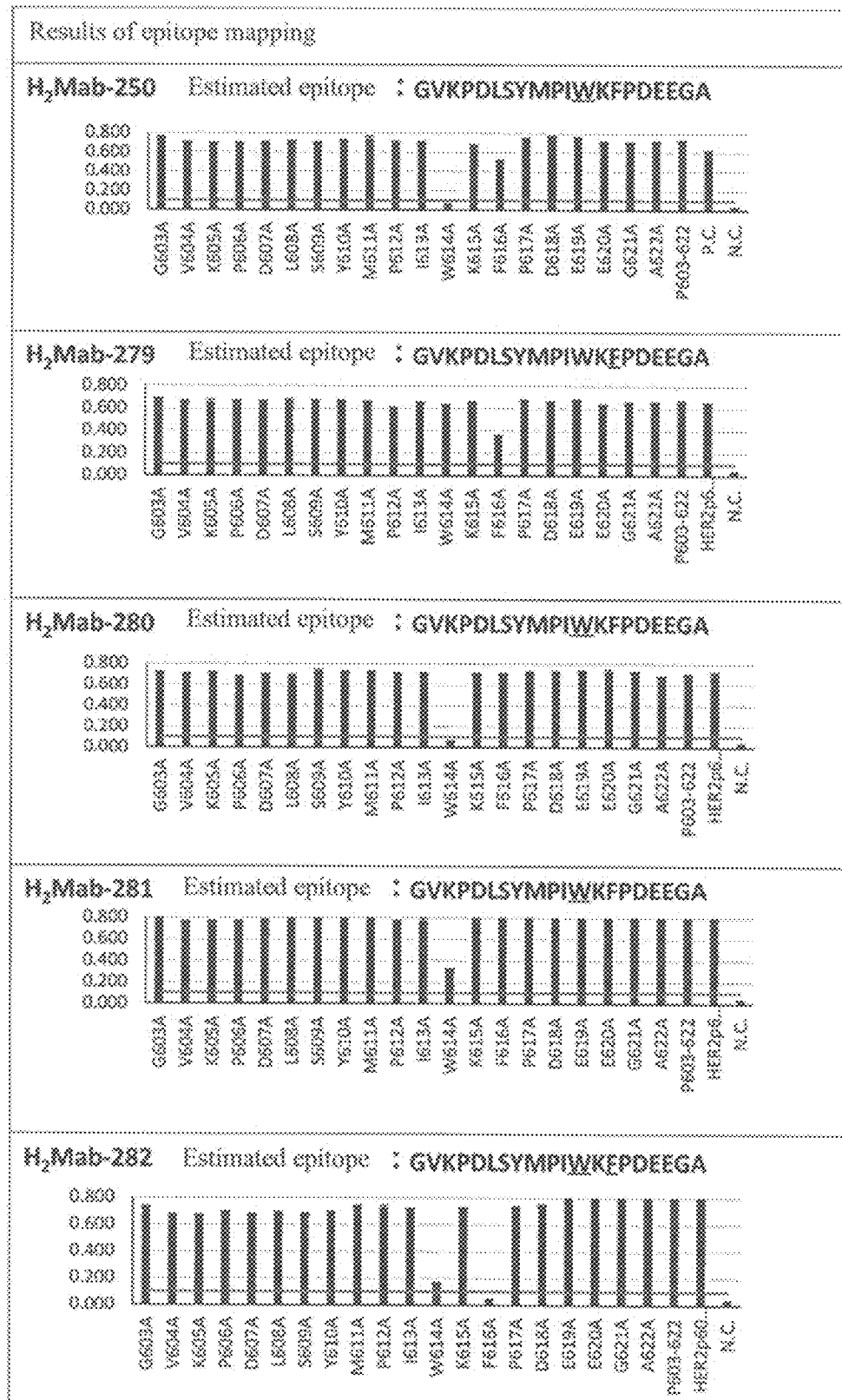
FIGS. 6A to 6E show epitope analysis results of an antibody group acquired in Example 6.
Figure 6B:
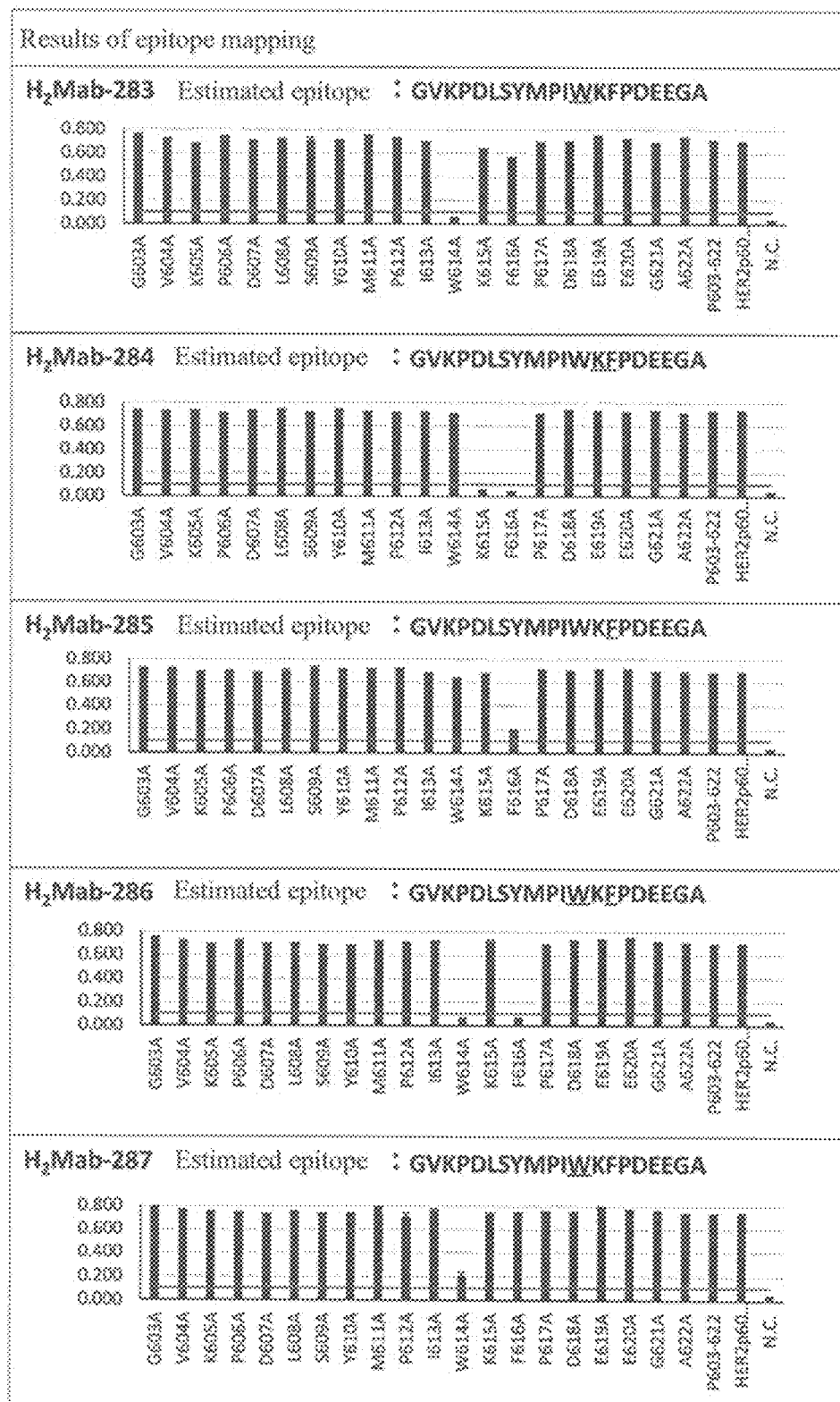
Figure 6C:
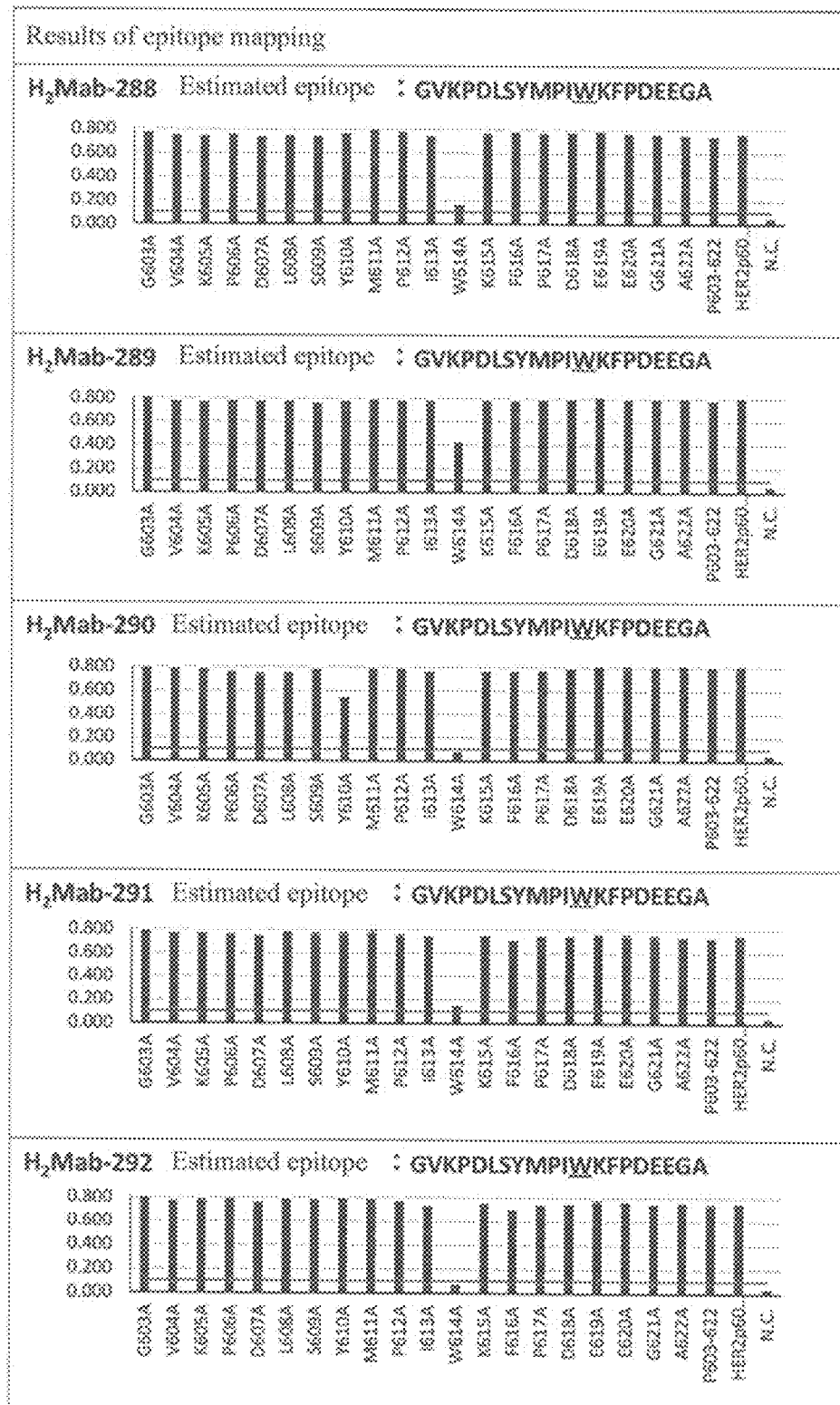
Figure 6D:
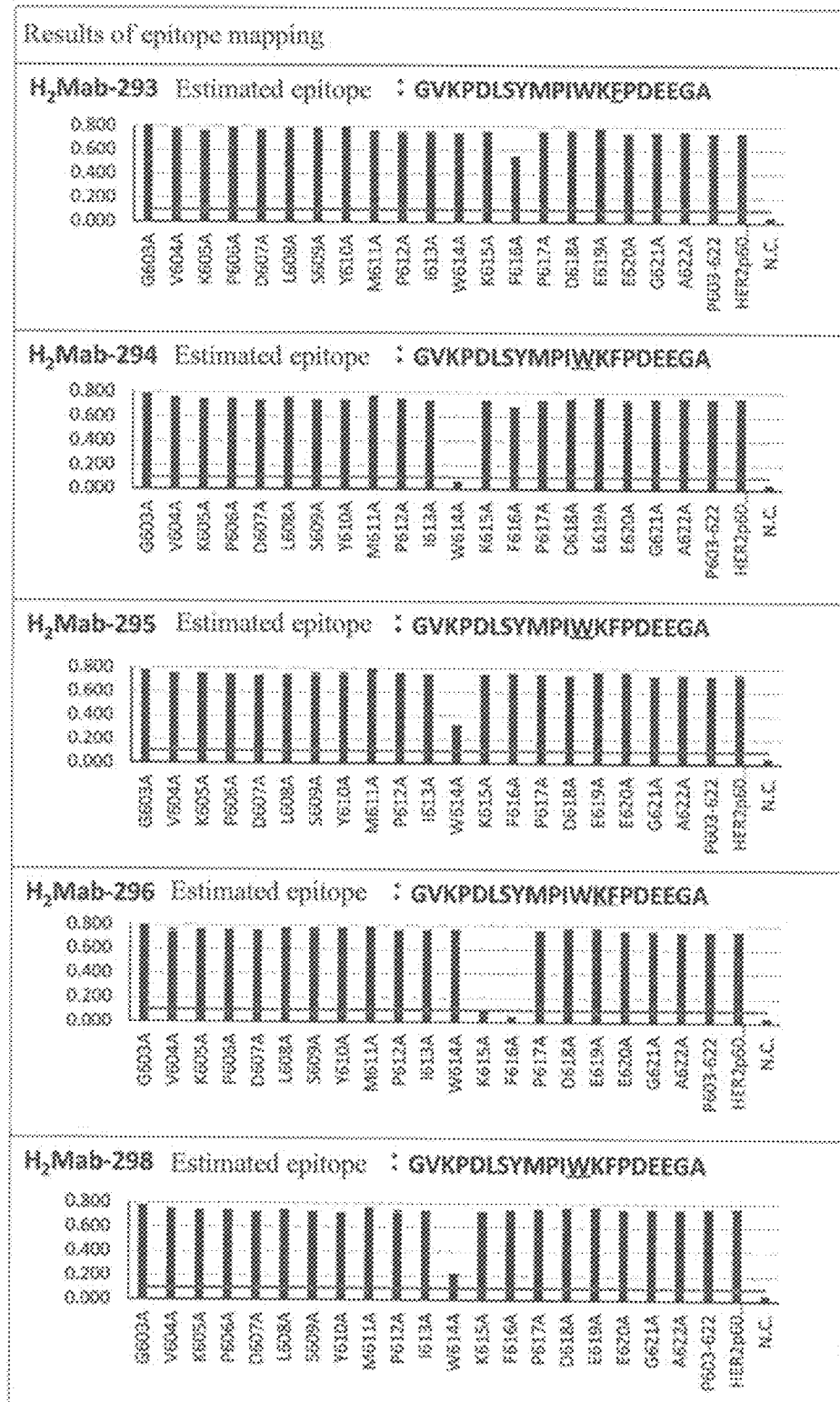
Figure 6E:
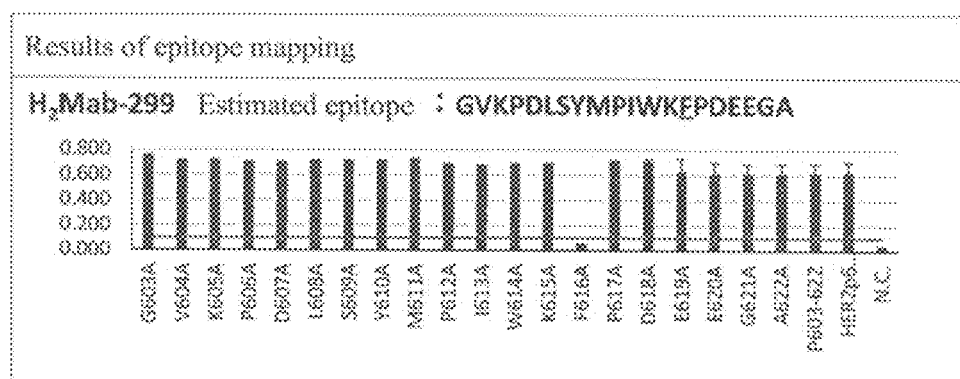
Figure 7A:
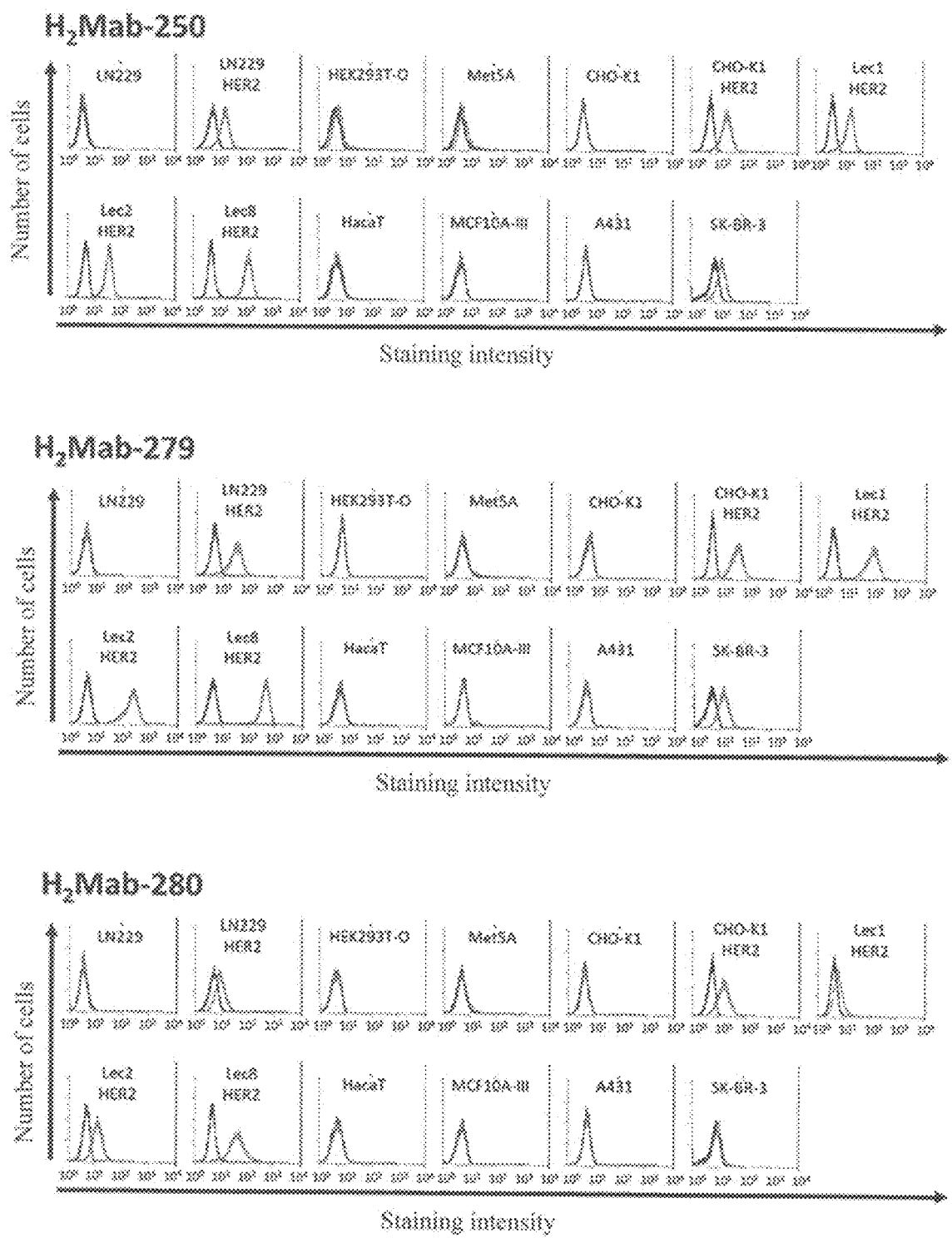
Figure 7B:
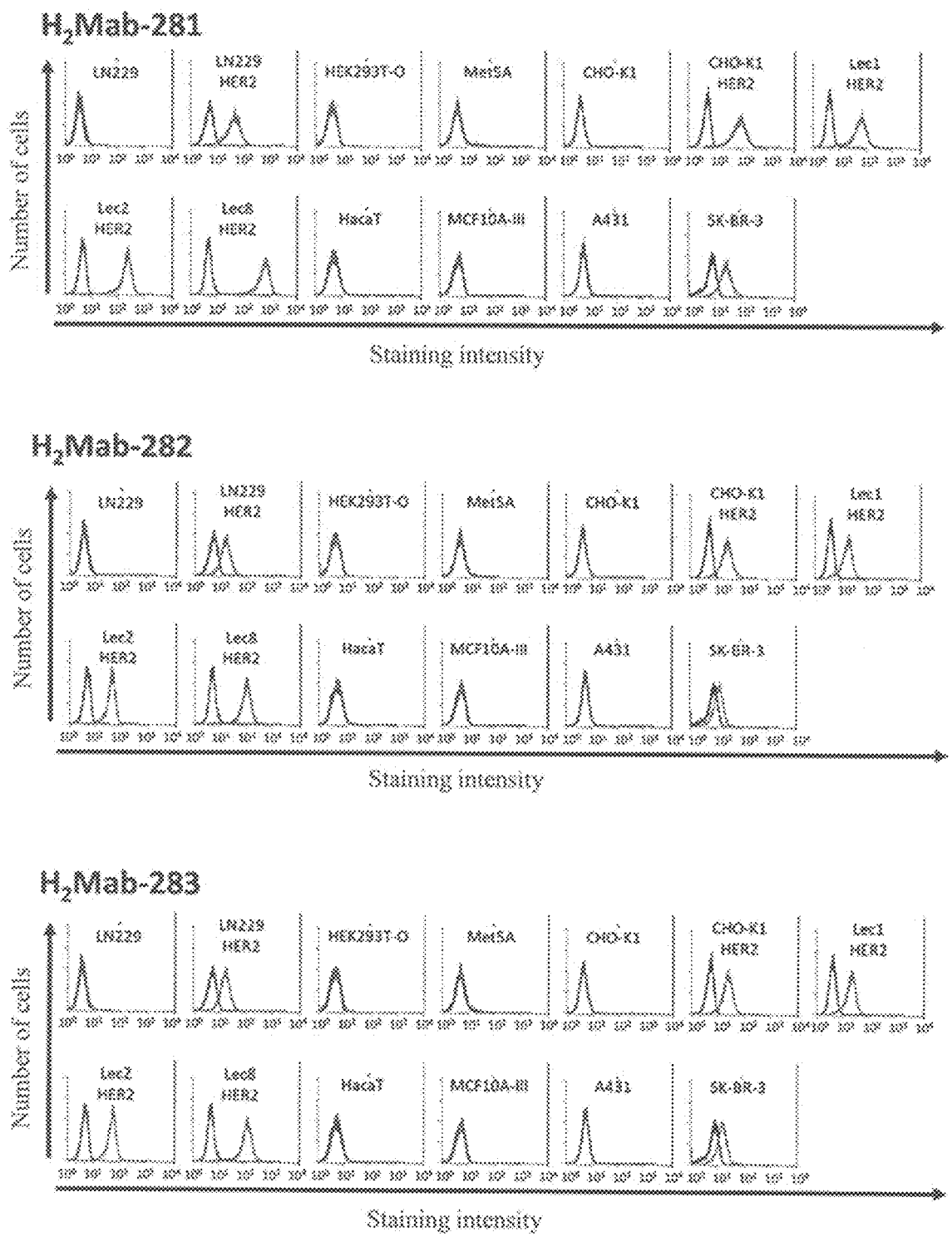
Figure 7D:
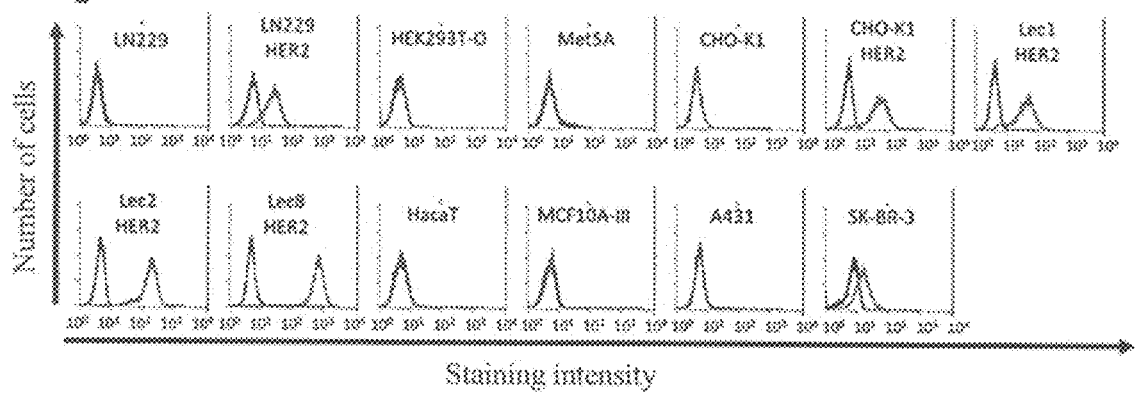
Figure 7D:
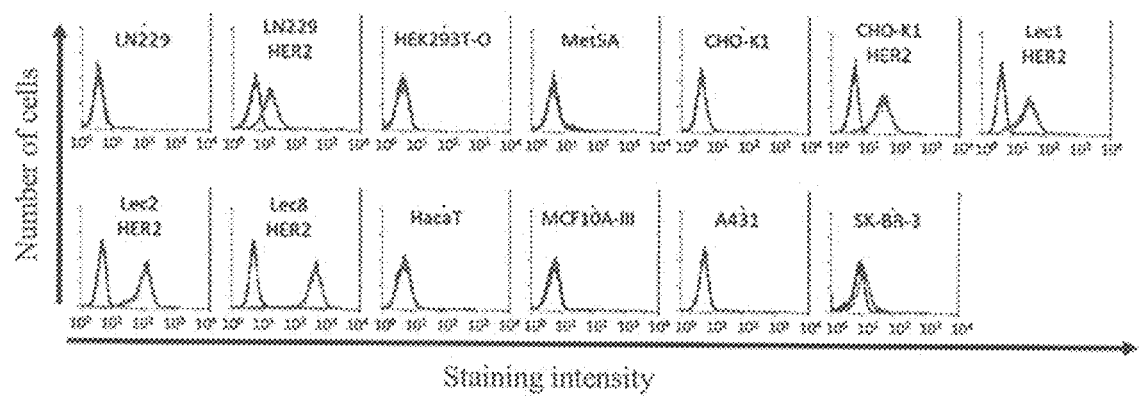
Figure 7D:
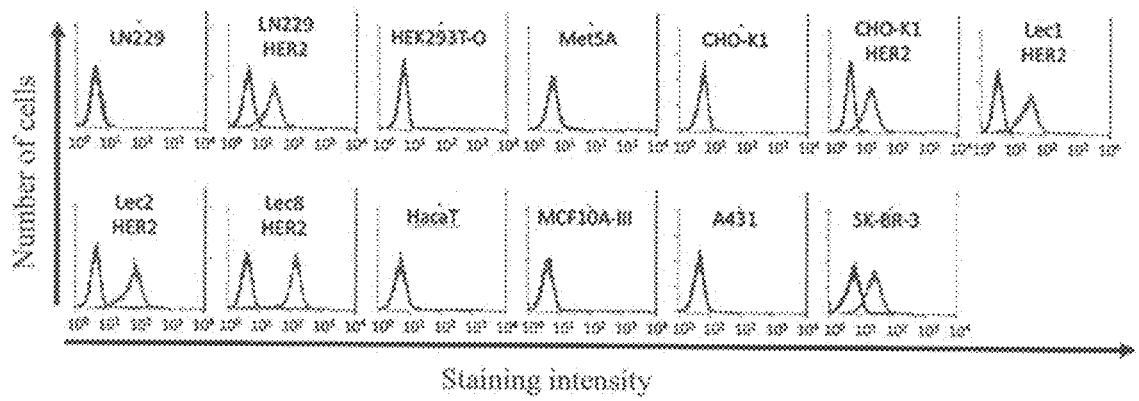
Figure 7E:
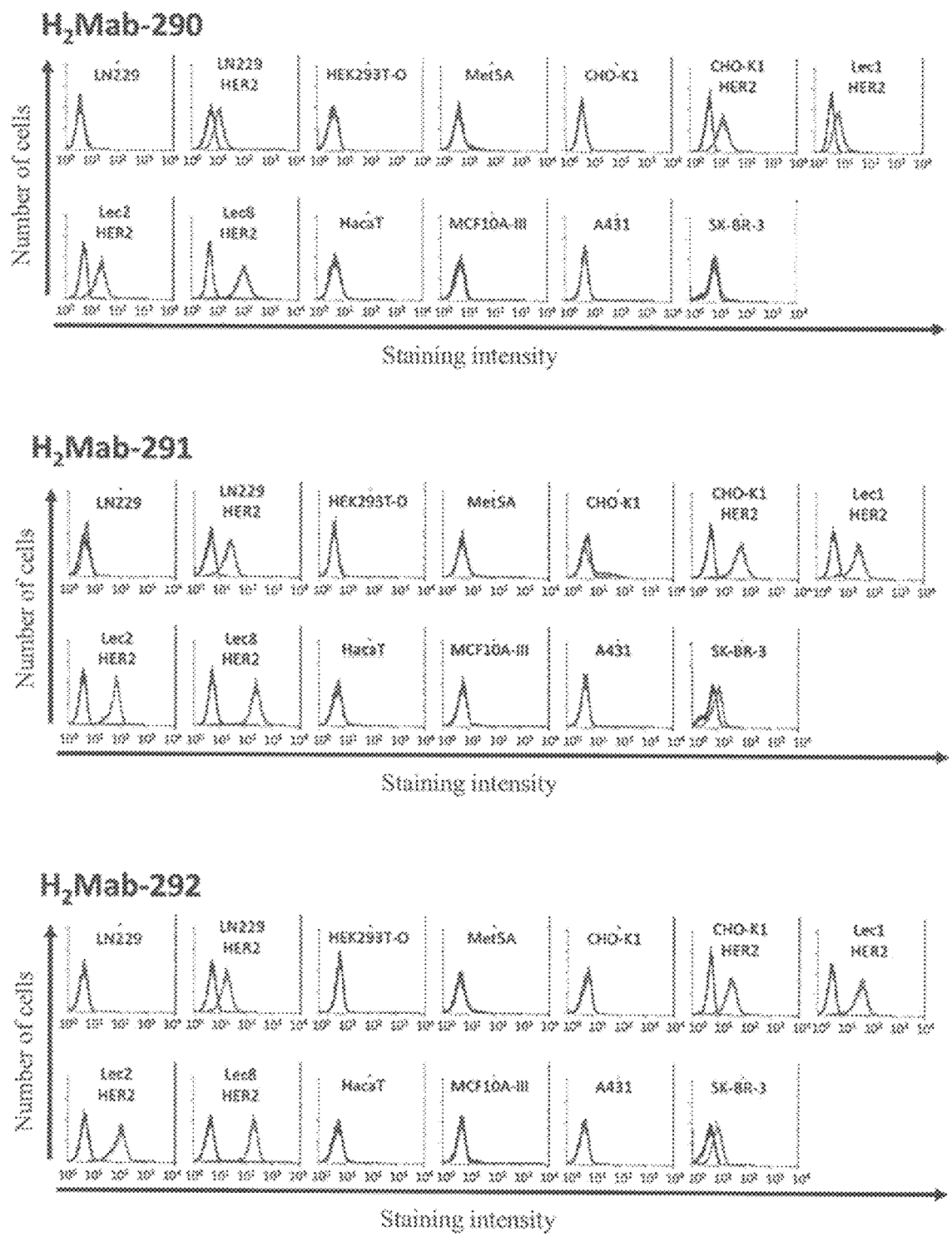
Figure 7F:
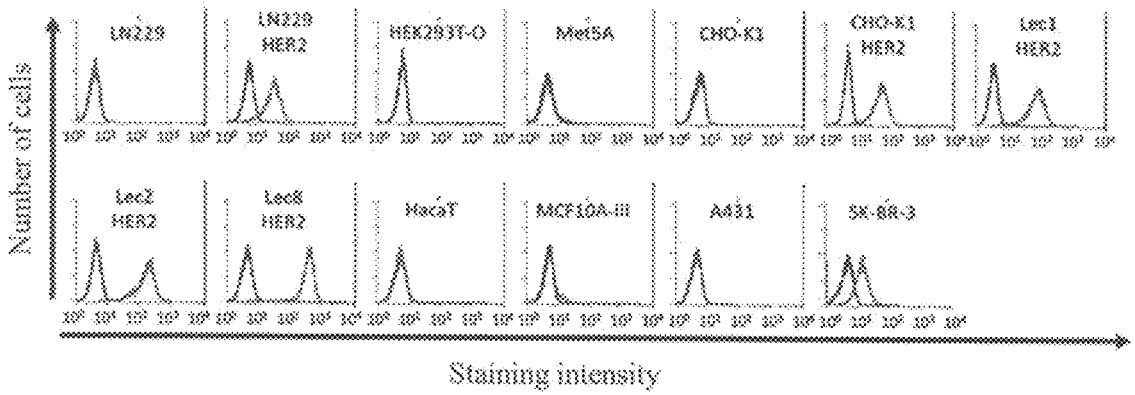
Figure 7F:
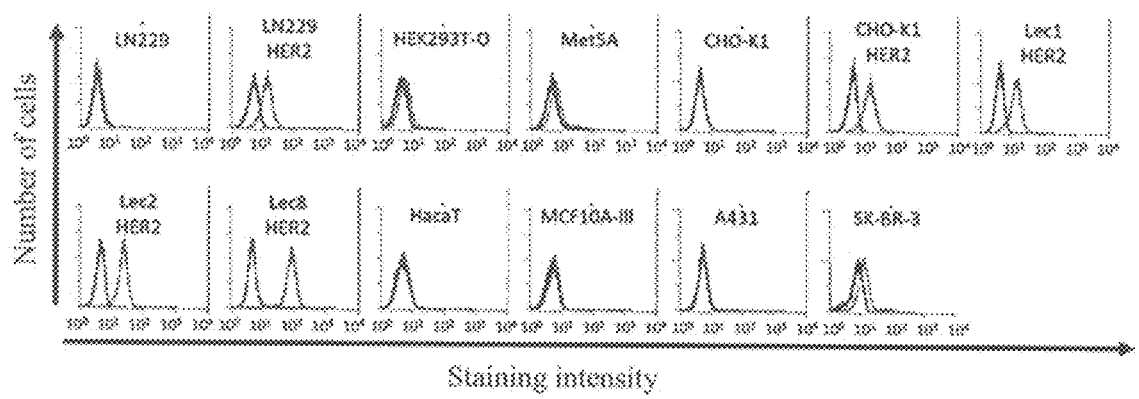
Figure 7F:
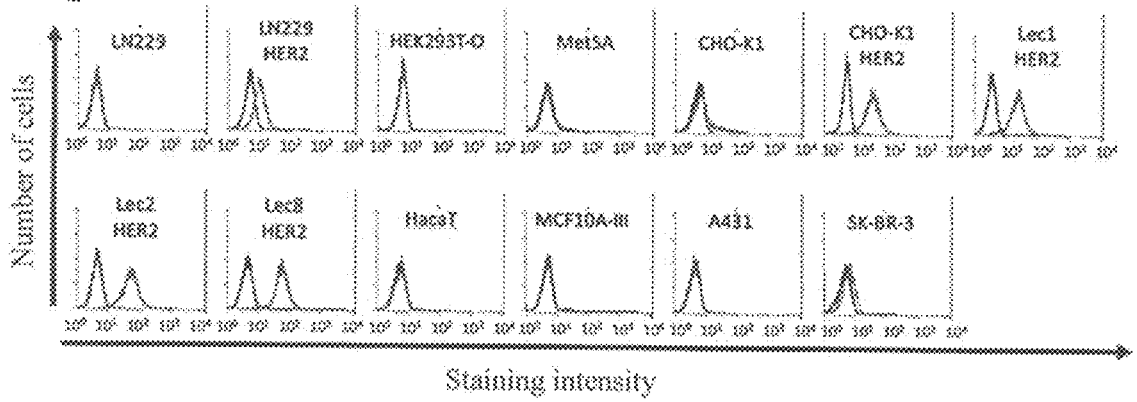
Figure 7G:
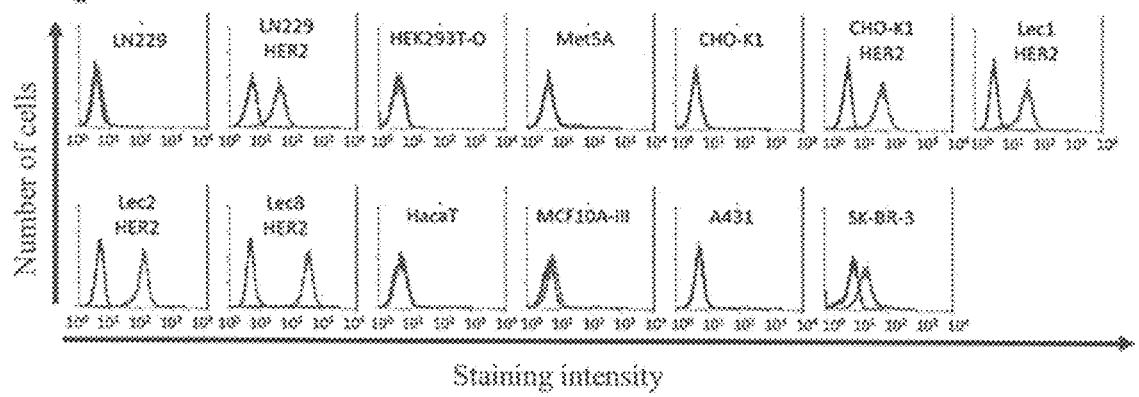
Figure 7G:
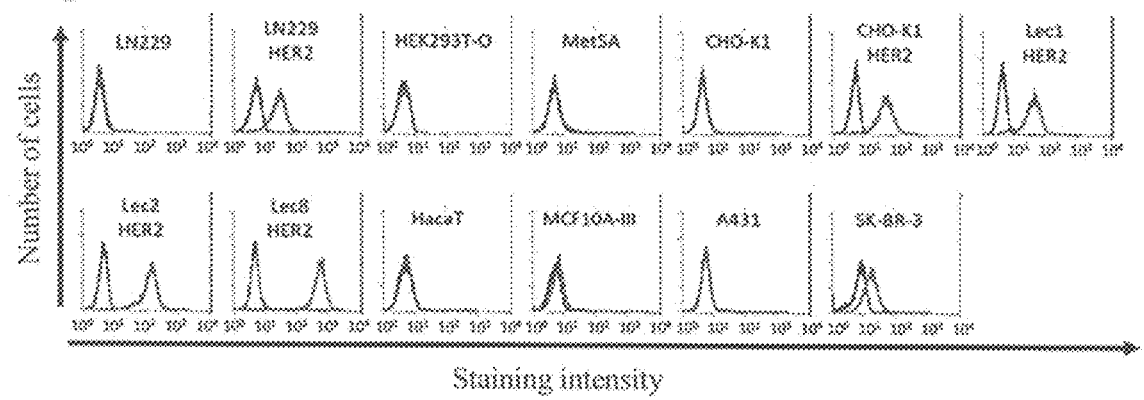
Figure 7G:
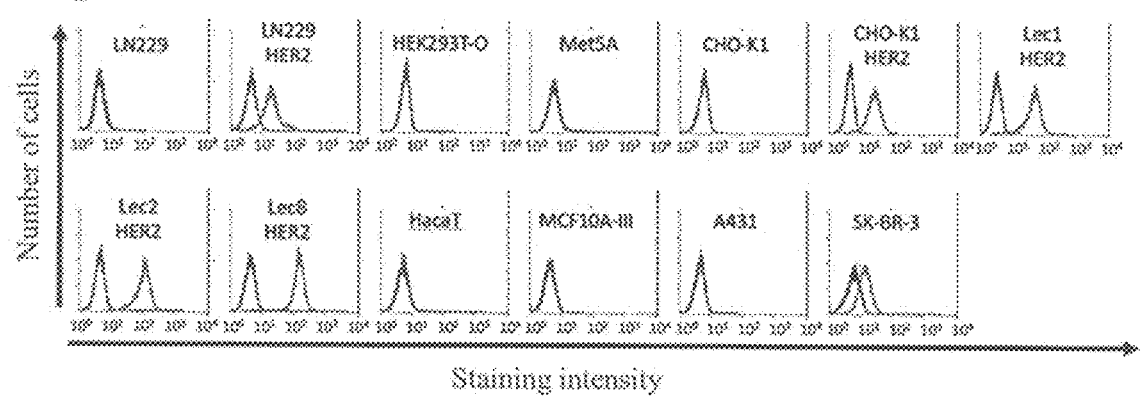
Figure 8A:
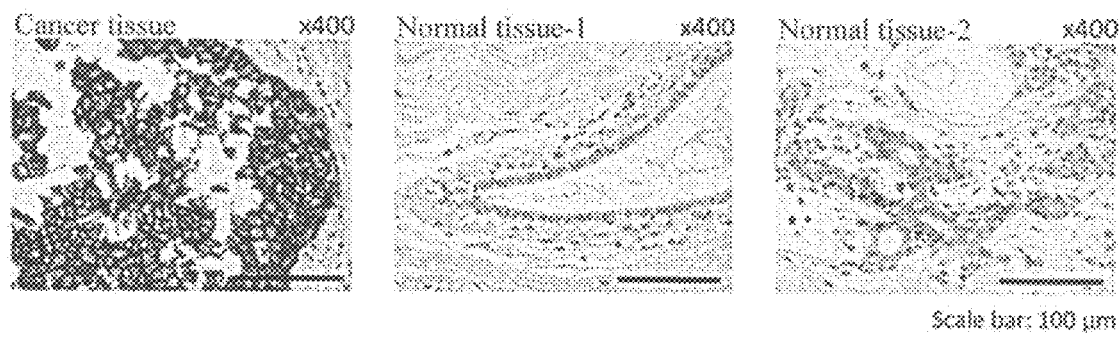
FIGS. 8A to 8F show results of immunohistochemistry (IHC) staining in cancer cells and normal cells of the antibody group acquired in Example 6.
Figure 8A:
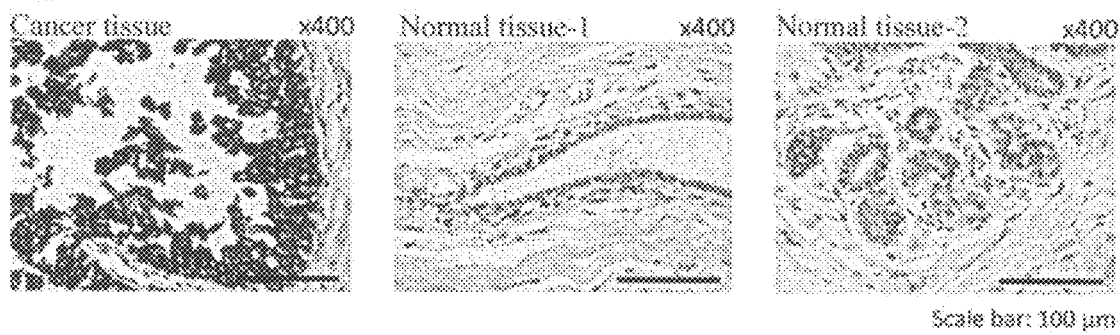
Figure 8A:
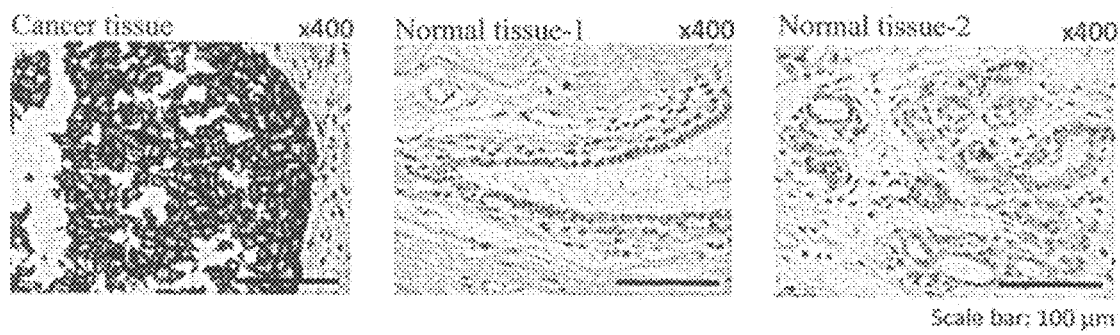
Figure 8A:
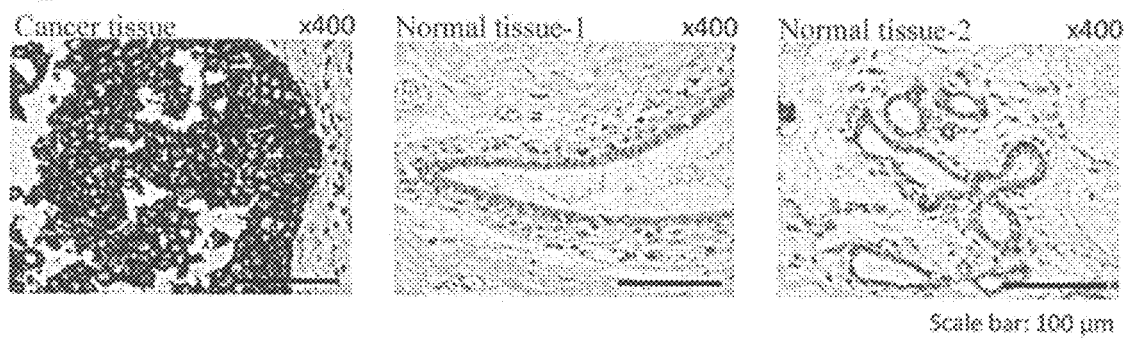
Figure 8B:
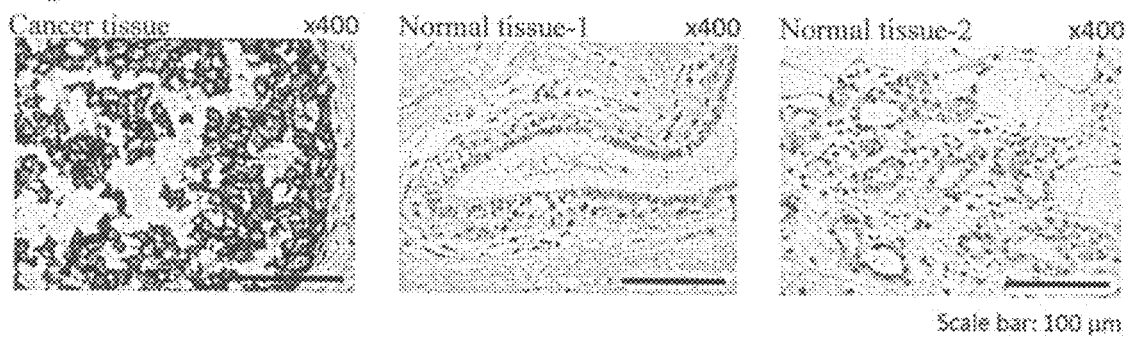
Figure 8B:
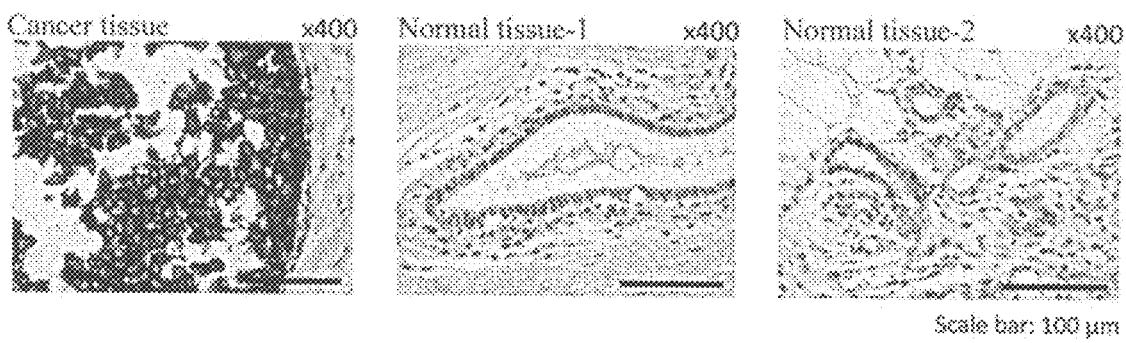
Figure 8B:
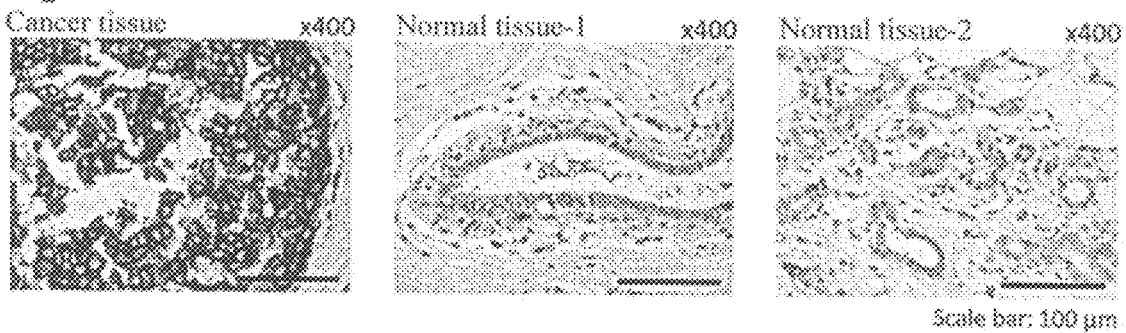
Figure 8B:
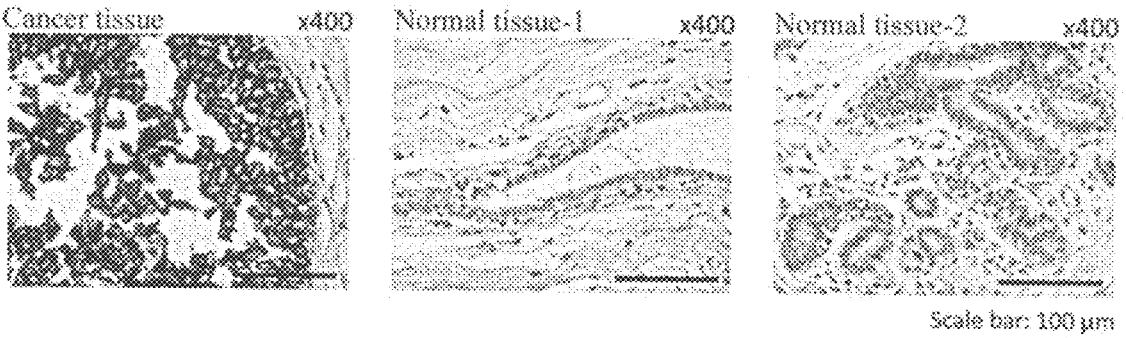
Figure 8C:
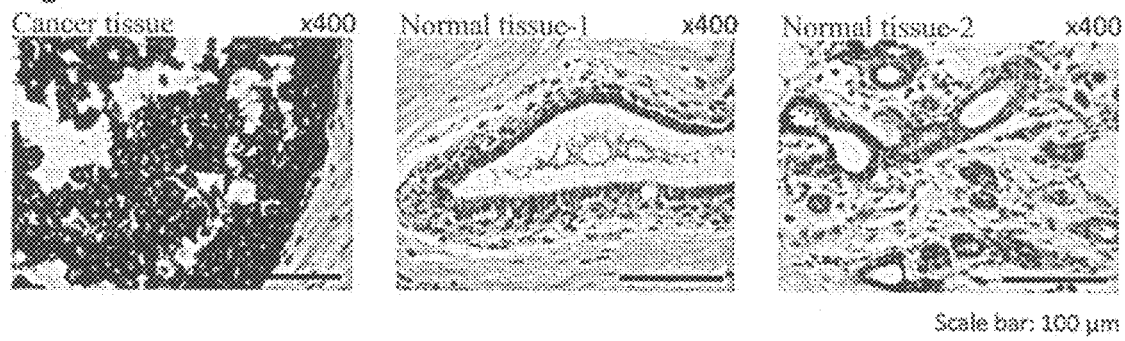
Figure 8C:
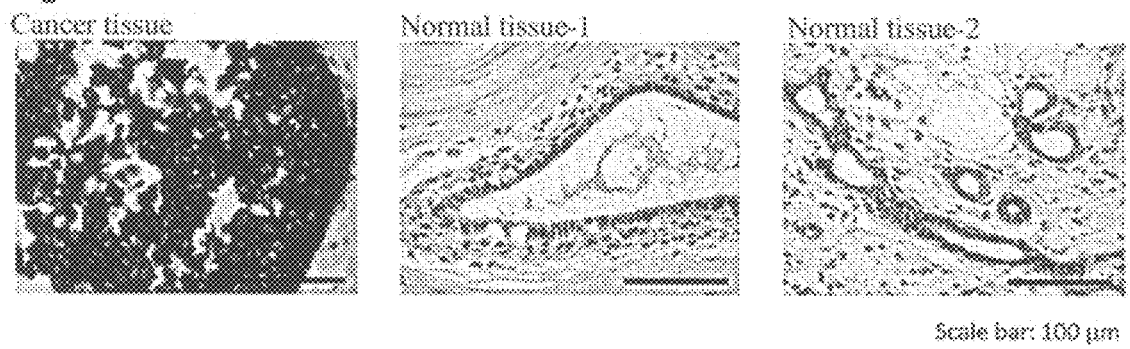
Figure 8C:
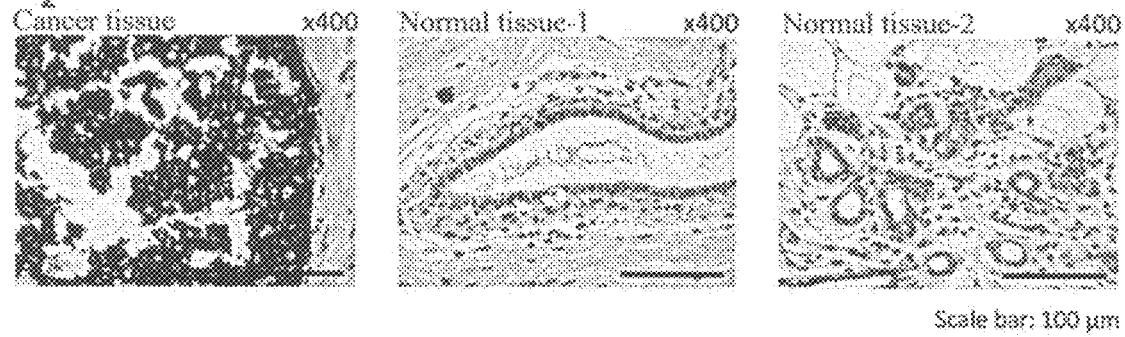
Figure 8C:
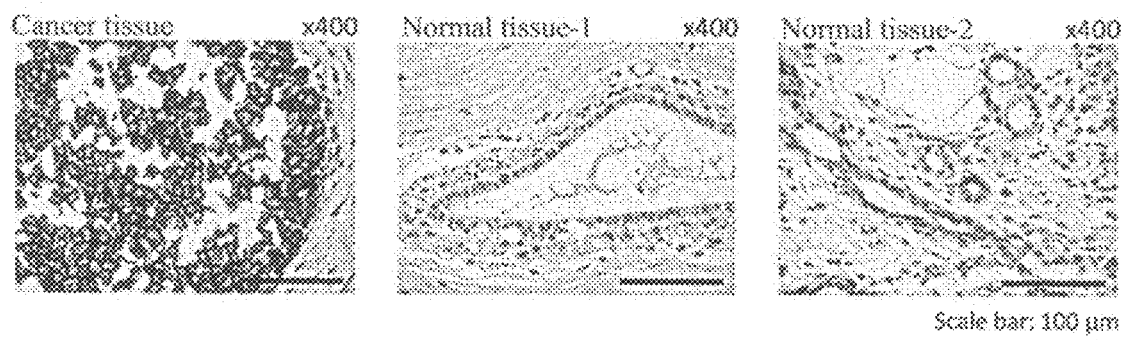
Figure 8D:
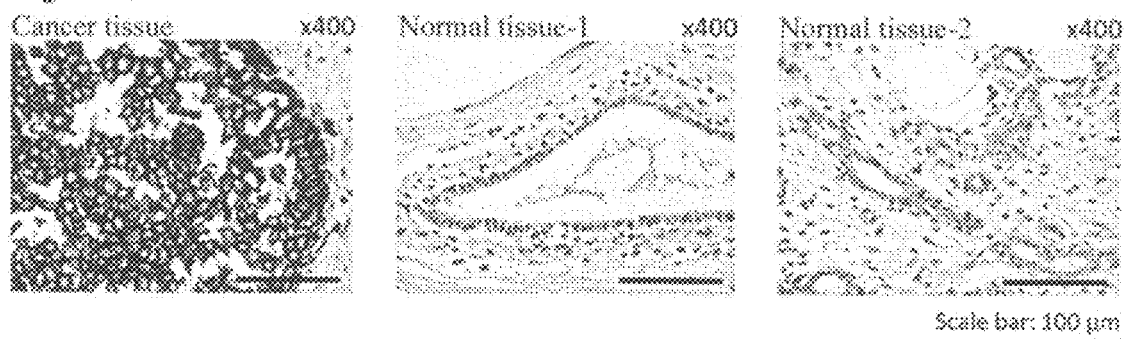
Figure 8D:
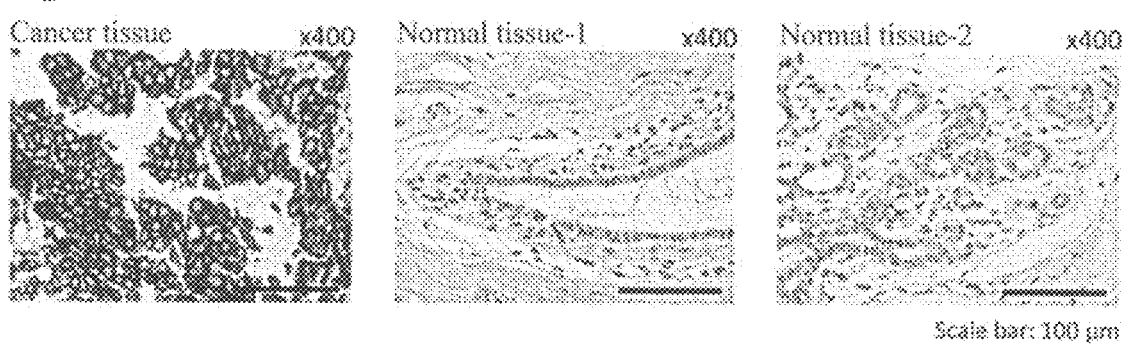
Figure 8D:
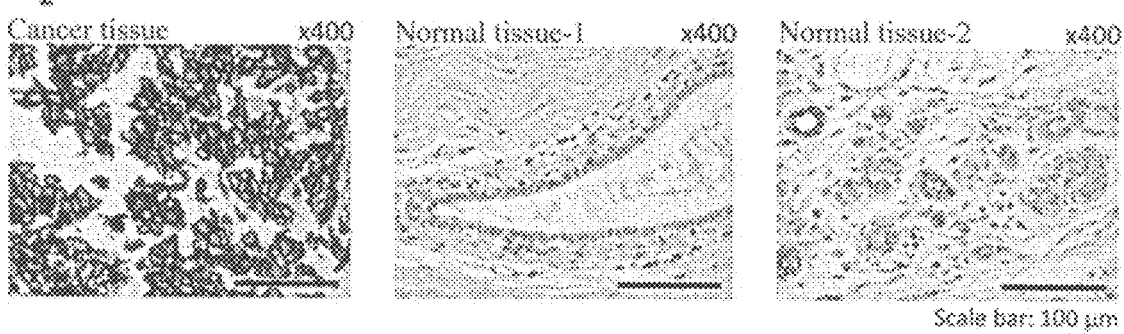
Figure 8D:
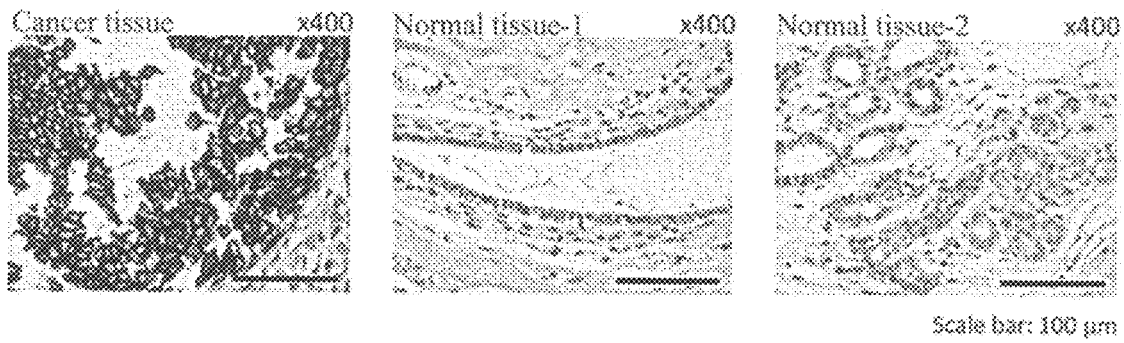
Figure 8E:
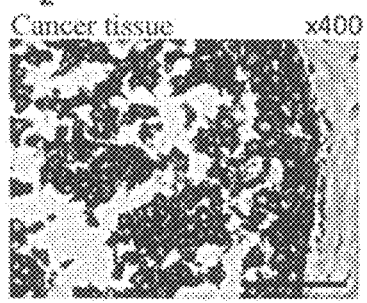
Figure 8E:
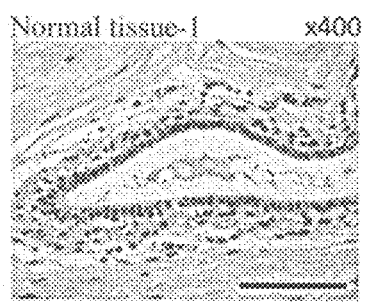
Figure 8E:
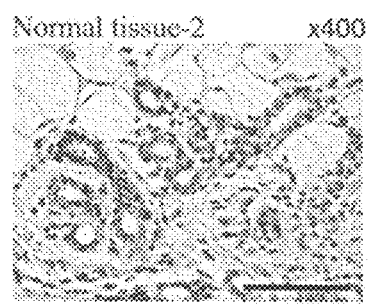
Figure 8E:
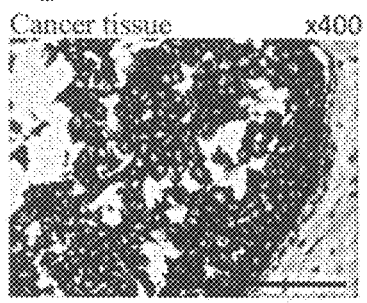
Figure 8E:
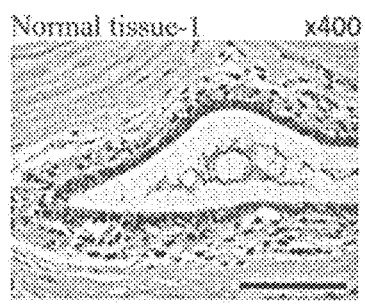
Figure 8E:
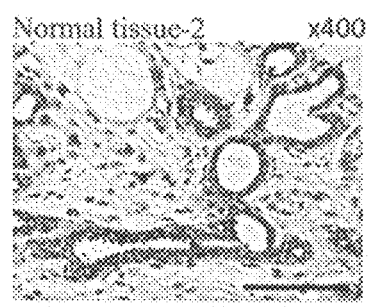
Figure 8E:
Figure 8E:
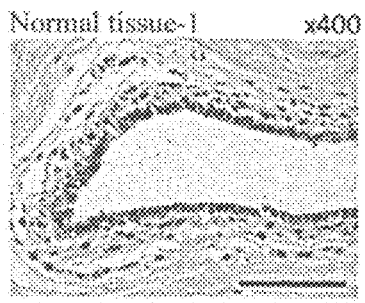
Figure 8E:
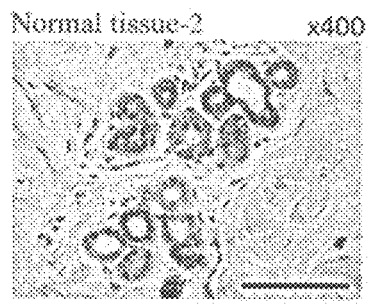
Figure 8E:
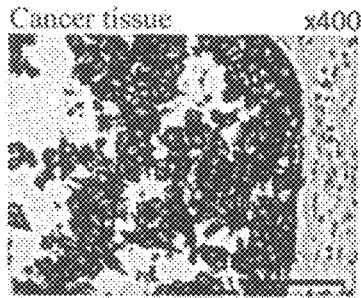
Figure 8E:
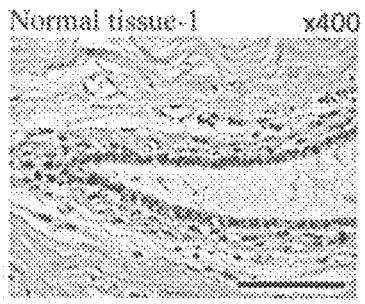
Figure 8E:
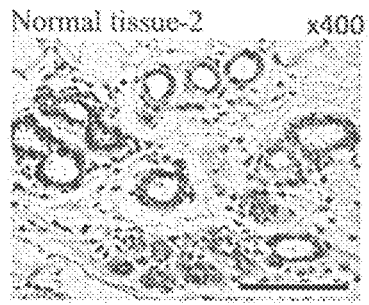
Figure 8F:
Figure 8F:
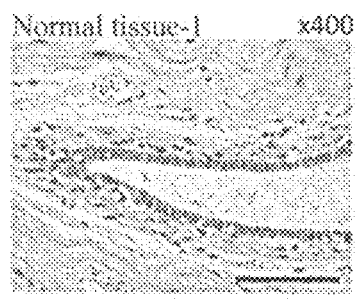
Figure 8F:
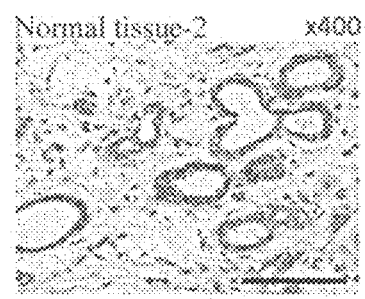

FIG. 5 shows the results of flow cytometry (FACS analysis) of an antibody against a PA tag (NZ-1), an H$_2$Mab-214 antibody, an H$_2$Mab-250 antibody, and a positive control antibody (trastuzumab).

The results show that, as shown in FIG. 5, H$_2$Mab-214 showed no significant binding to HER2-K615A and HER2-F616A, and H$_2$Mab-250 showed no significant binding to HER2-W614A. On the other hand, with the NZ-1 antibody, all the HER2 point mutants were detected, and thus it is clear that the expression amount of each point mutant was sufficient. This suggests that the antibodies of the present invention recognizing the epitopes (W614, K615, F616) do not react at all with HER2 expressed on non-cancer cells, and can specifically react with HER2 expressed on cancer cells. In addition, as shown in FIG. 5, trastuzumab showed significant binding to any of the point mutants. This suggests that trastuzumab does not recognize, out of the domain IV, the epitopes (W614, K615, F616) that the antibodies of the present invention recognize, although trastuzumab is an antibody that recognizes the domain IV of HER2 similarly to the antibodies of the present invention. Therefore, unlike trastuzumab, it is clear that the property of recognizing these epitopes (W614, K615, F616) is involved in specific recognition of HER2 on cancer cells.

(2) Biacore Measurement

Using Biacore X100 (Cytiva), interaction analysis between the H$_2$Mab-214 antibody or the H$_2$Mab-250 antibody and various peptides was performed. As the peptide, the following were used:

the amino acid sequence of amino acids of amino acid numbers 603 to 622 of human HER2 (p603-622);

peptides in which one of the amino acids of p603-p 622 is substituted with alanine (G603A, V604A, K605A, P606A, D607A, L608A, S609A, Y610A, M611A, P612A, I613A, W614A, K615A, F616A, P617A, D618A, E619A, E620A, G621A);

a peptide in which one of the amino acids of p603-622 is substituted with glycine (A622G); and partial peptides of HER2 with a deletion of part of amino acids of p603-622 (p614-619, p614-620, p614-621, p614-622, p613-618, p613-619, p613-620, p613-621, p613-622, p612-618, p612-619, p612-620, p612-621, p612-622, p611-618, p611-619, p611-620, p611-621, p611-622, p610-618, p610-619, p610-620, p610-621, p610-622, p609-618, p609-619, p609-620, p609-621, p609-622). Each of the peptides was diluted with an acetic acid buffer (pH 4.0), and the $H_2$Mab-214 antibody or the $H_2$Mab-250 antibody was immobilized on a CM5 chip by an amine coupling method. Unreacted NHS esters were blocked with ethanolamine. The interaction was measured by adding various peptides to the CM5 chip on which the $H_2$Mab-214 antibody or the $H_2$Mab-250 antibody was immobilized. PBS containing 0.005% (v/v) Tween 20 or PBS containing 0.005% (v/v) Tween 20 and 1.19% DMSO was used as a running buffer, and glycine-HCl (pH 1.5) was used as a regeneration buffer. All measurements were performed at 25° C. Measurement data were analyzed using a 1:1 binding model of BIAevaluation software (Cytiva) to determine a binding rate constant (ka), a dissociation rate constant (kd), and a dissociation constant ($K_D$). For those in which ka or kd could not be determined, $K_D$ was determined using the equilibrium value analysis method of BIAevaluation software (Cytiva).

Binding affinities determined by the Biocore measurement of the $H_2$Mab-214 antibody are shown in Tables 1 and 2, and those of the $H_2$Mab-250 antibody are shown in Tables 3 and 4. The amino acid numbers in Tables 2 and 4 indicate the amino acid regions used.

TABLE 1

Binding affinity of $H_2$Mab-214 antibody to various alanine-substituted variants

| Ligand | Analyte | $k_a$ (/Ms) | $k_d$ (/s) | $K_D$ (M) |
|---|---|---|---|---|
| H2Mab-214 | p603-622 | 2.38E+05 | 5.43E−03 | 2.28E−08 |
| | G603A | 3.35E+05 | 5.64E−03 | 1.69E−08 |
| | V604A | 2.73E+05 | 6.19E−03 | 2.27E−08 |
| | K605A | 2.43E+05 | 6.43E−03 | 2.65E−08 |
| | P606A | 3.29E+05 | 5.78E−03 | 1.76E−08 |
| | D607A | 3.34E+05 | 5.88E−03 | 1.76E−08 |
| | L608A | 1.52E+05 | 7.39E−03 | 4.87E−08 |
| | S609A | 1.99E+05 | 6.59E−03 | 3.32E−08 |
| | Y610A | 2.26E+05 | 6.03E−03 | 2.67E−08 |
| | M611A | 2.27E+05 | 7.74E−03 | 3.41E−08 |
| | P612A | 2.67E+05 | 1.25E−02 | 4.68E−08 |
| | I613A | N.D. | N.D. | 3.93E−05 |
| | W614A | N.D. | N.D. | 1.46E−06 |
| | K615A | N.D. | N.D. | 5.78E−04 |
| | F616A | N.D. | N.D. | 4.10E−04 |
| | P617A | 1.63E+05 | 7.16E−03 | 4.39E−08 |
| | D618A | 2.54E+05 | 1.25E−02 | 4.91E−08 |
| | E619A | 1.68E+05 | 1.11E−02 | 6.62E−08 |
| | E620A | 1.82E+05 | 7.62E−03 | 4.20E−08 |
| | G621A | 2.90E+05 | 5.90E−03 | 2.04E−08 |
| | A622G | 3.66E+05 | 5.67E−03 | 1.55E−08 |

N.D.: not determined

TABLE 2

Binding affinity of $H_2$Mab-214 antibody to various deletion mutants

| Ligand | Analyte | $k_a$ (/Ms) | $k_d$ (/s) | $K_D$ (M) |
|---|---|---|---|---|
| H2Mab-214 | p603-622 | 2.34E+05 | 5.34E−03 | 2.28E−08 |
| | p614-619 | 1.40E+03 | 1.19E−02 | 8.54E−06 |
| | p614-620 | 3.70E+02 | 1.52E−02 | 4.12E−05 |
| | p614-621 | N.D. | N.D. | 2.29E−04 |
| | p614-622 | 4.35E+02 | 1.15E−02 | 2.64E−05 |
| | p613-618 | 1.42E+04 | 1.30E−02 | 9.15E−07 |
| | p613-619 | 8.45E+03 | 1.36E−02 | 1.61E−06 |

TABLE 2-continued

Binding affinity of $H_2$Mab-214 antibody to various deletion mutants

| Ligand | Analyte | $k_a$ (/Ms) | $k_d$ (/s) | $K_D$ (M) |
|---|---|---|---|---|
| | p613-620 | 4.34E+03 | 1.00E−02 | 2.31E−06 |
| | p613-621 | 7.36E+02 | 9.55E−03 | 1.30E−05 |
| | p613-622 | N.D. | N.D. | 1.27E−04 |
| | p612-618 | 4.67E+05 | 1.30E−02 | 2.77E−08 |
| | p612-619 | 1.06E+06 | 2.35E−02 | 2.22E−08 |
| | p612-620 | 7.54E+05 | 1.79E−02 | 2.37E−08 |
| | p612-621 | 8.59E+05 | 2.40E−02 | 2.79E−08 |
| | p612-622 | 6.15E+05 | 2.44E−02 | 3.97E−08 |
| | p611-618 | 6.69E+05 | 1.41E−02 | 2.10E−08 |
| | p611-619 | 7.47E+05 | 8.30E−03 | 1.11E−08 |
| | p611-620 | 4.75E+05 | 8.36E−03 | 1.76E−08 |
| | p611-621 | 5.71E+05 | 9.61E−03 | 1.68E−08 |
| | p611-622 | 4.51E+05 | 1.08E−02 | 2.39E−08 |
| | p610-618 | 8.37E+05 | 1.21E−02 | 1.45E−08 |
| | p610-619 | 8.89E+05 | 5.10E−03 | 5.74E−09 |
| | p610-620 | 5.79E+05 | 5.02E−03 | 8.68E−09 |
| | p610-621 | 6.79E+05 | 5.19E−03 | 8.57E−09 |
| | p610-622 | 1.54E+05 | 5.98E−03 | 3.88E−08 |
| | p609-618 | 7.47E+05 | 1.07E−02 | 1.43E−08 |
| | p609-619 | 7.79E+05 | 4.49E−03 | 5.76E−09 |
| | p609-620 | 6.45E+05 | 4.45E−03 | 6.89E−09 |
| | p609-621 | 5.77E+05 | 4.65E−03 | 8.06E−09 |
| | p609-622 | 5.61E+05 | 5.26E−03 | 9.37E−09 |

N.D.: not determined

TABLE 3

Binding affinity of $H_2$Mab-250 antibody to various alanine-substituted variants

| Ligand | Analyte | $k_a$ (/Ms) | $k_d$ (/s) | $K_D$ (M) |
|---|---|---|---|---|
| H2Mab-250 | p603-622 | 6.39E+04 | 3.70E−04 | 5.8E−09 |
| | G603A | 7.33E+04 | 4.30E−04 | 5.87E−09 |
| | V604A | 6.10E+04 | 3.99E−04 | 6.54E−09 |
| | K605A | 5.36E+04 | 3.46E−04 | 6.45E−09 |
| | P606A | 7.36E+04 | 3.93E−04 | 5.34E−09 |
| | D607A | 7.36E+04 | 5.20E−04 | 7.06E−09 |
| | L608A | 4.91E+04 | 4.31E−04 | 8.79E−09 |
| | S609A | 6.06E+04 | 3.94E−04 | 6.51E−09 |
| | Y610A | 5.71E+04 | 4.51E−04 | 7.90E−09 |
| | M611A | 5.97E+04 | 4.45E−04 | 7.45E−09 |
| | P612A | 6.38E+04 | 6.09E−04 | 9.54E−09 |
| | I613A | 8.84E+04 | 8.28E−03 | 9.39E−08 |
| | W614A | N.D. | 4.38E−03 | 1.05E−03 |
| | K615A | 2.87E+04 | 9.63E−03 | 3.36E−07 |
| | F616A | 5.28E+04 | 1.08E−02 | 2.04E−07 |
| | P617A | 4.41E+04 | 9.14E−03 | 2.07E−07 |
| | D618A | 7.45E+04 | 4.32E−04 | 5.80E−09 |
| | E619A | 7.39E+04 | 4.65E−04 | 6.29E−09 |
| | E620A | 5.71E+04 | 4.55E−04 | 7.98E−09 |
| | G621A | 5.78E+04 | 3.99E−04 | 6.91E−09 |
| | A622G | 6.59E+04 | 4.53E−04 | 6.87E−09 |

N.D.: not determined

TABLE 4

Binding affinity of $H_2$Mab-250 antibody to various deletion mutants

| Ligand | Analyte | $k_a$ (/Ms) | $k_d$ (/s) | $K_D$ (M) |
|---|---|---|---|---|
| H2Mab-250 | p603-622 | 9.01E+04 | 3.30E−04 | 3.67E−09 |
| | p614-619 | 8.54E+02 | 1.18E−03 | 1.38E−06 |
| | p614-620 | N.D. | N.D. | 2.64E−05 |
| | p614-621 | N.D. | N.D. | 2.66E−05 |
| | p614-622 | 4.98E+02 | 1.45E−03 | 2.91E−06 |
| | p613-618 | 6.49E+04 | 2.89E−03 | 4.45E−09 |
| | p613-619 | 3.97E+05 | 4.10E−03 | 1.03E−08 |
| | p613-620 | 2.83E+05 | 3.71E−03 | 1.31E−08 |
| | p613-621 | 3.25E+05 | 3.43E−03 | 1.05E−08 |
| | p613-622 | 2.47E+05 | 3.46E−03 | 1.40E−08 |

TABLE 4-continued

Binding affinity of H₂Mab-250 antibody to various deletion mutants

| Ligand | Analyte | $k_a$ (/Ms) | $k_d$ (/s) | $K_D$ (M) |
|---|---|---|---|---|
| | p612-618 | 2.96E+05 | 5.70E−04 | 1.92E−09 |
| | p612-619 | 2.50E+05 | 8.41E−04 | 3.36E−09 |
| | p612-620 | 1.72E+05 | 7.56E−04 | 4.39E−09 |
| | p612-621 | 1.96E+05 | 6.83E−04 | 3.49E−09 |
| | p612-622 | 1.94E+05 | 7.24E−04 | 3.74E−09 |
| | p611-618 | 3.56E+05 | 3.10E−04 | 8.69E−10 |
| | p611-619 | 2.40E+05 | 4.87E−04 | 2.02E−09 |
| | p611-620 | 1.46E+05 | 3.87E−04 | 2.65E−09 |
| | p611-621 | 2.18E+05 | 4.11E−04 | 1.89E−09 |
| | p611-622 | 1.87E+05 | 3.78E−04 | 2.02E−09 |
| | p610-618 | 3.76E+05 | 2.25E−04 | 5.99E−10 |
| | p610-619 | 3.19E+05 | 3.80E−04 | 1.19E−09 |
| | p610-620 | 2.60E+05 | 3.42E−04 | 1.32E−09 |
| | p610-621 | 2.56E+05 | 3.47E−04 | 1.36E−09 |
| | p610-622 | 1.83E+05 | 3.30E−04 | 1.81E−09 |
| | p609-618 | 2.62E+05 | 2.10E−04 | 8.03E−10 |
| | p609-619 | 2.44E+05 | 2.93E−04 | 1.20E−09 |
| | p609-620 | 2.34E+05 | 2.91E−04 | 1.24E−09 |
| | p609-621 | 2.47E+05 | 2.89E−04 | 1.17E−09 |
| | p609-622 | 2.10E+05 | 3.30E−04 | 1.57E−09 |

N.D.: not determined

The results of Examples 4 and 5 prove the correlation of the binding affinity of the antibody of the present invention to various alanine-substituted variants and various deletion mutants correlated, and thus it was found that two amino acids of K615 and F616 and their surroundings (I613, W614) are epitopes of the H₂Mab-214 antibody.

In addition, the amino acid of W614 and its surroundings (I613, K615, F616, P617) were found to be an epitope of the H₂Mab-250 antibody.

Example 6: Group of Additional Antibodies

In this example, an attempt was made to obtain a further anti-HER2 antibody.

Mouse

BALB/c mice aged 6 weeks were purchased from CLEA Japan.

Immunogen

As an immunogen, 20 amino acids (HER2_604-622C;$_{NH2-}$ VKPDLSYMPIWKFPDEEGAC$_{-COOH}$; SEQ ID NO: 37) obtained by adding Cys to the C-terminus of amino acids of 604-622 (19 amino acids) of HER2 were synthesized (Eurofins), and KLH was added thereto by a conventional method. The purification purity of the peptide was 90% or more.

Immunization

100 µg/mouse (100 l) of HER2_604-622C and 100 µl of ImjectAlum (Thermo Fisher Scientific, Inc.) were mixed to perform the first immunization. Thereafter, immunization was performed weekly with 100 µg/mouse (100 µl) (without ImjectAlum) as the second, third, fourth and fifth immunizations. Two days after the fifth immunization, splenocytes were separated from the spleen extracted from the mouse by a conventional method, and cell fusion was performed at a ratio of splenocytes:mouse myeloma cells (P3U1)=10:1. Cell fusion was carried out by a conventional method using PEG1500 (Roche Diagnostics).

Culture of Hybridoma

Hybridomas were seeded on a 96-well plate using 10% FBS (Thermo Fisher Scientific, Inc.) in RPMI (Nacalai Tesque, Inc.) containing HAT (Thermo Fisher Scientific, Inc.).

Screening

After 6 days, screening was performed by ELISA. ELISA was performed as follows. HER2 p604-622C was dissolved in DMSO at 10 mg/mL and then diluted with PBS (1 µg/ml). For immobilization of the peptide, 50 ng/well (50 µL/well) of HER2p604-622C was added to the plate, and incubation was performed at 37° C. for 30 minutes. Blocking was performed by adding 1% BSA/PBS-Tween (0.05%) at 100 µL/well and incubating at 37° C. for 30 minutes. 50 µl of the culture supernatant of the hybridoma was added, and the mixture was incubated at 37° C. for 30 minutes. For the secondary antibody, 50 µl each of anti-mouse Immunoglobulins/HRP (Agilent, diluted to 1/2000 with 1% BSA/PBS-0.05% Tween) was added, and the mixture was incubated at 37° C. for 30 minutes. For color development, 50 µl each of ELISA POD substrate TMB kit (Nacalai Tesque, Inc.) was added, and the mixture was incubated at room temperature for 10 minutes. The measurement was performed on an iMark Microplate Reader (OD 655 nm) at 15 min.

Single Cell Cloning

Single cell cloning was performed for positive wells. Clones were visually confirmed, and positive clones were established by ELISA. The clones were named as H₂Mab-279 to H₂Mab-299.

Determination of Subclasses

Subclasses were determined by a conventional method (similar to (H₂Mab-214,250).

TABLE 5

Subclass and light chain of additional antibody clones

| Clone name | Subclass | Light chain |
|---|---|---|
| H₂Mab-279 | IgG₃ | κ |
| H₂Mab-280 | IgG₁ | κ |
| H₂Mab-281 | IgG₁ | κ |
| H₂Mab-282 | IgG$_{2a}$ | κ |
| H₂Mab-283 | IgG₁ | κ |
| H₂Mab-284 | IgG₁ | κ |
| H₂Mab-285 | IgG₃ | κ |
| H₂Mab-286 | IgG₁ | κ |
| H₂Mab-287 | IgG₁ | κ |
| H₂Mab-288 | IgG₁ | κ |
| H₂Mab-289 | IgG₁ | κ |
| H₂Mab-290 | IgG₁ | κ |
| H₂Mab-291 | IgG₃ | κ |
| H₂Mab-292 | IgG₃ | κ |
| H₂Mab-293 | IgG₃ | κ |
| H₂Mab-294 | IgG₁ | κ |
| H₂Mab-295 | IgG₁ | κ |
| H₂Mab-296 | IgG₁ | κ |
| H₂Mab-297 | IgG$_{2a}$ | κ |
| H₂Mab-298 | IgG₁ | κ |
| H₂Mab-299 | IgG₁ | κ |

Each antibody was purified as in Example 1 (1). Ab-Capcher™ (Protenova) was used for the purification column. Purified antibodies were subjected to epitope analysis, FACS, and immunohistochemical staining. FACS was performed as described in Example 1 (4), and immunohistochemical staining was performed as described in Example 1 (6). Epitope analysis was performed by ELISA as described in Example 4.

In the epitope analysis, when an antibody tested for a peptide changed to alanine by alanine scan had a reduced binding affinity or lost a binding affinity, the amino acid changed to alanine was determined as the estimated epitope of the antibody. The results of epitope analysis were as shown in FIGS. 6A to 6E. In FIGS. 6A to 6E, the estimated epitopes are indicated by underlines. As shown in FIGS. 6A to 6E, the estimated epitopes of the antibody clones were all observed in the regions of W614, K615, and F616.

In the FACS analysis, the binding between the living cells shown in the drawings and each antibody clone was tested. Met5A cells were used as a mesothelioma cell line, HaCaT cells were used as a human epidermal keratinocyte cell line, MCF10A-III was used as a non-tumor epithelial cell line, A431 was used as a human epidermoid carcinoma cell line, and SK-BR-3 was used as a breast cancer cell line. The results were as shown in FIGS. 7A to 7G. As shown in FIGS. 7A to 7G, most of the cell clones using the amino acids of SEQ ID NO: 37 as an immunogen did not bind to normal cells, and showed binding to positive cancer cells.

The results of immunohistochemical staining were as shown in FIGS. 8A to 8F. As shown in FIGS. 8A to 8F, all of the antibody clones using the amino acids of SEQ ID NO: 37 as an immunogen strongly reacted to cancer tissues, but hardly reacted to normal tissues.

Antibody Gene Cloning

Antibody gene cloning, heavy and light chain variable region estimation, and CDR estimation were performed as described in Example 2. The activities of the recombinant antibodies could be confirmed by FACS.

The amino acid numbers of the heavy chain variable region and the light chain variable region in the amino acid sequences of SEQ ID NOs: 14 to 17 and 39 to 80 are as follows. The sequences of the estimated CDRs are shown in SEQ ID NO: 81 to 206, respectively.

TABLE 6

Heavy chain variable region in amino acid sequence of each heavy chain and light chain variable region in amino acid sequence of each light chain

| SEQ ID NO | H chain/L chain | Variable region |
|---|---|---|
| 14 | H chain | 20Q-240R |
| 15 | L chain | 21D-238K |
| 16 | H chain | 20E-235R |
| 17 | L chain | 21D-239K |
| 39 | H chain | 20E-138S |
| 40 | L chain | 25D-133A |
| 41 | H chain | 20D-236R |
| 42 | L chain | 21D-237N |
| 43 | H chain | 20D-236R |
| 44 | L chain | 21N-237N |
| 45 | H chain | 20Q-234R |
| 46 | L chain | 21D-239C |
| 47 | H chain | 20E-236R |
| 48 | L chain | 23D-283N |
| 49 | H chain | 20Q-249I |
| 50 | L chain | 21D-239C |
| 51 | H chain | 20E-238R |
| 52 | L chain | 25D-210R |
| 53 | H chain | N.D. |
| 54 | L chain | 20D-286C |
| 55 | H chain | 20D-236R |
| 56 | L chain | 21D-237N |
| 57 | H chain | 20D-236R |
| 58 | L chain | 21D-288N |
| 59 | H chain | 20E-239P |
| 60 | L chain | 20D-210R |
| 61 | H chain | 20D-236R |
| 62 | L chain | 21D-237N |
| 63 | H chain | 20E-234E |
| 64 | L chain | 20D-235R |
| 65 | H chain | 20E-234E |
| 66 | L chain | 20D-235R |
| 67 | H chain | 20E-238R |
| 68 | L chain | 25D-235R |
| 69 | H chain | 29E-245R |
| 70 | L chain | 21D-237N |
| 71 | H chain | 20E-234V |

TABLE 6-continued

Heavy chain variable region in amino acid sequence of each heavy chain and light chain variable region in amino acid sequence of each light chain

| SEQ ID NO | H chain/L chain | Variable region |
|---|---|---|
| 72 | L chain | 20D-235R |
| 73 | H chain | 20Q-249I |
| 74 | L chain | 21D-240C |
| 75 | H chain | 20E-239R |
| 76 | L chain | 20D-238C |
| 77 | H chain | 20D-236R |
| 78 | L chain | 21D-237N |
| 79 | H chain | 20E-238R |
| 80 | L chain | 25D-235R |

In the table, each of the heavy chain variable region and the light chain variable region in each amino acid sequence is indicated by the first amino acid and the last amino acid of the region.

For example, the variable region in the amino acid sequence of SEQ ID NO: 14 (H chain, that is, the heavy chain) is a region in a length of 221 amino acids from 22Q to 240R. Since each amino acid sequence shown in Table 6 is an amino acid sequence of an entirety of the heavy and light chains (including a signal sequence), a "heavy chain variable region comprising an amino acid sequence of SEQ ID NO: n" means a heavy chain variable region comprising an amino acid sequence of a heavy chain variable region of SEQ ID NO: n, and a "light chain variable region comprising an amino acid sequence of SEQ ID NO: m" means a light chain variable region comprising an amino acid sequence of a light chain variable region of SEQ ID NO: m". Several amino acids of an amino acid sequence at an end of each variable region may include one or more amino acid mutations selected from the group consisting of additions, deletions, eliminations, and substitutions. The amino acid numbers of the heavy variable region of SEQ ID NO: 53 are not yet determined. The CDRs of SEQ ID NOs: 123 to 125 are indicated with several Xs in the sequence listing but are not yet estimated, and the number of Xs shown in the sequence listing is not related to the lengths of the CDRs.

SEQ ID NO: 1: Human c-erb-B-2 (HER2) base sequence (Genebank accession number: X03363)

SEQ ID NO: 2: Human c-erb-B-2 (HER2) amino acid sequence (UniprotKB ID: P04626)

SEQ ID NO:3: Human c-erb-B-2 (HER2) ec (extracellular domain-secreted) amino acid sequence (23-652aa)

SEQ ID NO: 4: Primer (InF.HindIII-H2-214H)

SEQ ID NO: 5: Primer (InF.HindIII-H2-250H)

SEQ ID NO: 6: primer (InFr.IgG1 terNotI)

SEQ ID NO: 7: Primer (InF.HindIII-H2-214L)

SEQ ID NO: 8: Primer (InF.HindIII-H2-250L)

SEQ ID NO: 9: primer (InF.mIgCKterNotI)

SEQ ID NO: 10: Base sequence of DNA encoding H chain of H$_2$Mab-214 antibody

SEQ ID NO: 11: Base sequence of DNA encoding L chain of H$_2$Mab-214 antibody

SEQ ID NO: 12: Base sequence of DNA encoding H chain of H$_2$Mab-250 antibody

SEQ ID NO: 13: Base sequence of DNA encoding L chain of H$_2$Mab-250 antibody

SEQ ID NO: 14: H-chain amino acid sequence of H$_2$Mab-214 antibody

SEQ ID NO: 15: L-chain amino acid sequence of H$_2$Mab-214 antibody

SEQ ID NO: 16: H-chain amino acid sequence of H$_2$Mab-250 antibody

SEQ ID NO: 17: L-chain amino acid sequence of H₂Mab-250 antibody
SEQ ID NO: 18: Amino acid sequence of H-chain CDR1 of H₂Mab-214 antibody
SEQ ID NO: 19: Amino acid sequence of H-chain CDR2 of H₂Mab-214 antibody
SEQ ID NO: 20: Amino acid sequence of H-chain CDR3 of H₂Mab-214 antibody
SEQ ID NO: 21: Amino acid sequence of L-chain CDR1 of H₂Mab-214 antibody
SEQ ID NO: 22: Amino acid sequence of L-chain CDR2 of H₂Mab-214 antibody
SEQ ID NO: 23: Amino acid sequence of L-chain CDR3 of H₂Mab-214 antibody
SEQ ID NO: 24: Amino acid sequence of amino acid sequence of H-chain CDR1 of H₂Mab-250 antibody
SEQ ID NO: 25: Amino acid sequence of H-chain CDR2 of H₂Mab-250 antibody
SEQ ID NO: 26: Amino acid sequence of H-chain CDR3 of H₂Mab-250 antibody
SEQ ID NO: 27: Amino acid sequence of L-chain CDR1 of H₂Mab-250 antibody
SEQ ID NO: 28: Amino acid sequence of L-chain CDR2 of H₂Mab-250 antibody
SEQ ID NO: 29: Amino acid sequence of L-chain CDR3 of H₂Mab-250 antibody
SEQ ID NO: 30: Amino acid sequence of amino acid numbers 600 to 652 of human HER2 of SEQ ID NO: 2
SEQ ID NO: 31: Amino acid sequence of amino acid numbers 603 to 622 of human HER2 of SEQ ID NO: 2
SEQ ID NO: 32: Amino acid sequence of amino acid numbers 613 to 632 of human HER2 of SEQ ID NO: 2
SEQ ID NO: 33: Amino acid sequence of amino acid numbers 613 to 622 of human HER2 of SEQ ID NO: 2
SEQ ID NO: 34: Amino acid sequence of amino acid numbers 611 to 618 of human HER2 of SEQ ID NO: 2
SEQ ID NO: 35: Amino acid sequence of amino acid numbers 612 to 618 of human HER2 of SEQ ID NO: 2
SEQ ID NO: 36: Amino acid sequence of amino acid numbers 613 to 619 of human HER2 of SEQ ID NO: 2
SEQ ID NO: 37: Amino acid sequence of HER2p604-622C
SEQ ID NO: 38: Exemplary linker used in scFv
SEQ ID NO: 39: H-chain amino acid sequence of H₂Mab-279 antibody
SEQ ID NO: 40: L-chain amino acid sequence of H₂Mab-279 antibody
SEQ ID NO: 41: H-chain amino acid sequence of H₂Mab-280 antibody
SEQ ID NO: 42: L-chain amino acid sequence of H₂Mab-280 antibody
SEQ ID NO: 43: H-chain amino acid sequence of H₂Mab-281 antibody
SEQ ID NO: 44: L-chain amino acid sequence of H₂Mab-281 antibody
SEQ ID NO: 45: H-chain amino acid sequence of H₂Mab-282 antibody
SEQ ID NO: 46: L-chain amino acid sequence of H₂Mab-282 antibody
SEQ ID NO: 47: H-chain amino acid sequence of H₂Mab-283 antibody
SEQ ID NO: 48: L-chain amino acid sequence of H₂Mab-283 antibody
SEQ ID NO: 49: H-chain amino acid sequence of H₂Mab-284 antibody
SEQ ID NO: 50: L-chain amino acid sequence of H₂Mab-284 antibody
SEQ ID NO: 51: H-chain amino acid sequence of H₂Mab-285 antibody
SEQ ID NO: 52: L-chain amino acid sequence of H₂Mab-285 antibody
SEQ ID NO: 53: H-chain amino acid sequence of H₂Mab-286 antibody
SEQ ID NO: 54: L-chain amino acid sequence of H₂Mab-286 antibody
SEQ ID NO: 55: H-chain amino acid sequence of H₂Mab-287 antibody
SEQ ID NO: 56: L-chain amino acid sequence of H₂Mab-287 antibody
SEQ ID NO: 57: H-chain amino acid sequence of H₂Mab-288 antibody
SEQ ID NO: 58: L-chain amino acid sequence of H₂Mab-288 antibody
SEQ ID NO: 59: H-chain amino acid sequence of H₂Mab-289 antibody
SEQ ID NO: 60: L-chain amino acid sequence of H₂Mab-289 antibody
SEQ ID NO: 61: H-chain amino acid sequence of H₂Mab-290 antibody
SEQ ID NO: 62: L-chain amino acid sequence of H₂Mab-290 antibody
SEQ ID NO: 63: H-chain amino acid sequence of H₂Mab-291 antibody
SEQ ID NO: 64: L-chain amino acid sequence of H₂Mab-291 antibody
SEQ ID NO: 65: H-chain amino acid sequence of H₂Mab-292 antibody
SEQ ID NO: 66: L-chain amino acid sequence of H₂Mab-292 antibody
SEQ ID NO: 67: H-chain amino acid sequence of H₂Mab-293 antibody
SEQ ID NO: 68: L-chain amino acid sequence of H₂Mab-293 antibody
SEQ ID NO: 69: H-chain amino acid sequence of H₂Mab-294 antibody
SEQ ID NO: 70: L-chain amino acid sequence of H₂Mab-294 antibody
SEQ ID NO: 71: H-chain amino acid sequence of H₂Mab-295 antibody
SEQ ID NO: 72: L-chain amino acid sequence of H₂Mab-295 antibody
SEQ ID NO: 73: H-chain amino acid sequence of H₂Mab-296 antibody
SEQ ID NO: 74: L-chain amino acid sequence of H₂Mab-296 antibody
SEQ ID NO: 75: H-chain amino acid sequence of H₂Mab-297 antibody
SEQ ID NO: 76: L-chain amino acid sequence of H₂Mab-297 antibody
SEQ ID NO: 77: H-chain amino acid sequence of H₂Mab-298 antibody
SEQ ID NO: 78: L-chain amino acid sequence of H₂Mab-298 antibody
SEQ ID NO: 79: H-chain amino acid sequence of H₂Mab-299 antibody SEQ ID NO: 80: L-chain amino acid sequence of H$_2$Mab-299 antibody
SEQ ID NO: 81: Amino acid sequence of H-chain CDR1 of H$_2$Mab-279 antibody
SEQ ID NO: 82: Amino acid sequence of H-chain CDR2 of H$_2$Mab-279 antibody
SEQ ID NO: 83: Amino acid sequence of H-chain CDR3 of H$_2$Mab-279 antibody
SEQ ID NO: 84: Amino acid sequence of L-chain CDR1 of H$_2$Mab-279 antibody
SEQ ID NO: 85: Amino acid sequence of L-chain CDR2 of H$_2$Mab-279 antibody
SEQ ID NO: 86: Amino acid sequence of L-chain CDR3 of H$_2$Mab-279 antibody
SEQ ID NO: 87: Amino acid sequence of H-chain CDR1 of H$_2$Mab-280 antibody
SEQ ID NO: 88: Amino acid sequence of H-chain CDR2 of H$_2$Mab-280 antibody
SEQ ID NO: 89: Amino acid sequence of H-chain CDR3 of H$_2$Mab-280 antibody
SEQ ID NO: 90: Amino acid sequence of L-chain CDR1 of H$_2$Mab-280 antibody
SEQ ID NO: 91: Amino acid sequence of L-chain CDR2 of H$_2$Mab-280 antibody
SEQ ID NO: 92: Amino acid sequence of L-chain CDR3 of H$_2$Mab-280 antibody
SEQ ID NO: 93: Amino acid sequence of H-chain CDR1 of H$_2$Mab-281 antibody
SEQ ID NO: 94: Amino acid sequence of H-chain CDR2 of H$_2$Mab-281 antibody
SEQ ID NO: 95: Amino acid sequence of H-chain CDR3 of H$_2$Mab-281 antibody
SEQ ID NO: 96: Amino acid sequence of L-chain CDR1 of H$_2$Mab-281 antibody
SEQ ID NO: 97: Amino acid sequence of L-chain CDR2 of H$_2$Mab-281 antibody
SEQ ID NO: 98: Amino acid sequence of L-chain CDR3 of H$_2$Mab-281 antibody
SEQ ID NO: 99: Amino acid sequence of H-chain CDR1 of H$_2$Mab-282 antibody
SEQ ID NO: 100: Amino acid sequence of H-chain CDR2 of H$_2$Mab-282 antibody
SEQ ID NO: 101: Amino acid sequence of H-chain CDR3 of H$_2$Mab-282 antibody
SEQ ID NO: 102: Amino acid sequence of L-chain CDR1 of H$_2$Mab-282 antibody
SEQ ID NO: 103: Amino acid sequence of L-chain CDR2 of H$_2$Mab-282 antibody
SEQ ID NO: 104: Amino acid sequence of L-chain CDR3 of H$_2$Mab-282 antibody
SEQ ID NO: 105: Amino acid sequence of H-chain CDR1 of H$_2$Mab-283 antibody
SEQ ID NO: 106: Amino acid sequence of H-chain CDR2 of H$_2$Mab-283 antibody
SEQ ID NO: 107: Amino acid sequence of H-chain CDR3 of H$_2$Mab-283 antibody
SEQ ID NO: 108: Amino acid sequence of L-chain CDR1 of H$_2$Mab-283 antibody
SEQ ID NO: 109: Amino acid sequence of L-chain CDR2 of H$_2$Mab-283 antibody
SEQ ID NO: 110: Amino acid sequence of L-chain CDR3 of H$_2$Mab-283 antibody
SEQ ID NO: 111: Amino acid sequence of H-chain CDR1 of H$_2$Mab-284 antibody
SEQ ID NO: 112: Amino acid sequence of H-chain CDR2 of H$_2$Mab-284 antibody
SEQ ID NO: 113: Amino acid sequence of H-chain CDR3 of H$_2$Mab-284 antibody
SEQ ID NO: 114: Amino acid sequence of L-chain CDR1 of H$_2$Mab-284 antibody
SEQ ID NO: 115: Amino acid sequence of L-chain CDR2 of H$_2$Mab-284 antibody
SEQ ID NO: 116: Amino acid sequence of L-chain CDR3 of H$_2$Mab-284 antibody
SEQ ID NO: 117: Amino acid sequence of H-chain CDR1 of H$_2$Mab-285 antibody
SEQ ID NO: 118: Amino acid sequence of H-chain CDR2 of H$_2$Mab-285 antibody
SEQ ID NO: 119: Amino acid sequence of H-chain CDR3 of H$_2$Mab-285 antibody
SEQ ID NO: 120: Amino acid sequence of L-chain CDR1 of H$_2$Mab-285 antibody
SEQ ID NO: 121: Amino acid sequence of L-chain CDR2 of H$_2$Mab-285 antibody
SEQ ID NO: 122: Amino acid sequence of L-chain CDR3 of H$_2$Mab-285 antibody
SEQ ID NO: 123: Amino acid sequence of H-chain CDR1 of H$_2$Mab-286 antibody
SEQ ID NO: 124: Amino acid sequence of H-chain CDR2 of H$_2$Mab-286 antibody
SEQ ID NO: 125: Amino acid sequence of H-chain CDR3 of H$_2$Mab-286 antibody
SEQ ID NO: 126: Amino acid sequence of L-chain CDR1 of H$_2$Mab-286 antibody
SEQ ID NO: 127: Amino acid sequence of L-chain CDR2 of H$_2$Mab-286 antibody
SEQ ID NO: 128: Amino acid sequence of L-chain CDR3 of H$_2$Mab-286 antibody
SEQ ID NO: 129: Amino acid sequence of H-chain CDR1 of H$_2$Mab-287 antibody
SEQ ID NO: 130: Amino acid sequence of H-chain CDR2 of H$_2$Mab-287 antibody
SEQ ID NO: 131: Amino acid sequence of H-chain CDR3 of H$_2$Mab-287 antibody
SEQ ID NO: 132: Amino acid sequence of L-chain CDR1 of H$_2$Mab-287 antibody
SEQ ID NO: 133: Amino acid sequence of L-chain CDR2 of H$_2$Mab-287 antibody
SEQ ID NO: 134: Amino acid sequence of L-chain CDR3 of H$_2$Mab-287 antibody
SEQ ID NO: 135: Amino acid sequence of H-chain CDR1 of H$_2$Mab-288 antibody
SEQ ID NO: 136: Amino acid sequence of H-chain CDR2 of H$_2$Mab-288 antibody
SEQ ID NO: 137: Amino acid sequence of H-chain CDR3 of H$_2$Mab-288 antibody
SEQ ID NO: 138: Amino acid sequence of L-chain CDR1 of H$_2$Mab-288 antibody
SEQ ID NO: 139: Amino acid sequence of L-chain CDR2 of H$_2$Mab-288 antibody
SEQ ID NO: 140: Amino acid sequence of L-chain CDR3 of H$_2$Mab-288 antibody
SEQ ID NO: 141: Amino acid sequence of H-chain CDR1 of H$_2$Mab-289 antibody
SEQ ID NO: 142: Amino acid sequence of H-chain CDR2 of H$_2$Mab-289 antibody
SEQ ID NO: 143: Amino acid sequence of H-chain CDR3 of H$_2$Mab-289 antibody
SEQ ID NO: 144: Amino acid sequence of L-chain CDR1 of H$_2$Mab-289 antibody
SEQ ID NO: 145: Amino acid sequence of L-chain CDR2 of H$_2$Mab-289 antibody SEQ ID NO: 146: Amino acid sequence of L-chain CDR3 of H₂Mab-289 antibody
SEQ ID NO: 147: Amino acid sequence of H-chain CDR1 of H₂Mab-290 antibody
SEQ ID NO: 148: Amino acid sequence of H-chain CDR2 of H₂Mab-290 antibody
SEQ ID NO: 149: Amino acid sequence of H-chain CDR3 of H₂Mab-290 antibody
SEQ ID NO: 150: Amino acid sequence of L-chain CDR1 of H₂Mab-290 antibody
SEQ ID NO: 151: Amino acid sequence of L-chain CDR2 of H₂Mab-290 antibody
SEQ ID NO: 152: Amino acid sequence of L-chain CDR3 of H₂Mab-290 antibody
SEQ ID NO: 153: Amino acid sequence of H-chain CDR1 of H₂Mab-291 antibody
SEQ ID NO: 154: Amino acid sequence of H-chain CDR2 of H₂Mab-291 antibody
SEQ ID NO: 155: Amino acid sequence of H-chain CDR3 of H₂Mab-291 antibody
SEQ ID NO: 156: Amino acid sequence of L-chain CDR1 of H₂Mab-291 antibody
SEQ ID NO: 157: Amino acid sequence of L-chain CDR2 of H₂Mab-291 antibody
SEQ ID NO: 158: Amino acid sequence of L-chain CDR3 of H₂Mab-291 antibody
SEQ ID NO: 159: Amino acid sequence of H-chain CDR1 of H₂Mab-292 antibody
SEQ ID NO: 160: Amino acid sequence of H-chain CDR2 of H₂Mab-292 antibody
SEQ ID NO: 161: Amino acid sequence of H-chain CDR3 of H₂Mab-292 antibody
SEQ ID NO: 162: Amino acid sequence of L-chain CDR1 of H₂Mab-292 antibody
SEQ ID NO: 163: Amino acid sequence of L-chain CDR2 of H₂Mab-292 antibody
SEQ ID NO: 164: Amino acid sequence of L-chain CDR3 of H₂Mab-292 antibody
SEQ ID NO: 165: Amino acid sequence of H-chain CDR1 of H₂Mab-293 antibody
SEQ ID NO: 166: Amino acid sequence of H-chain CDR2 of H₂Mab-293 antibody
SEQ ID NO: 167: Amino acid sequence of H-chain CDR3 of H₂Mab-293 antibody
SEQ ID NO: 168: Amino acid sequence of L-chain CDR1 of H₂Mab-293 antibody
SEQ ID NO: 169: Amino acid sequence of L-chain CDR2 of H₂Mab-293 antibody
SEQ ID NO: 170: Amino acid sequence of L-chain CDR3 of H₂Mab-293 antibody
SEQ ID NO: 171: Amino acid sequence of H-chain CDR1 of H₂Mab-294 antibody
SEQ ID NO: 172: Amino acid sequence of H-chain CDR2 of H₂Mab-294 antibody
SEQ ID NO: 173: Amino acid sequence of H-chain CDR3 of H₂Mab-294 antibody
SEQ ID NO: 174: Amino acid sequence of L-chain CDR1 of H₂Mab-294 antibody
SEQ ID NO: 175: Amino acid sequence of L-chain CDR2 of H₂Mab-294 antibody
SEQ ID NO: 176: Amino acid sequence of L-chain CDR3 of H₂Mab-294 antibody
SEQ ID NO: 177: Amino acid sequence of H-chain CDR1 of H₂Mab-295 antibody
SEQ ID NO: 178: Amino acid sequence of H-chain CDR2 of H₂Mab-295 antibody
SEQ ID NO: 179: Amino acid sequence of H-chain CDR3 of H₂Mab-295 antibody
SEQ ID NO: 180: Amino acid sequence of L-chain CDR1 of H₂Mab-295 antibody
SEQ ID NO: 181: Amino acid sequence of L-chain CDR2 of H₂Mab-295 antibody
SEQ ID NO: 182: Amino acid sequence of L-chain CDR3 of H₂Mab-295 antibody
SEQ ID NO: 183: Amino acid sequence of H-chain CDR1 of H₂Mab-296 antibody
SEQ ID NO: 184: Amino acid sequence of H-chain CDR2 of H₂Mab-296 antibody
SEQ ID NO: 185: Amino acid sequence of H-chain CDR3 of H₂Mab-296 antibody
SEQ ID NO: 186: Amino acid sequence of L-chain CDR1 of H₂Mab-296 antibody
SEQ ID NO: 187: Amino acid sequence of L-chain CDR2 of H₂Mab-296 antibody
SEQ ID NO: 188: Amino acid sequence of L-chain CDR3 of H₂Mab-296 antibody
SEQ ID NO: 189: Amino acid sequence of H-chain CDR1 of H₂Mab-297 antibody
SEQ ID NO: 190: Amino acid sequence of H-chain CDR2 of H₂Mab-297 antibody
SEQ ID NO: 191: Amino acid sequence of H-chain CDR3 of H₂Mab-297 antibody
SEQ ID NO: 192: Amino acid sequence of L-chain CDR1 of H₂Mab-297 antibody
SEQ ID NO: 193: Amino acid sequence of L-chain CDR2 of H₂Mab-297 antibody
SEQ ID NO: 194: Amino acid sequence of L-chain CDR3 of H₂Mab-297 antibody
SEQ ID NO: 195: Amino acid sequence of H-chain CDR1 of H₂Mab-298 antibody
SEQ ID NO: 196: Amino acid sequence of H-chain CDR2 of H₂Mab-298 antibody
SEQ ID NO: 197: Amino acid sequence of H-chain CDR3 of H₂Mab-298 antibody
SEQ ID NO: 198: Amino acid sequence of L-chain CDR1 of H₂Mab-298 antibody
SEQ ID NO: 199: Amino acid sequence of L-chain CDR2 of H₂Mab-298 antibody
SEQ ID NO: 200: Amino acid sequence of L-chain CDR3 of H₂Mab-298 antibody
SEQ ID NO: 201: Amino acid sequence of H-chain CDR1 of H₂Mab-299 antibody
SEQ ID NO: 202: Amino acid sequence of H-chain CDR2 of H₂Mab-299 antibody
SEQ ID NO: 203: Amino acid sequence of H-chain CDR3 of H₂Mab-299 antibody
SEQ ID NO: 204: Amino acid sequence of L-chain CDR1 of H₂Mab-299 antibody
SEQ ID NO: 205: Amino acid sequence of L-chain CDR2 of H₂Mab-299 antibody
SEQ ID NO: 206: Amino acid sequence of L-chain CDR3 of H₂Mab-299 antibody

INDUSTRIAL APPLICABILITY

The antibody or antigen-binding fragment thereof of the present invention is useful for the detection and/or treatment of cancer.

SEQUENCE LISTING

```
Sequence total quantity: 206
SEQ ID NO: 1              moltype = DNA   length = 4473
FEATURE                   Location/Qualifiers
source                    1..4473
                          mol_type = other DNA
                          organism = Homo sapiens
SEQUENCE: 1
aaggggaggt aaccctggcc cctttggtcg gggccccggg cagccgcgcg cccctcccca   60
cggggccctt tactgcgccg cgcgcccggc cccacccct cgcagcaccc cgcgccccgc   120
gccctcccag ccgggtccag ccggagccat ggggccggag ccgcagtgag caccatggag   180
ctggcggcct tgtgccgctg ggggctcctc ctcgccctct tgccccccgg agccgcgagc   240
acccaagtgt gcaccggcac agacatgaag ctgcggctcc ctgccagtcc cgagaccac   300
ctggacatgc tccgccacct ctaccagggc tgcaggtgg tgcagggaaa cctggaactc   360
acctacctgc ccaccaatgc cagcctgtcc ttcctgcagg atatccagga ggtgcagggc   420
tacgtgctca tcgctcacaa ccaagtgagg caggtccgac tgcagaggct gcggattgtg   480
cgaggcaccc agctctttga ggacaactat gccctggccg tgctagacaa tggagacccg   540
ctgaacaata ccaccctgt cacaggggcc tccccaggag gcctgcggga gctgcagctt   600
cgaagcctca cagagatctt gaaggaggg gtcttgatcc agcggaaccc ccagctctgc   660
taccaggaca cgattttgtg gaaggacatc ttccacaaga acaaccagct ggctctcaca   720
ctgatagaca ccaaccgctc tcgggcctgc caccctgtt ctccgatgtg taagggctcc   780
cgctgctggg gagagagttc tgaggattgt cagagcctga cgcgcactgt ctgtgccggt   840
ggctgtgccc gctgcaaggg gccactgcc actgactgct gccatgagca gtgtgctgcc   900
ggctgcacgg gccccaagca ctctgactgc ctggcctgcc tccacttcaa ccacagtggc   960
atctgtgagc tgcactgccc agccctggtc acctacaaca cagacacgtt tgagtccatg   1020
cccaatcccg agggccggta tacattcggc gccagctgtg tgactgcctg tccctacaac   1080
tacctttcta cggacgtggg atcctgcacc ctcgtctgcc cctgcacaa ccaagaggtg   1140
acagcagaga atgaacaca gcggtgtgag aagtgcagca gccctgtgc ccgagtgtgc   1200
tatgtctgg gcatggagca cttgcgagag gtgagggcag ttaccagtgc caatatccag   1260
gagtttgctg gctgcaagaa gatctttggg agcctggcat ttctgccgga gagctttgat   1320
ggggacccag cctccaacac tgccccgctc agccagagc agctccaagt gtttgagact   1380
ctggaagaga tcacaggtta cctatacatc tcagcatggc cggacagcct gcctgacctc   1440
agcgtcttcc agaacctgca agtaatccgg ggacaattc tgcacaatgg cgcctactgg   1500
ctgacccctc aagggctggg catcagctgg ctggggctgc gctcactgag ggaactgggc   1560
agtggactgg ccctcatcca cataacacc cacctctgct tcgtcacac ggtgccctgg   1620
gaccagctct ttcggaaccc gcaccaagct ctgctccaca ctgccaaccg gccagaggac   1680
gagtgtgtgg gcgagggcct ggcctgccac cagctgtgcg cccgagggca ctgctgggt   1740
ccagggccca cccagtgtgt caactgcagc cagttcctc ggggcaggga gtgcgtggag   1800
gaatgccgag tactgcaggg gctccccagg gagtatgtga atgccaggca ctgtttgccg   1860
tgccaccctg agtgtcagcc ccagaatggc tcagtgacct gttttggacc ggaggctgac   1920
cagtgtgtgg cctgtgccca ctataaggac cctccttct gcgtggcccg ctgccccagc   1980
ggtgtgaaac ctgacctctc ctacatgccc atctggaagt ttccagatga ggagggcgca   2040
tgccagcctt gccccatcaa ctgcacccac tcctgtgtgg acctggatga caagggctgc   2100
cccgccgagc agagagccag ccctctgacg tccatcatct ctgcggtggt tggcattctg   2160
ctggtcgtgg tcttggggt ggtctttggg atcctcatca agcgacggca gcagaagatc   2220
cggaagtaca cgatgcggag actgctgcag gaaacggagc tggtggagcc gctgacacct   2280
agcggagcga tgcccaacca ggcgcagatg cggatcctga aagagacgga gctgaggaag   2340
gtgaaggtgc ttgatctgg cgcttttggc acagtctaca gggcatctg atccctgat   2400
gggagaaatg tgaaattcc agtggccatc aaagtgttga gggaaaacac atcccccaaa   2460
gccaacaaag aaatcttaga cgaagcatac gtgatggctg gtgtgggctc cccatatgtc   2520
tcccgccttc tgggcatctg cctgacatcc acggtgcagc tggtgacaca gcttatgccc   2580
tatgctgcc tcttagacca tgtccgggaa aaccgcggac gctgggctc caggacctg   2640
ctgaactggt gtatgcagat tgccaagggg atgagctacc tggaggatgt gcggctcgta   2700
cacagggact tggccgctcg gaacgtgctg gtcaagagtc ccaaccatgt caaaattaca   2760
gacttcgggc tggctcggct gctggacatt gacgagacag agtaccatgc agatgggggc   2820
aaggtgccca tcaagtggat ggcgctggag tccattctcc gccggcggtt cacccaccag   2880
agtgatgtgt ggagttatgg tgtgactgtg tgggagctga tgacttttgg gccaaacct   2940
tacgatggga tcccagcccg ggagatccct gacctgctga aaaggggga gcggctgccc   3000
cagccccca tctgcaccat tgatgtctac atgatcatgg tcaaatgttg gatgattgac   3060
tctgaatgtc ggccaagatt ccgggagttg gtgtctgaat tctcccgcat ggccaggga   3120
ccccagcgct ttgtggtcat ccagaatgag gacttgggcc cagccagtcc cttggacagc   3180
accttctacc gctcactgct ggaggacgat gacatggggga acctggtgga tgctgaggag   3240
tatctggtac cccagcaggg cttcttctgt ccagaccctg ccccgggcgc tggggcatg   3300
gtccaccaca ggcaccgcag ctcatctacc aggagtggcg gtgggacct gacactaggg   3360
ctggagccct ctgaagagga ggcccccagg tctccactgg caccctccga aggggctggc   3420
tccgatgtat ttgatggtga cctgggaatg ggggcagca aggggctgca aagcctcccc   3480
acacatgacc ccagccctct acagcggtac agtgaggacc ccacagtacc ctgccctct   3540
gagactgatg gctacgttgc ccccctgacc tgcagcccc agcctgaata tgtgaaccag   3600
ccagatgttc ggccccagcc cccttcgccc agagggggc tctgcctgc tgcccgacct   3660
gctggtgcca ctctggaaag gcccaagact ctctcccag ggaagaatgg ggtcgtcaa   3720
gacgtttttg cctttggggg tgccgtggag aaccccgagt acttgacacc ccagggagga   3780
gctgcccctc agcccaccc tcctcctgcc ttcagcccag ccttgacaa cctctattac   3840
tgggaccagg acccaccaga gcgggggct ccacccagca ccttcaaagg gacacctacg   3900
gcagagaacc cagagtacct gggtctggac gtgccagtgg aaaccagaag gccagctgcc   3960
cagaagccct gatgtgtcct cagggagcag ggaaggcctg acttctgctg gcatcaagag   4020
gtgggagggc cctccgacca cttccagggg aacctgccat gccaggaacc tgtcctaagg   4080
aaccttcctt cctgcttgag ttcccagatg gctggaggg gtccagcctc gttgaagag   4140
gaacagcact ggggagtctt tgtggattct gaggccctgc ccaatgagac tctagggtcc   4200
agtggatgcc acagcccagc ttggcccttt ccttccagat cctgggtact gaaagcctta   4260
```

-continued

```
gggaagctgg  cctgagaggg  gaagcggccc  taagggagtg  tctaagaaca  aaagcgaccc   4320
attcagagac  tgtccctgaa  acctagtact  gcccccatg   aggaaggaac  agcaatggtg   4380
tcagtatcca  ggctttgtac  agagtgcttt  tctgtttagt  ttttacttt   tttgttttgt   4440
tttttaaag   atgaaataaa  gacccagggg  gag                                  4473
```

```
SEQ ID NO: 2              moltype = AA   length = 1255
FEATURE                   Location/Qualifiers
source                    1..1255
                          mol_type = protein
                          organism = Homo sapiens
SEQUENCE: 2
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA 1020
EEYLVPQQGF FCPDPAPGAG GMVHHRHRSS STRSGGGDLT LGLEPSEEEA PRSPLAPSEG 1080
AGSDVFDGDL GMGAAKGLQS LPTHDPSPLQ RYSEDPTVPL PSETDGYVAP LTCSPQPEYV 1140
NQPDVRPQPP SPREGPLPAA RPAGATLERP KTLSPKGNGV VKDVFAFGGA VENPEYLTPQ 1200
GGAAPQPHPP PAFSPAFDNL YYWDQDPPER GAPPSTFKGT PTAENPEYLG LDVPV      1255
```

```
SEQ ID NO: 3              moltype = AA   length = 630
FEATURE                   Location/Qualifiers
REGION                    1..630
                          note = HER2ec
source                    1..630
                          mol_type = protein
                          organism = synthetic construct
SEQUENCE: 3
TQVCTGTDMK LRLPASPETH LDMLRHLYQG CQVVQGNLEL TYLPTNASLS FLQDIQEVQG   60
YVLIAHNQVR QVPLQRLRIV RGTQLFEDNY ALAVLDNGDP LNNTTPVTGA SPGGLRELQL  120
RSLTEILKGG VLIQRNPQLC YQDTILWKDI FHKNNQLALT LIDTNRSRAC HPCSPMCKGS  180
RCWGESSEDC QSLTRTVCAG GCARCKGPLP TDCCHEQCAA GCTGPKHSDC LACLHFNHSG  240
ICELHCPALV TYNTDTFESM PNPEGRYTFG ASCVTACPYN YLSTDVGSCT LVCPLHNQEV  300
TAEDGTQRCE KCSKPCARVC YGLGMEHLRE VRAVTSANIQ EFAGCKKIFG SLAFLPESFD  360
GDPASNTAPL QPEQLQVFET LEEITGYLYI SAWPDSLPDL SVFQNLQVIR GRILHNGAYS  420
LTLQGLGISW LGLRSLRELG SGLALIHHNT HLCFVHTVPW DQLFRNPHQA LLHTANRPED  480
ECVGEGLACH QLCARGHCWG PGPTQCVNCS QFLRGQECVE ECRVLQGLPR EYVNARHCLP  540
CHPECQPQNG SVTCFGPEAD QCVACAHYKD PPFCVARCPS GVKPDLSYMP IWKFPDEEGA  600
CQPCPINCTH SCVDLDDKGC PAEQRASPLT                                    630
```

```
SEQ ID NO: 4              moltype = DNA   length = 35
FEATURE                   Location/Qualifiers
misc_feature              1..35
                          note = InF.HindIII-H2-214H
source                    1..35
                          mol_type = other DNA
                          organism = synthetic construct
SEQUENCE: 4
cggtatcgat aagcttgata tggacaggct tactt                               35
```

```
SEQ ID NO: 5              moltype = DNA   length = 35
FEATURE                   Location/Qualifiers
misc_feature              1..35
                          note = InF.HindIII-H2-250H
source                    1..35
                          mol_type = other DNA
                          organism = synthetic construct
SEQUENCE: 5
cggtatcgat aagcttaaca tgaacttagg gctca                               35
```

```
SEQ ID NO: 6              moltype = DNA   length = 34
FEATURE                   Location/Qualifiers
misc_feature              1..34
                          note = InFr.IgG1terNotI
source                    1..34
                          mol_type = other DNA
```

```
                              -continued organism = synthetic construct
SEQUENCE: 6
tctagagtcg cggccgctca tttaccagga gagt                                    34

SEQ ID NO: 7             moltype = DNA   length = 34
FEATURE                  Location/Qualifiers
misc_feature             1..34
                         note = InF.HindIII-H2-214L
source                   1..34
                         mol_type = other DNA
                         organism = synthetic construct
SEQUENCE: 7
cggtatcgat aagcttgaga tggagtcaga caca                                    34

SEQ ID NO: 8             moltype = DNA   length = 35
FEATURE                  Location/Qualifiers
misc_feature             1..35
                         note = InF.HindIII-H2-250L
source                   1..35
                         mol_type = other DNA
                         organism = synthetic construct
SEQUENCE: 8
cggtatcgat aagcttaaaa tgatgagtcc tgccc                                   35

SEQ ID NO: 9             moltype = DNA   length = 34
FEATURE                  Location/Qualifiers
misc_feature             1..34
                         note = InF.mIgCKterNotI
source                   1..34
                         mol_type = other DNA
                         organism = synthetic construct
SEQUENCE: 9
tctagagtcg cggccgccta acactcattc ctgt                                    34

SEQ ID NO: 10            moltype = DNA   length = 1395
FEATURE                  Location/Qualifiers
misc_feature             1..1395
                         note = H2Mab-214 Heavy chain DNA
source                   1..1395
                         mol_type = other DNA
                         organism = synthetic construct
SEQUENCE: 10
atggacaggc ttacttcctc attcctgctg ctgattgtcc ctgcatatgt cctttcccag        60
gttactctga aagagtctgg ccctgggata ttgcagccct ccagaccct cagtctgact        120
tgttctttct ctgggttttc actgagcact tctggtatgg gtgtgagctg gattcgtcag       180
ccttcaggaa agggtctgga gtggctggca cacatttttct gggatgatga caagcgctat       240
aacccatccc tgaagagccg gctcacaatc tccaaggata cctccagaaa taaggtattc       300
ctcaagatca ccagtgtgga cactgcagat actgccacat actactgtgc tcgaagggta       360
gtagctacag actggtactt cgatgtctgg ggcgcaggga ccacggtcac cgtctcctca       420
gccaaaacga caccccatc tgtctatcca ctggcccctg gatctgctgc ccaaactaac        480
tccatggtga cctgggatg cctggtcaag ggctatttc ctgagccagt gacagtgacc        540
tggaactctg gatccctgtc cagcggtgtg cacaccttcc cagctgtcct gcagtctgac       600
ctctacactc tgagcagctc agtgactgtc cctccagca cctggcccag cgagaccgtc       660
acctgcaact tgcccaccc ggccagcagc accaaggtgg acaagaaaat tgtgcccagg        720
gattggtgtt gtaagccttg catatgtaca gtcccagaag tatcatctgt cttcatcttc       780
ccccaaagc caaggatgt gctcaccatt actctgactc taaggtcac gtgtgttgtg         840
gtagacatca gcaaggatga tcccgaggtc cagttcagct ggtttgtaga tgatgttgag       900
gtgcacacag ctcagacgca accccgggag gagcagttca acagcacttt ccgctcagtc      960
agtgaacttc ccatcatgca caggactggc tcaatggca aggagttcaa atgcagggtc     1020
aacagtgcag cttttcctgc ccccatcgag aaaaccatct ccaaaaccaa aggcagaccg    1080
aaggctccac aggtgtacac cattccacct cccaaggagc agatggccaa ggataaagtc    1140
agtctgacct gcatgataac agacttcttc cctgaagaca ttactgtgga gtggcagtgg    1200
aatgggcagc cagcggagaa ctacaagaac actcagccca tcatggacac agatggctct   1260
tacttcgtct acagcaagct caatgtgcag aagagcaact gggaggcagg aaatacttc    1320
acctgctctg tgttacagga gggcctgcac aaccaccata ctgagaagag cctctccac    1380
tctcctggta aatga                                                   1395

SEQ ID NO: 11            moltype = DNA   length = 717
FEATURE                  Location/Qualifiers
misc_feature             1..717
                         note = H2Mab-214 Light chain DNA
source                   1..717
                         mol_type = other DNA
                         organism = synthetic construct
SEQUENCE: 11
atggagtcag acacactcct gctatgggtg ctgctgctct gggttccagg ctccactggt        60
gacattgtgc tcacccaatc tccagcttct ttggctgtgt ctctaggtca gagagccacc       120
atctcctgca gagccagtga aagtgttgaa tattatggca aactttaat gcagtggtac        180
caacagaaac caggacagcc acccaaactc ctcatctatg ctgcatccaa gtagaatct        240
```

-continued

```
ggggtccctg ccaggtttag tggcagtggg tctgggactg acttcagcct caacatccat   300
cctgtggagg aggatgatgt tgcaatgtat ttctgtcagc aaagtaggaa ggttccgctc   360
acgttccgtg ctgggaccaa gctggagctg aaacggctg atgctgcacc aactgtatcc    420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata acagctatac ctgtgaggcc   660
actcacaaga catcaacttc acccattgtc aagagcttca acaggaatga gtgttag     717

SEQ ID NO: 12         moltype = DNA  length = 1380
FEATURE               Location/Qualifiers
misc_feature          1..1380
                      note = H2Mab-250 Heavy chain DNA
source                1..1380
                      mol_type = other DNA
                      organism = synthetic construct
SEQUENCE: 12
atgaacttag ggctcagctt cattttcctt gccctttttt taaaaggtgt ccggtgtgag    60
gtgcagctgg tggagtctgg gggaggctta gtgcagccag agggtccctg gaaactctcc   120
tgtgcagcct ctggattcac tttcagtaac tatggcatgt cttgggttcg ccagactcca   180
gacaggaggc tggagttggt cgcaaccatt aataataatg gtggtggtac ctattatcca   240
gacagtgtga agggccggtt caccatctcc agagacaatg ccaagaacac cctgtacctg   300
caaatgagca gtctgaagtc tgaggacaca gccatgtact actgcacaag ccccggccta   360
ctatgggatg cctggggcgc agggaccacg gtcaccgtct cctcagccaa aacgacaccc   420
ccatctgtct atccactggc cctggatct gctgcccaaa ctaactccat ggtgaccctg    480
ggatgcctgg tcaagggcta tttccctgag ccagtgacag tgacctggaa ctctggatcc   540
ctgtccagcg gtgtgcacac cttcccagct gtcctgcagt ctgacctcta cactctgagc   600
agctcagtga ctgtcccctc cagcacctgg cccagcgaga ccgtcacctg caacgttgcc   660
cacccggcca gcagcaccaa ggtggacaag aaaattgtgc ccagggattg tggttgtaag   720
ccttgcatat gtacagtccc agaagtatca tctgtcttca tcttccccc aaagcccaag   780
gatgtgctca ccattactct gactcctaag gtcacgtgtg ttgtggtaga catcagcaag   840
gatgatcccg aggtccagtt cagctggttt gtagatgatg tggaggtgca cacagctcag   900
acgcaacccc gggaggagca gttcaacagc actttccgct cagtcagtga acttcccatc   960
atgcaccagg actggctcaa tggcaaggag ttcaaatgca gggtcaacag tgcagctttc  1020
cctgccccca tcgagaaaac catctccaaa accaaaggtc gaccgaaggc tccacaggtg  1080
tacaccattc cacctcccaa ggagcagatg gccaaggata agtcagtct gacctgcatg   1140
ataacagact tcttccctga agacattact gtggagtggc agtggaatgg cagccagcg   1200
gagaactaca agaacactca gcccatcatg gacacagatg gctcttactt cgtctacagc   1260
aagctcaatg tgcagaagag caactgggag gcaggaaata ctttcacctg ctctgtgtta  1320
catgagggcc tgcacaacca ccatactgag aagagcctct cccactctcc tggtaaatga  1380

SEQ ID NO: 13         moltype = DNA  length = 720
FEATURE               Location/Qualifiers
misc_feature          1..720
                      note = H2Mab-250 Light chain DNA
source                1..720
                      mol_type = other DNA
                      organism = synthetic construct
SEQUENCE: 13
atgatgagtc ctgcccagtt cctgtttctg ttagtgctct ggattcggga aaccaacggt    60
gatgttgtga tgacccagac tccactcact ttgtcggtct ccattggaca accagcctgc   120
atctcttgca gtcaagtca gagcctctta gatagtgatg gaaggacata tttgaattgg   180
ttgttacaga ggctcaggcca gtccccaaag cgcctaatct atctggtgtc taaactggac   240
tctggagccc ctgacaggtt cactggcagt ggatcaggga cagatttac actgaaaatc    300
agcagagtgg aggctgagga tttgggagtt tattattgct ggcaaggtac acatttttcg   360
cagacgttcg gtggaggcac caagctggaa atcaaacggg ctgatgctgc accaactgta   420
tccatcttcc caccatccag tgagcagtta acatctggag gtgcctcagt cgtgtgcttc   480
ttgaacaact ctaccccaa agacatcaat gtcaagtgga gattgatgg cagtgaacga    540
caaaatggcg tcctgaacag ttggactgat caggacagca aagacagcac ctacagcatg   600
agcagcaccc tcacgttgac caaggacgag tatgaacgac ataacagcta tacctgtgag   660
gccactcaca agacatcaac ttcacccatt gtcaagagct tcaacaggaa tgagtgttag   720

SEQ ID NO: 14         moltype = AA  length = 464
FEATURE               Location/Qualifiers
REGION                1..464
                      note = H2Mab-214 Heavy chain protein
source                1..464
                      mol_type = protein
                      organism = synthetic construct
SEQUENCE: 14
MDRLTSSFLL LIVPAYVLSQ VTLKESGPGI LQPSQTLSLT CSFSGFSLST SGMGVSWIRQ    60
PSGKGLEWLA HIFWDDDKRY NPSLKSRLTI SKDTSRNKVF LKITSVDTAD TATYYCARRV   120
VATDWYFDVW GAGTTVTVSS AKTTPPSVYP LAPGSAAQTN SMVTLGCLVK GYFPEPVTVT   180
WNSGSLSSGV HTFPAVLQSD LYTLSSSVTV PSSTWPSETV TCNVAHPASS TKVDKKIVPR   240
DCGCKPCICT VPEVSSVFIF PPKPKDVLTI TLTPKVTCVV VDISKDDPEV QFSWFVDDVE   300
VHTAQTQPRE EQFNSTFRSV SELPIMHQDW LNGKEFKCRV NSAAFPAPIE KTISKTGRP   360
KAPQVYTIPP PKEQMAKDKV SLTCMITDFF PEDITVEWQW NGQPAENYKN TQPIMDTDGS   420
YFVYSKLNVQ KSNWEAGNTF TCSVLHEGLH NHHTEKSLSH SPGK                    464
```

| | | |
|---|---|---|
| SEQ ID NO: 15 | moltype = AA   length = 238 | |
| FEATURE | Location/Qualifiers | |
| REGION | 1..238 | |
| | note = H2Mab-214 Light chain protein | |
| source | 1..238 | |
| | mol_type = protein | |
| | organism = synthetic construct | |
| SEQUENCE: 15 | | |
| MESDTLLLWV LLLWVPGSTG DIVLTQSPAS LAVSLGQRAT ISCRASESVE YYGTTLMQWY | | 60 |
| QQKPGQPPKL LIYAASKVES GVPARFSGSG SGTDFSLNIH PVEEDDVAMY FCQQSRKVPL | | 120 |
| TFGAGTKLEL KRADAAPTVS IFPPSSEQLT SGGASVVCFL NNFYPKDINV KWKIDGSERQ | | 180 |
| NGVLNSWTDQ DSKDSTYSMS STLTLTKDEY ERHNSYTCEA THKTSTSPIV KSFNRNEC | | 238 |
| | | |
| SEQ ID NO: 16 | moltype = AA   length = 459 | |
| FEATURE | Location/Qualifiers | |
| REGION | 1..459 | |
| | note = H2Mab-250 Heavy chain protein | |
| source | 1..459 | |
| | mol_type = protein | |
| | organism = synthetic construct | |
| SEQUENCE: 16 | | |
| MNLGLSFIFL ALFLKGVRCE VQLVESGGGL VQPGGSLKLS CAASGFTFSN YGMSWVRQTP | | 60 |
| DRRLELVATI NNNGGGTYYP DSVKGRFTIS RDNAKNTLYL QMSSLKSEDT AMYYCTSPGL | | 120 |
| LWDAWGAGTT VTVSSAKTTP PSVYPLAPGS AAQTNSMVTL GCLVKGYFPE PVTVTWNSGS | | 180 |
| LSSGVHTFPA VLQSDLYTLS SSVTVPSSTW PSETVTCNVA HPASSTKVDK KIVPRDCGCK | | 240 |
| PCICTVPEVS SVFIFPPKPK DVLTITLTPK VTCVVVDISK DDPEVQFSWF VDDVEVHTAQ | | 300 |
| TQPREEQFNS TFRSVSELPI MHQDWLNGKE FKCRVNSAAF PAPIEKTISK TKGRPKAPQV | | 360 |
| YTIPPPKEQM AKDKVSLTCM ITDFFPEDIT VEWQWNGQPA ENYKNTQPIM DTDGSYFVYS | | 420 |
| KLNVQKSNWE AGNTFTCSVL HEGLHNHHTE KSLSHSPGK | | 459 |
| | | |
| SEQ ID NO: 17 | moltype = AA   length = 239 | |
| FEATURE | Location/Qualifiers | |
| REGION | 1..239 | |
| | note = H2Mab-250 Light chain protein | |
| source | 1..239 | |
| | mol_type = protein | |
| | organism = synthetic construct | |
| SEQUENCE: 17 | | |
| MMSPAQFLFL LVLWIRETNG DVVMTQTPLT LSVSIGQPAS ISCKSSQSLL DSDGRTYLNW | | 60 |
| LLQRPGQSPK RLIYLVSKLD SGAPDRFTGS GSGTDFTLKI SRVEAEDLGV YYCWQGTHFP | | 120 |
| QTFGGGTKLE IKRADAAPTV SIFPPSSEQL TSGGASVVCF LNNFYPKDIN VKWKIDGSER | | 180 |
| QNGVLNSWTD QDSKDSTYSM SSTLTLTKDE YERHNSYTCE ATHKTSTSPI VKSFNRNEC | | 239 |
| | | |
| SEQ ID NO: 18 | moltype = AA   length = 7 | |
| FEATURE | Location/Qualifiers | |
| REGION | 1..7 | |
| | note = H2Mab-214 HCDR1 | |
| source | 1..7 | |
| | mol_type = protein | |
| | organism = synthetic construct | |
| SEQUENCE: 18 | | |
| TSGMGVS | | 7 |
| | | |
| SEQ ID NO: 19 | moltype = AA   length = 16 | |
| FEATURE | Location/Qualifiers | |
| REGION | 1..16 | |
| | note = H2Mab-214 HCDR2 | |
| source | 1..16 | |
| | mol_type = protein | |
| | organism = synthetic construct | |
| SEQUENCE: 19 | | |
| HIFWDDDKRY NPSLKS | | 16 |
| | | |
| SEQ ID NO: 20 | moltype = AA   length = 11 | |
| FEATURE | Location/Qualifiers | |
| REGION | 1..11 | |
| | note = H2Mab-214 HCDR3 | |
| source | 1..11 | |
| | mol_type = protein | |
| | organism = synthetic construct | |
| SEQUENCE: 20 | | |
| RVVATDWYFD V | | 11 |
| | | |
| SEQ ID NO: 21 | moltype = AA   length = 15 | |
| FEATURE | Location/Qualifiers | |
| REGION | 1..15 | |
| | note = H2Mab-214 LCDR1 | |
| source | 1..15 | |
| | mol_type = protein | |

```
                              -continued

SEQUENCE: 21
RASESVEYYG TTLMQ                                                  15

SEQ ID NO: 22         moltype = AA  length = 7
FEATURE               Location/Qualifiers
REGION                1..7
                      note = H2Mab-214 LCDR2
source                1..7
                      mol_type = protein
                      organism = synthetic construct
SEQUENCE: 22
AASKVES                                                           7

SEQ ID NO: 23         moltype = AA  length = 9
FEATURE               Location/Qualifiers
REGION                1..9
                      note = H2Mab-214 LCDR3
source                1..9
                      mol_type = protein
                      organism = synthetic construct
SEQUENCE: 23
QQSRKVPLT                                                         9

SEQ ID NO: 24         moltype = AA  length = 5
FEATURE               Location/Qualifiers
REGION                1..5
                      note = H2Mab-250 HCDR1
source                1..5
                      mol_type = protein
                      organism = synthetic construct
SEQUENCE: 24
NYGMS                                                             5

SEQ ID NO: 25         moltype = AA  length = 17
FEATURE               Location/Qualifiers
REGION                1..17
                      note = H2Mab-250 HCDR2
source                1..17
                      mol_type = protein
                      organism = synthetic construct
SEQUENCE: 25
TINNNGGGTY YPDSVKG                                                17

SEQ ID NO: 26         moltype = AA  length = 7
FEATURE               Location/Qualifiers
REGION                1..7
                      note = H2Mab-250 HCDR3
source                1..7
                      mol_type = protein
                      organism = synthetic construct
SEQUENCE: 26
PGLLWDA                                                           7

SEQ ID NO: 27         moltype = AA  length = 16
FEATURE               Location/Qualifiers
REGION                1..16
                      note = H2Mab-250 LCDR1
source                1..16
                      mol_type = protein
                      organism = synthetic construct
SEQUENCE: 27
KSSQSLLDSD GRTYLN                                                 16

SEQ ID NO: 28         moltype = AA  length = 7
FEATURE               Location/Qualifiers
REGION                1..7
                      note = H2Mab-250 LCDR2
source                1..7
                      mol_type = protein
                      organism = synthetic construct
SEQUENCE: 28
LVSKLDS                                                           7

SEQ ID NO: 29         moltype = AA  length = 9
FEATURE               Location/Qualifiers
REGION                1..9
                      note = H2Mab-250 LCDR3
source                1..9
```

-continued

```
                              mol_type = protein
                              organism = synthetic construct
SEQUENCE: 29
WQGTHFPQT                                                                    9

SEQ ID NO: 30                 moltype = AA   length = 53
FEATURE                       Location/Qualifiers
REGION                        1..53
                              note = human HER2 600-652
source                        1..53
                              mol_type = protein
                              organism = synthetic construct
SEQUENCE: 30
CPSGVKPDLS YMPIWKFPDE EGACQPCPIN CTHSCVDLDD KGCPAEQRAS PLT                  53

SEQ ID NO: 31                 moltype = AA   length = 20
FEATURE                       Location/Qualifiers
REGION                        1..20
                              note = Human HER2 603-622
source                        1..20
                              mol_type = protein
                              organism = synthetic construct
SEQUENCE: 31
GVKPDLSYMP IWKFPDEEGA                                                       20

SEQ ID NO: 32                 moltype = AA   length = 20
FEATURE                       Location/Qualifiers
REGION                        1..20
                              note = Human HER2 613-632
source                        1..20
                              mol_type = protein
                              organism = synthetic construct
SEQUENCE: 32
IWKFPDEEGA CQPCPINCTH                                                       20

SEQ ID NO: 33                 moltype = AA   length = 10
FEATURE                       Location/Qualifiers
REGION                        1..10
                              note = human HER2 613-622
source                        1..10
                              mol_type = protein
                              organism = synthetic construct
SEQUENCE: 33
IWKFPDEEGA                                                                  10

SEQ ID NO: 34                 moltype = AA   length = 8
FEATURE                       Location/Qualifiers
REGION                        1..8
                              note = human HER2 611-618
source                        1..8
                              mol_type = protein
                              organism = synthetic construct
SEQUENCE: 34
MPIWKFPD                                                                     8

SEQ ID NO: 35                 moltype = AA   length = 7
FEATURE                       Location/Qualifiers
REGION                        1..7
                              note = human HER2 612-618
source                        1..7
                              mol_type = protein
                              organism = synthetic construct
SEQUENCE: 35
PIWKFPD                                                                      7

SEQ ID NO: 36                 moltype = AA   length = 7
FEATURE                       Location/Qualifiers
REGION                        1..7
                              note = human HER2 613-619
source                        1..7
                              mol_type = protein
                              organism = synthetic construct
SEQUENCE: 36
IWKFPDE                                                                      7

SEQ ID NO: 37                 moltype = AA   length = 20
FEATURE                       Location/Qualifiers
REGION                        1..20
                              note = human HER2 p604-622C
```

```
source                  1..20
                        mol_type = protein
                        organism = synthetic construct
SEQUENCE: 37
VKPDLSYMPI WKFPDEEGAC                                                   20

SEQ ID NO: 38           moltype = AA   length = 20
FEATURE                 Location/Qualifiers
REGION                  1..20
                        note = Linker
source                  1..20
                        mol_type = protein
                        organism = synthetic construct
SEQUENCE: 38
GGGGSGGGGS GGGGSGGGGS                                                   20

SEQ ID NO: 39           moltype = AA   length = 463
FEATURE                 Location/Qualifiers
REGION                  1..463
                        note = H2M279 Heavy Chain Protein
source                  1..463
                        mol_type = protein
                        organism = synthetic construct
SEQUENCE: 39
MNLGLSFIFL ALILKGVQCE VQLVESGGGL VQPGGSLKLS CAASGFSFSS YGIFWVRQTP        60
DKRLELVATI KSNGGRTYYP DSVKGRFTIS RDNAKNTLHL QMSSLKSEDT AMYYCAREGG       120
DYWGQGTSVT VSSATTTAPS VYPLVPGCSD TSGSSVTLGC LVKGYFPEPV TVKWNYGALS       180
SGVRTVSSVL QSGFYSLSSL VTVPSSTWPS QTVICNVAHP ASKTELIKRI EPRIPKPSTP       240
PGSSCPPGNI LGGPSVFIFP PKPKDALMIS LTPKVTCVVV DVSEDDPDVH VSWFVDNKEV       300
HTAWTQPREA QYNSTFRVVS ALPIQHQDWM RGKEFKCKVN NKALPAPIER TISKPKGRAQ       360
TPQVYTIPPP REQMSKKKVS LTCLVTNFFS EAISVEWERN GELEQDYKNT PPILDSDGTY       420
FLYSKLTVDT DSWLQGEIFT CSVVHEALHN HHTQKNLSRS PGK                         463

SEQ ID NO: 40           moltype = AA   length = 238
FEATURE                 Location/Qualifiers
REGION                  1..238
                        note = H2M279 Light Chain Protein
source                  1..238
                        mol_type = protein
                        organism = synthetic construct
SEQUENCE: 40
MGIKMETHSQ VFVYMLLWLS GIEGDIVMTQ SHKIMSTSVG DRVSISCKAS QDVGTAVAWY        60
QQKPGQSPIL LIYWASTRHT GVPDRFTGSG SGTDFTLTIS NVQSEDLADY FCQQYKSNPL       120
TFGAGTKLEL KRADAAPTVS IFPPSSEQLT SGGASVVCFL NNFYPKDINV KWKIDGSERQ       180
NGVLNSWTDQ DSKDSTYSMS STLTLTKDEY ERHNSYTCEA THKTSTSPIV KSFNRNEC         238

SEQ ID NO: 41           moltype = AA   length = 457
FEATURE                 Location/Qualifiers
REGION                  1..457
                        note = H2M280 Heavy Chain Protein
source                  1..457
                        mol_type = protein
                        organism = synthetic construct
SEQUENCE: 41
MNFGLRLIFL VLTLKGVQCD VKLVESGGGL VKPGGSLKLS CAASGFTFSS YSMSWVRQTP        60
EKRLEWVAII SSGGSYTFYP DSVKGRFTIS RDNAKNTLYL QMSSLKSEDT AMYHCTREAG       120
DYWGQGTTLT VSSAKTTPPS VYPLAPGSAA QTNSMVTLGC LVKGYFPEPV TVTWNSGSLS       180
SGVHTFPAVL QSDLYTLSSS VTVPSSTWPS ETVTCNVAHP ASSTKVDKKI VPRDCGCKPC       240
ICTVPEVSSV FIFPPKPKDV LTITLTPKVT CVVVDISKDD PEVQFSWFVD DVEVHTAQTQ       300
PREEQFNSTF RSVSELPIMH QDWLNGKEFK CRVNSAAFPA PIEKTISKTK GRPKAPQVYT       360
IPPPKEQMAK DKVSLTCMIT DFFPEDITVE WQWNGQPAEN YKNTQPIMDT DGSYFVYSKL       420
NVQKSNWEAG NTFTCSVLHE GLHNHHTEKS LSHSPGK                                457

SEQ ID NO: 42           moltype = AA   length = 238
FEATURE                 Location/Qualifiers
REGION                  1..238
                        note = H2M280 Light Chain Protein
source                  1..238
                        mol_type = protein
                        organism = synthetic construct
SEQUENCE: 42
MMSPAQFLFL LVLWIRETNG DIVMTQTPLT LSVTIGQPAS ISCKSSQSLL HSDGKTYLNW        60
LLQRPGQSPK RLIYLVSKLD SGVPDRFTGS GSGTDFTLKI SRVEADDLGI YYCWQGTHFP       120
TFGGGTKLEI KRADAAPTVS IFPPSSEQLT SGGASVVCFL NNFYPKDINV KWKIDGSERQ       180
NGVLNSWTDQ DSKDSTYSMS STLTLTKDEY ERHNSYTCEA THKTSTSPIV KSFNRNEC         238

SEQ ID NO: 43           moltype = AA   length = 457
FEATURE                 Location/Qualifiers
REGION                  1..457
```

-continued

```
                        note = H2M281 Heavy Chain Protein
source                  1..457
                        mol_type = protein
                        organism = synthetic construct
SEQUENCE: 43
MNFGLRLIFL VLTLKGVQCD VKLVESGGGL VKPGGSLKLS CAASGFTFSS YSMSWVRQTP  60
EKRLEWVAII SSGGTYTYYT DSVKGRFTIS RDDAKNTLNL QMSSLKSEDT AMFYCTREAG 120
DYWGQGTTLT VSSAKTTPPS VYPLAPGSAA QTNSMVTLGC LVKGYFPEPV TVTWNSGSLS 180
SGVHTFPAVL QSDLYTLSSS VTVPSSTWPS ETVTCNVAHP ASSTKVDKKI VPRDCGCKPC 240
ICTVPEVSSV FIFPPKPKDV LTITLTPKVT CVVVDISKDD PEVQFSWFVD DVEVHTAQTQ 300
PREEQFNSTF RSVSELPIMH QDWLNGKEFK CRVNSAAFPA PIEKTISKTK GRPKAPQVYT 360
IPPPKEQMAK DKVSLTCMIT DFFPEDITVE WQWNGQPAEN YKNTQPIMDT DGSYFVYSKL 420
NVQKSNWEAG NTFTCSVLHE GLHNHHTEKS LSHSPGK                         457

SEQ ID NO: 44           moltype = AA  length = 238
FEATURE                 Location/Qualifiers
REGION                  1..238
                        note = H2M281 Light Chain Protein
source                  1..238
                        mol_type = protein
                        organism = synthetic construct
SEQUENCE: 44
MMSPAQFLFL LVLWIRETNG NVVMTQTPLT LSVTIGQPAS ISCKSSQSLL YSDGKTYLNW  60
LLQRPGQSPK RLIYLVSKLD SGVPDRFTGS GSGTDFTLKI SRVEAEDLGV YYCWQGTHFP 120
TFGGGTKLEI KRADAAPTVS IFPPSSEQLT SGGASVVCFL NNFYPKDINV KWKIDGSERQ 180
NGVLNSWTDQ DSKDSTYSMS STLTLTKDEY ERHNSYTCEA THKTSTSPIV KSFNRNEC   238

SEQ ID NO: 45           moltype = AA  length = 464
FEATURE                 Location/Qualifiers
REGION                  1..464
                        note = H2M282 Heavy Chain Protein
source                  1..464
                        mol_type = protein
                        organism = synthetic construct
SEQUENCE: 45
MERHWIFLLL LSVTAGVHSQ VQLQQSGAEL SRPGASVKMS CKAAGYTFSS YMIHWVKQRP  60
GQGLEWIGYI NPSSGYSNYN QKFKDKATLT ADKSSSTAYM QLSSLTSEDS AVYYCAFYDY 120
DGDWGQGTLV TVSAAKTTAP SVYPLAPVCG DTTGSSVTLG CLVKGYFPEP VTLTWNSGSL 180
SSGVHTFPAV LQSDLYTLSS SVTVTSSTWP SQSITCNVAH PASSTKVDKK IEPRGPTIKP 240
CPPCKCPAPN LLGGPSVFIF PPKIKDVLMI SLSPIVTCVV VDVSEDDPDV QISWFVNNVE 300
VHTAQTQTHR EDYNSTLRVV SALPIQHQDW MSGKEFKCKV NNKDLPAPIE RTISKPKGSV 360
RAPQVYVLPP PEEEMTKKQV TLTCMVTDFM PEDIYVEWTN NGKTELNYKN TEPVLDSDGS 420
YFMYSKLRVE KKNWVERNSY SCSVVHEGLH NHHTTKSFSR TPGK                 464

SEQ ID NO: 46           moltype = AA  length = 239
FEATURE                 Location/Qualifiers
REGION                  1..239
                        note = H2M282 Light Chain Protein
source                  1..239
                        mol_type = protein
                        organism = synthetic construct
SEQUENCE: 46
MMSPAQFLFL LVLWIRDTNG DVVMTQTPLT LSVTIGQPAS ISCKSSQSLF HSDGRTFLNW  60
LLQRPGQSPK RLIYKVSKLD SGVPDRFTGS GSGTDFTLKI SRVEAEDLGV YYCWQGTHFP 120
WTFGGGTKLE IKRADAAPTV SIFPPSSEQL TSGGASVVCF LNNFYPKDIN VKWKIDGSER 180
QNGVLNSWTD QDSKDSTYSM SSTLTLTKDE YERHNSYTCE ATHKTSTSPI VKSFNRNEC  239

SEQ ID NO: 47           moltype = AA  length = 459
FEATURE                 Location/Qualifiers
REGION                  1..459
                        note = H2M283 Heavy Chain Protein
source                  1..459
                        mol_type = protein
                        organism = synthetic construct
SEQUENCE: 47
MNLGLSIFL ALILKGVQCE VQLVESGGGL VQPGGSLKLS CAASGFTFSS YGMSWVRQTP   60
DKRLELVATI NSNGGSTFYP DSVKGRFTIS RDNAKNTLYL HMSSLKSEDT AIYYCVSPGS 120
WFPYWGRGTL VTVSAAKTTP PSVYPLAPGS AAQTNSMVTL GCLVKGYFPE PVTVTWNSGS 180
LSSGVHTFPA VLQSDLYTLS SSVTVPSSTW PSETVTCNVA HPASSTKVDK KIVPRDCGCK 240
PCICTVPEVS SVFIFPPKPK DVLTITLTPK VTCVVVDISK DDPEVQFSWF VDDVEVHTAQ 300
TQPREEQFNS TFRSVSELPI MHQDWLNGKE FKCRVNSAAF PAPIEKTISK TKGRPKAPQV 360
YTIPPPKEQM AKDKVSLTCM ITDFFPEDIT VEWQWNGQPA ENYKNTQPIM DTDGSYFVYS 420
KLNVQKSNWE AGNTFTCSVL HEGLHNHHTE KSLSHSPGK                       459

SEQ ID NO: 48           moltype = AA  length = 241
FEATURE                 Location/Qualifiers
REGION                  1..241
                        note = H2M283 Light Chain Protein
source                  1..241
```

```
                              mol_type = protein
                              organism = synthetic construct
SEQUENCE: 48
MMSPAQFLFL  LVLWIRVSET  NGDVVMTQTP  LTLSVTIGQP  ASISCKSSQS  LLDSDGKTYL    60
HWLLQRPGQS  PKRLIYLVSH  LDSGVPDRFT  GSGSGTDFTL  KISRVEAEDL  GVYYCWQGTH   120
FPQTFGGGTK  LEIKRADAAP  TVSIFPPSSE  QLTSGGASVV  CFLNNFYPKD  INVKWKIDGS   180
ERQNGVLNSW  TDQDSKDSTY  SMSSTLTLTK  DEYERHNSYT  CEATHKTSTS  PIVKSFNRNE   240
C                                                                        241

SEQ ID NO: 49             moltype = AA  length = 462
FEATURE                   Location/Qualifiers
REGION                    1..462
                          note = H2M284 Heavy Chain Protein
source                    1..462
                          mol_type = protein
                          organism = synthetic construct
SEQUENCE: 49
MGRLTSSFLL  LIVPAYVLSQ  VTLKESGPGI  LQPSQTLSLT  CSFSGFSLST  SGVGVGWIRQ    60
PSGKGLEWLA  HIWWDDDKNY  NPALKSRLTI  SKDTSTNQGF  LKIASVDTAD  TATYFCARIE   120
GQKGFAYWGQ  GTLVTVSAAK  TTPPSVYPLA  PGSAAQTNSM  VTLGCLVKGY  FPEPVTVTWN   180
SGSLSSGVHT  FPAVLQSDLY  TLSSSVTVPS  STWPSETVTC  NVAHPASSTK  VDKKIVPRDC   240
GCKPCICTVP  EVSSVFIFPP  KPKDVLTITL  TPKVTCVVVD  ISKDDPEVQF  SWFVDDVEVH   300
TAQTQPREEQ  FNSTFRSVSE  LPIMHQDWLN  GKEFKCRVNS  AAFPAPIEKT  ISKTKGRPKA   360
PQVYTIPPPK  EQMAKDKVSL  TCMITDFFPE  DITVEWQWNG  QPAENYKNTQ  PIMDTDGSYF   420
VYSKLNVQKS  NWEAGNTFTC  SVLHEGLHNH  HTEKSLSHSP  GK                       462

SEQ ID NO: 50             moltype = AA  length = 240
FEATURE                   Location/Qualifiers
REGION                    1..240
                          note = H2M284 Light Chain Protein
source                    1..240
                          mol_type = protein
                          organism = synthetic construct
SEQUENCE: 50
MDSQAQVLML  LLLWVSGTCG  DIVMSQSPSS  LAVSVGEKVT  MSCKSSQSLL  YSRNQKNYLA    60
WYQQKPGQSP  KLLIYWASTR  ESGVPDRFTG  SGSGTDFTLT  ISSVKAEDLA  VYYCQQYYSS   120
PYTFGGGTKL  EIKRADAAPT  VSIFPPSSEQ  LTSGGASVVC  FLNNFYPKDI  NVKWKIDGSE   180
RQNGVLNSWT  DQDSKDSTYS  MSSTLTLTKD  EYERHNSYTC  EATHKTSTSP  IVKSFNRNEC   240

SEQ ID NO: 51             moltype = AA  length = 463
FEATURE                   Location/Qualifiers
REGION                    1..463
                          note = H2M285 Heavy Chain Protein
source                    1..463
                          mol_type = protein
                          organism = synthetic construct
SEQUENCE: 51
MNLGLSFIFL  VLILKGVQCE  VQLVESGGGL  VQPGGSLKLS  CAASGFTFSN  YGIFWVRQTP    60
DKRLELVATV  KSNGGSTYYP  DSVKGRFTIS  RDNAKKTLYL  QMSSLKSEDT  AMYYCAREGG   120
DYWGQGTSVT  VSSATTTAPS  VYPLVPGCSD  TSGSSVTLGC  LVKGYFPEPV  TVKWNYGALS   180
SGVRTVL  QSGFYSLSSL  VTVPSSTWPS  QTVICNVAHP  ASKTELIKRI  EPRIPKPSTP   240
PGSSCPPGNI  LGGPSVFIFP  PKPKDALMIS  LTPKVTCVVV  DVSEDDPDVH  VSWFVDNKEV   300
HTAWTQPREA  QYNSTFRVVS  ALPIQHQDWM  RGKEFKCKVN  NKALPAPIER  TISKPKGRAQ   360
TPQVYTIPPP  REQMSKKKVS  LTCLVTNFFS  EAISVEWERN  GELEQDYKNT  PPILDSDGTY   420
FLYSKLTVDT  DSWLQGEIFT  CSVVHEALHN  HHTQKNLSRS  PGK                      463

SEQ ID NO: 52             moltype = AA  length = 238
FEATURE                   Location/Qualifiers
REGION                    1..238
                          note = H2M285 Light Chain Protein
source                    1..238
                          mol_type = protein
                          organism = synthetic construct
SEQUENCE: 52
MGIKMETHSQ  VFVYMLLWLS  GVEGDIVMTQ  SHKFMSTSVG  DRVSITCKAS  QDVGTAVAWY    60
QQKPGQSPKL  LIYWTSTRHT  GVPDRFTGSG  SGTDFTLTIR  NVQSEDLADY  FCQQYNRNPL   120
TFGAGTRLEL  KRADAAPTVS  IFPPSSEQLT  SGGASVVCFL  NNFYPKDINV  KWKIDGSERQ   180
NGVLNSWTDQ  DSKDSTYSMS  STLTLTKDEY  ERHNSYTCEA  THKTSTSPIV  KSFNRNEC     238

SEQ ID NO: 53             moltype = AA  length = 455
FEATURE                   Location/Qualifiers
REGION                    1..455
                          note = H2M286 Heavy Chain Protein
source                    1..455
                          mol_type = protein
                          organism = synthetic construct
SEQUENCE: 53
MRVLILLWLF  TAFPGILSDV  QLQESGPGLV  KPSQSLSLTC  TVTGYSITSD  YGWNWIRQFP    60
GNKLEWMGYI  RYSGITSYNP  SLKSRISITR  DTSKNQFFLQ  LNSVTTEDTA  TYYCTREVLS   120
```

```
WGQGTTLTVS SAKTTPPSVY PLAPGSAAQT NSMVTLGCLV KGYFPEPVTV TWNSGSLSSG    180
VHTFPAVLQS DLYTLSSSVT VPSSTWPSET VTCNVAHPAS STKVDKKIVP RDCGCKPCIC    240
TVPEVSSVFI FPPKPKDVLT ITLTPKVTCV VVDISKDDPE VQFSWFVDDV EVHTAQTQPR    300
EEQFNSTFRS VSELPIMHQD WLNGKEFKCR VNSAAFPAPI EKTISKTKGR PKAPQVYTIP    360
PPKEQMAKDK VSLTCMITDF FPEDITVEWQ WNGQPAENYK NTQPIMDTDG SYFVYSKLNV    420
QKSNWEAGNT FTCSVLHEGL HNHHTEKSLS HSPGK                              455

SEQ ID NO: 54           moltype = AA  length = 238
FEATURE                 Location/Qualifiers
REGION                  1..238
                        note = H2M286 Light Chain Protein
source                  1..238
                        mol_type = protein
                        organism = synthetic construct
SEQUENCE: 54
MKLPVRLLVL MFWIPASSSD VVMTQTPLSL PVSLGDQASI SCRSSQSLVH SNGNTYLHWF     60
LQKPGQSPKL LIYKVSNRFS GVPARFSGSG SGTDFTLKIS RVEAEDLGVY FCSQSTHVPP    120
TFGGGTKLEI KRADAAPTVS IFPPSSEQLT SGGASVVCFL NNFYPKDINV KWKIDGSERQ    180
NGVLNSWTDQ DSKDSTYSMS STLTLTKDEY ERHNSYTCEA THKTSTSPIV KSFNRNEC     238

SEQ ID NO: 55           moltype = AA  length = 457
FEATURE                 Location/Qualifiers
REGION                  1..457
                        note = H2M287 Heavy Chain Protein
source                  1..457
                        mol_type = protein
                        organism = synthetic construct
SEQUENCE: 55
MNFGLRLIFL VLTLKGVQCD VKLVESGGGL VKPGGSLKLS CAASGFTFSS YSMSWVRQTP     60
EKRLEWVAII SSGGSYIFYP DSVKGRFTIS RDNAKNTLYL QMSSLKSEDT AMYYCTREAG    120
DYWGQGTTLT VSSAKTTPPS VYPLAPGSAA QTNSMVTLGC LVKGYFPEPV TVTWNSGSLS    180
SGVHTFPAVL QSDLYTLSSS VTVPSSTWPS ETVTCNVAHP ASSTKVDKKI VPRDCGCKPC    240
ICTVPEVSSV FIFPPKPKDV LTITLTPKVT CVVVDISKDD PEVQFSWFVD DVEVHTAQTQ    300
PREEQFNSTF RSVSELPIMH QDWLNGKEFK CRVNSAAFPA PIEKTISKTK GRPKAPQVYT    360
IPPPKEQMAK DKVSLTCMIT DFFPEDITVE WQWNGQPAEN YKNTQPIMDT DGSYFVYSKL    420
NVQKSNWEAG NTFTCSVLHE GLHNHHTEKS LSHSPGK                            457

SEQ ID NO: 56           moltype = AA  length = 238
FEATURE                 Location/Qualifiers
REGION                  1..238
                        note = H2M287 Light Chain Protein
source                  1..238
                        mol_type = protein
                        organism = synthetic construct
SEQUENCE: 56
MMSPAQFLFL LVLWIRETNG DVVMTQTPLT LSVTIGQPAS ISCKSSQSLL HSDGKTYLNW     60
LLQRPGQSPK RLIYLVSKLD SGVPDRFTGS GSGTDFTLKI SRVEAEDLGV YYCWQGTHFP    120
TFGGGTKLEI KRADAAPTVS IFPPSSEQLT SGGASVVCFL NNFYPKDINV KWKIDGSERQ    180
NGVLNSWTDQ DSKDSTYSMS STLTLTKDEY ERHNSYTCEA THKTSTSPIV KSFNRNEC     238

SEQ ID NO: 57           moltype = AA  length = 457
FEATURE                 Location/Qualifiers
REGION                  1..457
                        note = H2M288 Heavy Chain Protein
source                  1..457
                        mol_type = protein
                        organism = synthetic construct
SEQUENCE: 57
MNFGLRLIFL VLTLKGVQCD VKLVESGGGL VKPGGSLKLS CAASGFTFSR YSLSWVRQTP     60
EKRLEWVAVI SSGGRYTFYP DGVKGRFTIS RDDAKNTLYL QMSSLRSEDT AMYFCTREAG    120
DYWGQGTPLT VSSAKTTPPS VYPLAPGSAA QTNSMVTLGC LVKGYFPEPV TVTWNSGSLS    180
SGVHTFPAVL QSDLYTLSSS VTVPSSTWPS ETVTCNVAHP ASSTKVDKKI VPRDCGCKPC    240
ICTVPEVSSV FIFPPKPKDV LTITLTPKVT CVVVDISKDD PEVQFSWFVD DVEVHTAQTQ    300
PREEQFNSTF RSVSELPIMH QDWLNGKEFK CRVNSAAFPA PIEKTISKTK GRPKAPQVYT    360
IPPPKEQMAK DKVSLTCMIT DFFPEDITVE WQWNGQPAEN YKNTQPIMDT DGSYFVYSKL    420
NVQKSNWEAG NTFTCSVLHE GLHNHHTEKS LSHSPGK                            457

SEQ ID NO: 58           moltype = AA  length = 238
FEATURE                 Location/Qualifiers
REGION                  1..238
                        note = H2M288 Light Chain Protein
source                  1..238
                        mol_type = protein
                        organism = synthetic construct
SEQUENCE: 58
MMSPAQFLFL LVLWIRETNG DVVMTQTPLT LSVTIGQPAS ISCKSSQSLL HSDGKTYLNW     60
LLQRPGQSPK RLIYLVSKLD SGVPDRFTGS GSGTDFTLKI SRVEAEDLGV YYCWQGTHFP    120
TFGGGTKLEI KRADAAPTVS IFPPSSEQLT SGGASVVCFL NNFYPKDINV KWKIDGSERQ    180
NGVLNSWTDQ DSKDSTYSMS STLTLTKDEY ERHNSYTCEA THKTSTSPIV KSFNRNEC     238
```

```
SEQ ID NO: 59            moltype = AA  length = 464
FEATURE                  Location/Qualifiers
REGION                   1..464
                         note = H2M289 Heavy Chain Protein
source                   1..464
                         mol_type = protein
                         organism = synthetic construct
SEQUENCE: 59
MGWSWIFLSL LSVTAGVFSE VQLQQSGPEL VKPGASVKIS CKASGYSFTG FFMNWVMQSH   60
GKSLEWIGRI NPYNGDTFYN QKFNDKATLT VDKSSRTAHM DLRNLASEDS AVYYCATISG  120
NYRGYAMDNW GQGTSVTVSS AKTTPPSVYP LAPGSAAQTN SMVTLGCLVK GYFPEPVTVT  180
WNSGSLSSGV HTFPAVLQSD LYTLSSSVTV PSSTWPSETV TCNVAHPASS TKVDKKIVPR  240
DCGCKPCICT VPEVSSVFIF PPKPKDVLTI TLTPKVTCVV VDISKDDPEV QFSWFVDDVE  300
VHTAQTQPRE EQFNSTFRSV SELPIMHQDW LNGKEFKCRV NSAAFPAPIE KTISKTKGRP  360
KAPQVYTIPP PKEQMAKDKV SLTCMITDFF PEDITVEWQW NGQPAENYKN TQPIMDTDGS  420
YFVYSKLNVQ KSNWEAGNTF TCSVLHEGLH NHHTEKSLSH SPGK                  464

SEQ ID NO: 60            moltype = AA  length = 238
FEATURE                  Location/Qualifiers
REGION                   1..238
                         note = H2M289 Light Chain Protein
source                   1..238
                         mol_type = protein
                         organism = synthetic construct
SEQUENCE: 60
MKLPVRLLVL MFWIPASSSD VLMTQTPLSL PVSLGDQASI SCRSSQTILH TNGNTYLEWY   60
LQKPGQSPKL LIYKVSNRFS GVPDRFSGSG SGTDFTLKIS RVEAEDLGVY YCFQGSRVPP  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 61            moltype = AA  length = 457
FEATURE                  Location/Qualifiers
REGION                   1..457
                         note = H2M290 Heavy Chain Protein
source                   1..457
                         mol_type = protein
                         organism = synthetic construct
SEQUENCE: 61
MNFGLRLIFL VLTLKGVQCD VKLVESGGGL VKPGGSLKLS CAASGFTFSS YSMSWVRQTP   60
EKRLEWVAII SSGGSYIFYP DSVKGRFTIS RDNAKNTLYL QMSSLKSEDT AMYYCTREAG  120
DYWGQGTTLT VSSAKTTPPS VYPLAPGSAA QTNSMVTLGC LVKGYFPEPV TVTWNSGSLS  180
SGVHTFPAVL QSDLYTLSSS VTVPSSTWPS ETVTCNVAHP ASSTKVDKKI VPRDCGCKPC  240
ICTVPEVSSV FIFPPKPKDV LTITLTPKVT CVVVDISKDD PEVQFSWFVD DVEVHTAQTQ  300
PREEQFNSTF RSVSELPIMH QDWLNGKEFK CRVNSAAFPA PIEKTISKTK GRPKAPQVYT  360
IPPPKEQMAK DKVSLTCMIT DFFPEDITVE WQWNGQPAEN YKNTQPIMDT DGSYFVYSKL  420
NVQKSNWEAG NTFTCSVLHE GLHNHHTEKS LSHSPGK                          457

SEQ ID NO: 62            moltype = AA  length = 238
FEATURE                  Location/Qualifiers
REGION                   1..238
                         note = H2M290 Light Chain Protein
source                   1..238
                         mol_type = protein
                         organism = synthetic construct
SEQUENCE: 62
MMSPAQFLFL LVLWIRETNG DVVMTQTPLT LSVTIGQPAS ISCKSSQSLL HSDGKTYLNW   60
LLQRPGQSPK RLLYLVSNLD SGVPDRFTGS GSGTDFTLKI SRVEAEDLGI YYCWQGTHFP  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 63            moltype = AA  length = 463
FEATURE                  Location/Qualifiers
REGION                   1..463
                         note = H2M291 Heavy Chain Protein
source                   1..463
                         mol_type = protein
                         organism = synthetic construct
SEQUENCE: 63
MGWSWIFLFL LSGTAGVHSE VQLQQSGPEL VKPGASMKIS CKASGYSFTG YTMNWVKQSH   60
GKNLEWIGLI NPYNGNTRYN QKFQDKATLT VDRSSSTAYM ELLSLTSEDS AVYYCVKEPS  120
DYWGQGTTLT VSSATTTAPS VYPLVPGCSD TSGSSVTLGC LVKGYFPEPV TVKWNYGALS  180
SGVRTVSSVL QSGFYSLSSL VTVPSSTWPS QTVICNVAHP ASKTELIKRI EPRIPKPSTP  240
PGSSCPPGNI LGGPSVFIFP PKPKDALMIS LTPKVTCVVV DVSEDDPDVH VSWFVDNKEV  300
HTAWTQPREA QYNSTFRVVS ALPIQHQDWM RGKEFKCKVN NKALPAPIER TISKPKGRAQ  360
TPQVYTIPPP REQMSKKKVS LTCLVTNFFS EAISVEWERN GELEQDYKNT PPILDSDGTY  420
FLYSKLTVDT DSWLQGEIFT CSVVHEALHN HHTQKNLSRS PGK                   463

SEQ ID NO: 64            moltype = AA  length = 238
```

```
FEATURE                 Location/Qualifiers
REGION                  1..238
                        note = H2M291 Light Chain Protein
source                  1..238
                        mol_type = protein
                        organism = synthetic construct
SEQUENCE: 64
MKLPVRLLVL MFWIPASSSD VVMTQTPLSL PVSLGDQASI SCRSSQSLVH INGNTYLHWY   60
LQKPGQSPKL LIYKVSKRFS GVPDRFSGSG SGTDFTLKIS RVEAADLGVY FCSQSTHVPP  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 65           moltype = AA  length = 463
FEATURE                 Location/Qualifiers
REGION                  1..463
                        note = H2M292 Heavy Chain Protein
source                  1..463
                        mol_type = protein
                        organism = synthetic construct
SEQUENCE: 65
MGWSWIFLFL LSGTAGVHSE VQLQQSGPEL VKPGASRKIS CKASGYSFTG YTMNWVKKSH   60
GKNLEWIGLI NPSNGGTRYN QKFKDKATLT VDKSSSTAYM ELLSLTSEDS AVYYCVKEPS  120
DYWGQGTTLT VSSATTTAPS VYPLVPGCSD TSGSSVTLGC LVKGYFPEPV TVKWNYGALS  180
SGVRTVSSVL QSGFYSLSSL VTVPSSTWPS QTVICNVAHP ASKTELIKRI EPRIPKPSTP  240
PGSSCPPGNI LGGPSVFIFP PKPKDALMIS LTPKVTCVVV DVSEDDPDVH VSWFVDNKEV  300
HTAWTQPREA QYNSTFRVVS ALPIQHQDWM RGKEFKCKVN NKALPAPIER TISKPKGRAQ  360
TPQVYTIPPP REQMSKKKVS LTCLVTNFFS EAISVEWERN GELEQDYKNT PPILDSDGTY  420
FLYSKLTVDT DSWLQGEIFT CSVVHEALHN HHTQKNLSRS PGK                    463

SEQ ID NO: 66           moltype = AA  length = 238
FEATURE                 Location/Qualifiers
REGION                  1..238
                        note = H2M292 Light Chain Protein
source                  1..238
                        mol_type = protein
                        organism = synthetic construct
SEQUENCE: 66
MKLPVRLLVL MFWIPASSSD VVMTQTPLSL PVSLGDQASI SCRSSQSLVH SNGNTYLHWY   60
LQKPGQSPKL LIYKVSNRFS GVPDRFSGRG SGTDFTLKIS RVEAEDLGIY FCSQSTHVPP  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 67           moltype = AA  length = 463
FEATURE                 Location/Qualifiers
REGION                  1..463
                        note = H2M293 Heavy Chain Protein
source                  1..463
                        mol_type = protein
                        organism = synthetic construct
SEQUENCE: 67
MNLGLSFIFL ALILKGVQCE VQLVESGGGL VQPGGSLKLS CAASGFTFSN YGIFWVRQTP   60
DKRLELVATV KSNGGSTYYP DSVKGRFTIS RDNAKKTLYL QMSSLKSEDT AMYYCAREGG  120
DYWGQGTSVT VSSATTTAPS VYPLVPGCSD TSGSSVTLGC LVKGYFPEPV TVKWNYGALS  180
SGVRTVSSVL QSGFYSLSSL VTVPSSTWPS QTVICNVAHP ASKTELIKRI EPRIPKPSTP  240
PGSSCPPGNI LGGPSVFIFP PKPKDALMIS LTPKVTCVVV DVSEDDPDVH VSWFVDNKEV  300
HTAWTQPREA QYNSTFRVVS ALPIQHQDWM RGKEFKCKVN NKALPAPIER TISKPKGRAQ  360
TPQVYTIPPP REQMSKKKVS LTCLVTNFFS EAISVEWERN GELEQDYKNT PPILDSDGTY  420
FLYSKLTVDT DSWLQGEIFT CSVVHEALHN HHTQKNLSRS PGK                    463

SEQ ID NO: 68           moltype = AA  length = 238
FEATURE                 Location/Qualifiers
REGION                  1..238
                        note = H2M293 Light Chain Protein
source                  1..238
                        mol_type = protein
                        organism = synthetic construct
SEQUENCE: 68
MGIKMETHSQ VFVYMLLWLS GVEGDIVMTQ SHKFMSTSVG DRVSITCKAS QDVGTAVAWY   60
QQKPGQSPKL LIYWTSTRHI GVPDRFTGSG SGTDFTLTIR NVQSEDLANY FCQQYSKNPL  120
TFGAGTKLEL KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 69           moltype = AA  length = 468
FEATURE                 Location/Qualifiers
REGION                  1..468
                        note = H2M294 Heavy Chain Protein
source                  1..468
                        mol_type = protein
                        organism = synthetic construct
```

```
SEQUENCE: 69
MSTEHRPLSV NLGLSFIFLA LILKGVQCEV QLVESGGGLV QPGGSLKLSC AASGFTFSSY      60
GMSWVRQTPD KRLELVATIN SNGGGTYYPD SVKGRFTISR DNAKNTLYLQ MSSLKSEDTA     120
IYYCASPGSW FPYWGQGTLV TVSAAKTTPP SVYPLAPGSA AQTNSMVTLG CLVKGYFPEP     180
VTVTWNSGSL SSGVHTFPAV LQSDLYTLSS SVTVPSSTWP SETVTCNVAH PASSTKVDKK     240
IVPRDCGCKP CICTVPEVSS VFIFPPKPKD VLTITLTPKV TCVVVDISKD DPEVQFSWFV     300
DDDVEVHTAQT QPREEQFNST FRSVSELPIM HQDWLNGKEF KCRVNSAAFP APIEKTISKT    360
KGRPKAPQVY TIPPPKEQMA KDKVSLTCMI TDFFPEDITV EWQWNGQPAE NYKNTQPIMD     420
TDGSYFVYSK LNVQKSNWEA GNTFTCSVLH EGLHNHHTEK SLSHSPGK                  468

SEQ ID NO: 70           moltype = AA  length = 239
FEATURE                 Location/Qualifiers
REGION                  1..239
                        note = H2M294 Light Chain Protein
source                  1..239
                        mol_type = protein
                        organism = synthetic construct
SEQUENCE: 70
MMSPAQFLFL LVLWIRETNG DVVMTQTPLT LSVTIGQPAS ISCKSSQSLL DSDGKTYLHW      60
LLQRPGQSPR RLIFLVSKLD SGVPDRFTGS GSGTDFTLKI SRVEAEDLGV YYCWQGTHFP     120
QTFGGGTKLE IKRADAAPTV SIFPPSSEQL TSGGASVVCF LNNFYPKDIN VKWKIDGSER     180
QNGVLNSWTD QDSKDSTYSM SSTLTLTKDE YERHNSYTCE ATHKTSTSPI VKSFNRNEC      239

SEQ ID NO: 71           moltype = AA  length = 457
FEATURE                 Location/Qualifiers
REGION                  1..457
                        note = H2M295 Heavy Chain Protein
source                  1..457
                        mol_type = protein
                        organism = synthetic construct
SEQUENCE: 71
MGWSWIFLFL LSGTAGVHSE VQLQQSGPEL VKPGASRKIS CKASGYSFTG YTMNWVKKSH      60
GKNLEWIGLI NPYNGGTRYN QKFKGKATLT VDKSSSTAYM ELLSLTSEDS AVYYCVKEPS     120
DYWGQGTTLT VSSAKTTPPS VYPLAPGSAA QTNSMVTLGC LVKGYFPEPV TVTWNSGSLS     180
SGVHTFPAVL QSDLYTLSSS VTVPSSTWPS ETVTCNVAHP ASSTKVDKKI VPRDCGCKPC     240
ICTVPEVSSV FIFPPKPKDV LTITLTPKVT CVVVDISKDD PEVQFSWFVD DVEVHTAQTQ     300
PREEQFNSTF RSVSELPIMH QDWLNGKEFK CRVNSAAFPA PIEKTISKTK GRPKAPQVYT     360
IPPPKEQMAK DKVSLTCMIT DFFPEDITVE WQWNGQPAEN YKNTQPIMDT DGSYFVYSKL     420
NVQKSNWEAG NTFTCSVLHE GLHNHHTEKS LSHSPGK                              457

SEQ ID NO: 72           moltype = AA  length = 238
FEATURE                 Location/Qualifiers
REGION                  1..238
                        note = H2M295 Light Chain Protein
source                  1..238
                        mol_type = protein
                        organism = synthetic construct
SEQUENCE: 72
MKLPVRLLVL MFWIPASSSD VVMTQTPLSL PVSLGDQASI SCRSSQSLVH SNGNTYLHWY      60
LQKPGQSPKL LIYKVSKRFS GVPDRFSGCG SGTDFTLKIS RLEAEDLGVY FCSQSSHVPP     120
TFGGGTKLEI KRADAAPTVS IFPPSSEQLT SGGASVVCFL NNFYPKDINV KWKIDGSERQ     180
NGVLNSWTDQ DSKDSTYSMS STLTLTKDEY ERHNSYTCEA THKTSTSPIV KSFNRNEC       238

SEQ ID NO: 73           moltype = AA  length = 462
FEATURE                 Location/Qualifiers
REGION                  1..462
                        note = H2M296 Heavy Chain Protein
source                  1..462
                        mol_type = protein
                        organism = synthetic construct
SEQUENCE: 73
MGRLTSSFLL LIVPAYVLSQ VTLKESGPGI LQPSQTLSLT CSFSGFSLST SGMGVGWIRQ      60
PSGKGLEWLA HIWWDDDKRY NPALKSRLTI SKDTSSNQVF LKIANVDTSD TATYYCSRIE     120
GQRGFAYWGQ GTLVTVSAAK TTPPSVYPLA PGSAAQTNSM VTLGCLVKGY FPEPVTVTWN     180
SGSLSSGVHT FPAVLQSDLY TLSSSVTVPS STWPSETVTC NVAHPASSTK VDKKIVPRDC     240
GCKPCICTVP EVSSVFIFPP KPKDVLTITL TPKVTCVVVD ISKDDPEVQF SWFVDDVEVH     300
TAQTQPREEQ FNSTFRSVSE LPIMHQDWLN GKEFKCRVNS AAFPAPIEKT ISKTKGRPKA     360
PQVYTIPPPK EQMAKDKVSL TCMITDFFPE DITVEWQWNG QPAENYKNTQ PIMDTDGSYF     420
VYSKLNVQKS NWEAGNTFTC SVLHEGLHNH HTEKSLSHSP GK                        462

SEQ ID NO: 74           moltype = AA  length = 240
FEATURE                 Location/Qualifiers
REGION                  1..240
                        note = H2M296 Light Chain Protein
source                  1..240
                        mol_type = protein
                        organism = synthetic construct
SEQUENCE: 74
MDSQAQVLML LLLWVSGTCG DIVMSQSPSS LAVSVGEMIT MTCKSSQSLL YSRNQKNYLA      60
```

```
WYQQKPGQSP KLLIYWASTR ESGVPDRFTG SGSGTDFTLT ISSVKAEDLA VYYCQQYYSQ     120
PYTFGGGTKL EIKRADAAPT VSIFPPSSEQ LTSGGASVVC FLNNFYPKDI NVKWKIDGSE     180
RQNGVLNSWT DQDSKDSTYS MSSTLTLTKD EYERHNSYTC EATHKTSTSP IVKSFNRNEC     240

SEQ ID NO: 75           moltype = AA  length = 463
FEATURE                 Location/Qualifiers
REGION                  1..463
                        note = H2M297 Heavy Chain Protein
source                  1..463
                        mol_type = protein
                        organism = synthetic construct
SEQUENCE: 75
MNLGLSFIFL ALILKGVQCE VQLVESGGGL VQPGGSLKLS CAASGFSFSS YGIFWVRQTP      60
DKRLELVATI KSNGGRTYYP DSVKGRFTIS RDNAKNTLHL QMSSLKSEDT AMYYCAREGG     120
DYWGQGTSVT VSSATTTAPS VYPLVPGCSD TSGSSVTLGC LVKGYFPEPV TVKWNYGALS     180
SGVRTVSSVL QSGFYSLSSL VTVPSSTWPS QTVICNVAHP ASKTELIKRI EPRIPKPSTP     240
PGSSCPPGNI LGGPSVFIFP PKPKDALMIS LTPKVTCVVV DVSEDDPDVH VSWFVDNKEV     300
HTAWTQPREA QYNSTFRVVS ALPIQHQDWM RGKEFKCKVN NKALPAPIER TISKPKGRAQ     360
TPQVYTIPPP REQMSKKKVS LTCLVTNFFS EAISVEWERN GELEQDYKNT PPILDSDGTY     420
FLYSKLTVDT DSWLQGEIFT CSVVHEALHN HHTQKNLSRS PGK                      463

SEQ ID NO: 76           moltype = AA  length = 238
FEATURE                 Location/Qualifiers
REGION                  1..238
                        note = H2M297 Light Chain Protein
source                  1..238
                        mol_type = protein
                        organism = synthetic construct
SEQUENCE: 76
MKLPVRLLVL MFWIPASSSD VLMTQTPLSL PVSLGDQASI SCRSSQSVVH SNGNTYLEWY      60
LQKPGQSPKL LIYKVSNRFS GVPDRFSGSG SGTDFTLKIS RVEAEDLGIY YCFQGSRVPP     120
TFGGGTKLEI KRADAAPTVS IFPPSSEQLT SGGASVVCFL NNFYPKDINV KWKIDGSERQ     180
NGVLNSWTDQ DSKDSTYSMS STLTLTKDEY ERHNNYTCEA THKTSTSPIV KSFNRNEC      238

SEQ ID NO: 77           moltype = AA  length = 457
FEATURE                 Location/Qualifiers
REGION                  1..457
                        note = H2M298 Heavy Chain Protein
source                  1..457
                        mol_type = protein
                        organism = synthetic construct
SEQUENCE: 77
MNFGLRLIFL VLTLKGVQCD VKLVESGGGL VKPGGSLKLS CAASGFTFSR YSMSWVRQTP      60
EKKLEWVAII STGGSYMFYP DSAKGRFTIS RDDAKNTLYL QMSSLKSEDT AMYYCTREAG     120
DYWGQGTTLT VSSAKTTPPS VYPLAPGSAA QTNSMVTLGC LVKGYFPEPV TVTWNSGSLS     180
SGVHTFPAVL QSDLYTLSSS VTVPSSTWPS ETVTCNVAHP ASSTKVDKKI VPRDCGCKPC     240
ICTVPEVSSV FIFPPKPKDV LTITLTPKVT CVVVDISKDD PEVQFSWFVD DVEVHTAQTQ     300
PREEQFNSTF RSVSELPIMH QDWLNGKEFK CRVNSAAFPA PIEKTISKTK GRPKAPQVYT     360
IPPPKEQMAK DKVSLTCMIT DFFPEDITVE WQWNGQPAEN YKNTQPIMDT DGSYFVYSKL     420
NVQKSNWEAG NTFTCSVLHE GLHNHHTEKS LSHSPGK                             457

SEQ ID NO: 78           moltype = AA  length = 238
FEATURE                 Location/Qualifiers
REGION                  1..238
                        note = H2M298 Light Chain Protein
source                  1..238
                        mol_type = protein
                        organism = synthetic construct
SEQUENCE: 78
MMSPAQFLFL LVLWIRETNG DVVMTQTPLT LSVTIGQPAS ISCKSSQSLL HSDGKTYLNW      60
LLQRPGQSPR RLIYLVSKLD SGVPDRFTGS GSGTDFTLKI SRVESEDLGV YYCWQGTHFP     120
TFGGGTKLEI KRADAAPTVS IFPPSSEQLT SGGASVVCFL NNFYPKDINV KWKIDGSERQ     180
NGVLNSWTDQ DSKDSTYSMS STLTLTKDEY ERHNSYTCEA THKTSTSPIV KSFNRNEC      238

SEQ ID NO: 79           moltype = AA  length = 457
FEATURE                 Location/Qualifiers
REGION                  1..457
                        note = H2M299 Heavy Chain Protein
source                  1..457
                        mol_type = protein
                        organism = synthetic construct
SEQUENCE: 79
MNLGLSFIFL ALILKGVQCE VQLVESGGGL VQPGGSLKLS CAASGFTFNI YGIFWVRQTP      60
DKRLELVATI HSNGGRIYYP DSVKGRFTIS RDNAKNTLYL QMSSLKSEDT AMYYCAREGG     120
DYWGQGTSVT VSSAKTTPPS VYPLAPGSAA QTNSMVTLGC LVKGYFPEPV TVTWNSGSLS     180
SGVHTFPAVL QSDLYTLSSS VTVPSSTWPS ETVTCNVAHP ASSTKVDKKI VPRDCGCKPC     240
ICTVPEVSSV FIFPPKPKDV LTITLTPKVT CVVVDISKDD PEVQFSWFVD DVEVHTAQTQ     300
PREEQFNSTF RSVSELPIMH QDWLNGKEFK CRVNSAAFPA PIEKTISKTK GRPKAPQVYT     360
IPPPKEQMAK DKVSLTCMIT DFFPEDITVE WQWNGQPAEN YKNTQPIMDT DGSYFVYSKL     420
```

```
NVQKSNWEAG NTFTCSVLHE GLHNHHTEKS LSHSPGK                              457

SEQ ID NO: 80          moltype = AA  length = 238
FEATURE                Location/Qualifiers
REGION                 1..238
                       note = H2M299 Light Chain Protein
source                 1..238
                       mol_type = protein
                       organism = synthetic construct
SEQUENCE: 80
MGIKMETHSQ VFVYMLLWLS GVEGDIVMTQ SHKVMATSVG DRVSITCKAS QDVGTAVAWY      60
QQKPGQSPKL LIYWASTRHT GVPDRFTGSG SGTDFTLTIN NVLSEDLVDY FCQQYRRYPL     120
TFGAGTKLEL KRADAAPTVS IFPPSSEQLT SGGASVVCFL NNFYPKDINV KWKIDGSERQ     180
NGVLNSWTDQ DSKDSTYSMS STLTLTKDEY ERHNSYTCEA THKTSTSPIV KSFNRNEC       238

SEQ ID NO: 81          moltype = AA  length = 5
FEATURE                Location/Qualifiers
REGION                 1..5
                       note = H2M279H-CDR1
source                 1..5
                       mol_type = protein
                       organism = synthetic construct
SEQUENCE: 81
SYGIF                                                                   5

SEQ ID NO: 82          moltype = AA  length = 17
FEATURE                Location/Qualifiers
REGION                 1..17
                       note = H2M279H-CDR2
source                 1..17
                       mol_type = protein
                       organism = synthetic construct
SEQUENCE: 82
TIKSNGGRTY YPDSVKG                                                     17

SEQ ID NO: 83          moltype = AA  length = 5
FEATURE                Location/Qualifiers
REGION                 1..5
                       note = H2M279H-CDR3
source                 1..5
                       mol_type = protein
                       organism = synthetic construct
SEQUENCE: 83
EGGDY                                                                   5

SEQ ID NO: 84          moltype = AA  length = 11
FEATURE                Location/Qualifiers
REGION                 1..11
                       note = H2M279L-CDR1
source                 1..11
                       mol_type = protein
                       organism = synthetic construct
SEQUENCE: 84
KASQDVGTAV A                                                           11

SEQ ID NO: 85          moltype = AA  length = 7
FEATURE                Location/Qualifiers
REGION                 1..7
                       note = H2M279L-CDR2
source                 1..7
                       mol_type = protein
                       organism = synthetic construct
SEQUENCE: 85
WASTRHT                                                                 7

SEQ ID NO: 86          moltype = AA  length = 9
FEATURE                Location/Qualifiers
REGION                 1..9
                       note = H2M279L-CDR3
source                 1..9
                       mol_type = protein
                       organism = synthetic construct
SEQUENCE: 86
QQYKSNPLT                                                               9

SEQ ID NO: 87          moltype = AA  length = 5
FEATURE                Location/Qualifiers
REGION                 1..5
                       note = H2M280H-CDR1
```

```
source                  1..5
                        mol_type = protein
                        organism = synthetic construct
SEQUENCE: 87
SYSMS                                                                    5

SEQ ID NO: 88           moltype = AA  length = 17
FEATURE                 Location/Qualifiers
REGION                  1..17
                        note = H2M280H-CDR2
source                  1..17
                        mol_type = protein
                        organism = synthetic construct
SEQUENCE: 88
IISSGGSYTF YPDSVKG                                                      17

SEQ ID NO: 89           moltype = AA  length = 5
FEATURE                 Location/Qualifiers
REGION                  1..5
                        note = H2M280H-CDR3
source                  1..5
                        mol_type = protein
                        organism = synthetic construct
SEQUENCE: 89
EAGDY                                                                    5

SEQ ID NO: 90           moltype = AA  length = 16
FEATURE                 Location/Qualifiers
REGION                  1..16
                        note = H2M280L-CDR1
source                  1..16
                        mol_type = protein
                        organism = synthetic construct
SEQUENCE: 90
KSSQSLLHSD GKTYLN                                                       16

SEQ ID NO: 91           moltype = AA  length = 7
FEATURE                 Location/Qualifiers
REGION                  1..7
                        note = H2M280L-CDR2
source                  1..7
                        mol_type = protein
                        organism = synthetic construct
SEQUENCE: 91
LVSKLDS                                                                  7

SEQ ID NO: 92           moltype = AA  length = 8
FEATURE                 Location/Qualifiers
REGION                  1..8
                        note = H2M280L-CDR3
source                  1..8
                        mol_type = protein
                        organism = synthetic construct
SEQUENCE: 92
WQGTHFPT                                                                 8

SEQ ID NO: 93           moltype = AA  length = 5
FEATURE                 Location/Qualifiers
REGION                  1..5
                        note = H2M281H-CDR1
source                  1..5
                        mol_type = protein
                        organism = synthetic construct
SEQUENCE: 93
SYSMS                                                                    5

SEQ ID NO: 94           moltype = AA  length = 17
FEATURE                 Location/Qualifiers
REGION                  1..17
                        note = H2M281H-CDR2
source                  1..17
                        mol_type = protein
                        organism = synthetic construct
SEQUENCE: 94
IISSGGTYTY YTDSVKG                                                      17

SEQ ID NO: 95           moltype = AA  length = 5
FEATURE                 Location/Qualifiers
REGION                  1..5
```

```
                         note = H2M281H-CDR3
source                   1..5
                         mol_type = protein
                         organism = synthetic construct
SEQUENCE: 95
EAGDY                                                                    5

SEQ ID NO: 96            moltype = AA  length = 16
FEATURE                  Location/Qualifiers
REGION                   1..16
                         note = H2M281L-CDR1
source                   1..16
                         mol_type = protein
                         organism = synthetic construct
SEQUENCE: 96
KSSQSLLYSD GKTYLN                                                       16

SEQ ID NO: 97            moltype = AA  length = 7
FEATURE                  Location/Qualifiers
REGION                   1..7
                         note = H2M281L-CDR2
source                   1..7
                         mol_type = protein
                         organism = synthetic construct
SEQUENCE: 97
LVSKLDS                                                                  7

SEQ ID NO: 98            moltype = AA  length = 8
FEATURE                  Location/Qualifiers
REGION                   1..8
                         note = H2M281L-CDR3
source                   1..8
                         mol_type = protein
                         organism = synthetic construct
SEQUENCE: 98
WQGTHFPT                                                                 8

SEQ ID NO: 99            moltype = AA  length = 5
FEATURE                  Location/Qualifiers
REGION                   1..5
                         note = H2M282H-CDR1
source                   1..5
                         mol_type = protein
                         organism = synthetic construct
SEQUENCE: 99
SYMIH                                                                    5

SEQ ID NO: 100           moltype = AA  length = 17
FEATURE                  Location/Qualifiers
REGION                   1..17
                         note = H2M282H-CDR2
source                   1..17
                         mol_type = protein
                         organism = synthetic construct
SEQUENCE: 100
YINPSSGYSN YNQKFKD                                                      17

SEQ ID NO: 101           moltype = AA  length = 6
FEATURE                  Location/Qualifiers
REGION                   1..6
                         note = H2M282H-CDR3
source                   1..6
                         mol_type = protein
                         organism = synthetic construct
SEQUENCE: 101
YDYDGD                                                                   6

SEQ ID NO: 102           moltype = AA  length = 16
FEATURE                  Location/Qualifiers
REGION                   1..16
                         note = H2M282L-CDR1
source                   1..16
                         mol_type = protein
                         organism = synthetic construct
SEQUENCE: 102
KSSQSLFHSD GRTFLN                                                       16

SEQ ID NO: 103           moltype = AA  length = 7
FEATURE                  Location/Qualifiers
```

```
REGION                    1..7
                          note = H2M282L-CDR2
source                    1..7
                          mol_type = protein
                          organism = synthetic construct
SEQUENCE: 103
KVSKLDS                                                                   7

SEQ ID NO: 104            moltype = AA  length = 9
FEATURE                   Location/Qualifiers
REGION                    1..9
                          note = H2M282L-CDR3
source                    1..9
                          mol_type = protein
                          organism = synthetic construct
SEQUENCE: 104
WQGTHFPWT                                                                 9

SEQ ID NO: 105            moltype = AA  length = 5
FEATURE                   Location/Qualifiers
REGION                    1..5
                          note = H2M283H-CDR1
source                    1..5
                          mol_type = protein
                          organism = synthetic construct
SEQUENCE: 105
SYGMS                                                                     5

SEQ ID NO: 106            moltype = AA  length = 17
FEATURE                   Location/Qualifiers
REGION                    1..17
                          note = H2M283H-CDR2
source                    1..17
                          mol_type = protein
                          organism = synthetic construct
SEQUENCE: 106
TINSNGGSTF YPDSVKG                                                        17

SEQ ID NO: 107            moltype = AA  length = 7
FEATURE                   Location/Qualifiers
REGION                    1..7
                          note = H2M283H-CDR3
source                    1..7
                          mol_type = protein
                          organism = synthetic construct
SEQUENCE: 107
PGSWFPY                                                                   7

SEQ ID NO: 108            moltype = AA  length = 16
FEATURE                   Location/Qualifiers
REGION                    1..16
                          note = H2M283L-CDR1
source                    1..16
                          mol_type = protein
                          organism = synthetic construct
SEQUENCE: 108
KSSQSLLDSD GKTYLH                                                         16

SEQ ID NO: 109            moltype = AA  length = 7
FEATURE                   Location/Qualifiers
REGION                    1..7
                          note = H2M283L-CDR2
source                    1..7
                          mol_type = protein
                          organism = synthetic construct
SEQUENCE: 109
LVSHLDS                                                                   7

SEQ ID NO: 110            moltype = AA  length = 9
FEATURE                   Location/Qualifiers
REGION                    1..9
                          note = H2M283L-CDR3
source                    1..9
                          mol_type = protein
                          organism = synthetic construct
SEQUENCE: 110
WQGTHFPQT                                                                 9

SEQ ID NO: 111            moltype = AA  length = 7
```

```
FEATURE                 Location/Qualifiers
REGION                  1..7
                        note = H2M284H-CDR1
source                  1..7
                        mol_type = protein
                        organism = synthetic construct
SEQUENCE: 111
TSGVGVG                                                                        7

SEQ ID NO: 112          moltype = AA  length = 16
FEATURE                 Location/Qualifiers
REGION                  1..16
                        note = H2M284H-CDR2
source                  1..16
                        mol_type = protein
                        organism = synthetic construct
SEQUENCE: 112
HIWWDDDKNY NPALKS                                                             16

SEQ ID NO: 113          moltype = AA  length = 9
FEATURE                 Location/Qualifiers
REGION                  1..9
                        note = H2M284H-CDR3
source                  1..9
                        mol_type = protein
                        organism = synthetic construct
SEQUENCE: 113
IEGQKGFAY                                                                      9

SEQ ID NO: 114          moltype = AA  length = 17
FEATURE                 Location/Qualifiers
REGION                  1..17
                        note = H2M284L-CDR1
source                  1..17
                        mol_type = protein
                        organism = synthetic construct
SEQUENCE: 114
KSSQSLLYSR NQKNYLA                                                            17

SEQ ID NO: 115          moltype = AA  length = 7
FEATURE                 Location/Qualifiers
REGION                  1..7
                        note = H2M284L-CDR2
source                  1..7
                        mol_type = protein
                        organism = synthetic construct
SEQUENCE: 115
WASTRES                                                                        7

SEQ ID NO: 116          moltype = AA  length = 9
FEATURE                 Location/Qualifiers
REGION                  1..9
                        note = H2M284L-CDR3
source                  1..9
                        mol_type = protein
                        organism = synthetic construct
SEQUENCE: 116
QQYYSSPYT                                                                      9

SEQ ID NO: 117          moltype = AA  length = 5
FEATURE                 Location/Qualifiers
REGION                  1..5
                        note = H2M285H-CDR1
source                  1..5
                        mol_type = protein
                        organism = synthetic construct
SEQUENCE: 117
NYGIF                                                                          5

SEQ ID NO: 118          moltype = AA  length = 17
FEATURE                 Location/Qualifiers
REGION                  1..17
                        note = H2M285H-CDR2
source                  1..17
                        mol_type = protein
                        organism = synthetic construct
SEQUENCE: 118
TVKSNGGSTY YPDSVKG                                                            17
```

-continued

| | | |
|---|---|---|
| SEQ ID NO: 119<br>FEATURE<br>REGION<br><br>source | moltype = AA length = 5<br>Location/Qualifiers<br>1..5<br>note = H2M285H-CDR3<br>1..5<br>mol_type = protein<br>organism = synthetic construct | |
| SEQUENCE: 119<br>EGGDY | | 5 |
| SEQ ID NO: 120<br>FEATURE<br>REGION<br><br>source | moltype = AA length = 11<br>Location/Qualifiers<br>1..11<br>note = H2M285L-CDR1<br>1..11<br>mol_type = protein<br>organism = synthetic construct | |
| SEQUENCE: 120<br>KASQDVGTAV A | | 11 |
| SEQ ID NO: 121<br>FEATURE<br>REGION<br><br>source | moltype = AA length = 7<br>Location/Qualifiers<br>1..7<br>note = H2M285L-CDR2<br>1..7<br>mol_type = protein<br>organism = synthetic construct | |
| SEQUENCE: 121<br>WTSTRHT | | 7 |
| SEQ ID NO: 122<br>FEATURE<br>REGION<br><br>source | moltype = AA length = 9<br>Location/Qualifiers<br>1..9<br>note = H2M285L-CDR3<br>1..9<br>mol_type = protein<br>organism = synthetic construct | |
| SEQUENCE: 122<br>QQYNRNPLT | | 9 |
| SEQ ID NO: 123<br>SEQUENCE: 123<br>000 | moltype = length = | |
| SEQ ID NO: 124<br>SEQUENCE: 124<br>000 | moltype = length = | |
| SEQ ID NO: 125<br>SEQUENCE: 125<br>000 | moltype = length = | |
| SEQ ID NO: 126<br>FEATURE<br>REGION<br><br>source | moltype = AA length = 16<br>Location/Qualifiers<br>1..16<br>note = H2M286L-CDR1<br>1..16<br>mol_type = protein<br>organism = synthetic construct | |
| SEQUENCE: 126<br>RSSQSLVHSN GNTYLH | | 16 |
| SEQ ID NO: 127<br>FEATURE<br>REGION<br><br>source | moltype = AA length = 7<br>Location/Qualifiers<br>1..7<br>note = H2M286L-CDR2<br>1..7<br>mol_type = protein<br>organism = synthetic construct | |
| SEQUENCE: 127<br>KVSNRFS | | 7 |
| SEQ ID NO: 128<br>FEATURE<br>REGION<br><br>source | moltype = AA length = 9<br>Location/Qualifiers<br>1..9<br>note = H2M286L-CDR3<br>1..9<br>mol_type = protein<br>organism = synthetic construct | |

-continued

```
SEQUENCE: 128
SQSTHVPPT                                                                9

SEQ ID NO: 129          moltype = AA  length = 5
FEATURE                 Location/Qualifiers
REGION                  1..5
                        note = H2M287H-CDR1
source                  1..5
                        mol_type = protein
                        organism = synthetic construct
SEQUENCE: 129
SYSMS                                                                    5

SEQ ID NO: 130          moltype = AA  length = 17
FEATURE                 Location/Qualifiers
REGION                  1..17
                        note = H2M287H-CDR2
source                  1..17
                        mol_type = protein
                        organism = synthetic construct
SEQUENCE: 130
IISSGGSYIF YPDSVKG                                                      17

SEQ ID NO: 131          moltype = AA  length = 5
FEATURE                 Location/Qualifiers
REGION                  1..5
                        note = H2M287H-CDR3
source                  1..5
                        mol_type = protein
                        organism = synthetic construct
SEQUENCE: 131
EAGDY                                                                    5

SEQ ID NO: 132          moltype = AA  length = 16
FEATURE                 Location/Qualifiers
REGION                  1..16
                        note = H2M287L-CDR1
source                  1..16
                        mol_type = protein
                        organism = synthetic construct
SEQUENCE: 132
KSSQSLLHSD GKTYLN                                                       16

SEQ ID NO: 133          moltype = AA  length = 7
FEATURE                 Location/Qualifiers
REGION                  1..7
                        note = H2M287L-CDR2
source                  1..7
                        mol_type = protein
                        organism = synthetic construct
SEQUENCE: 133
LVSKLDS                                                                  7

SEQ ID NO: 134          moltype = AA  length = 8
FEATURE                 Location/Qualifiers
REGION                  1..8
                        note = H2M287L-CDR3
source                  1..8
                        mol_type = protein
                        organism = synthetic construct
SEQUENCE: 134
WQGTHFPT                                                                 8

SEQ ID NO: 135          moltype = AA  length = 5
FEATURE                 Location/Qualifiers
REGION                  1..5
                        note = H2M288H-CDR1
source                  1..5
                        mol_type = protein
                        organism = synthetic construct
SEQUENCE: 135
RYSLS                                                                    5

SEQ ID NO: 136          moltype = AA  length = 17
FEATURE                 Location/Qualifiers
REGION                  1..17
                        note = H2M288H-CDR2
source                  1..17
                        mol_type = protein
```

```
                           -continued
                    organism = synthetic construct
SEQUENCE: 136
VISSGGRYTF YPDGVKG                                                17

SEQ ID NO: 137      moltype = AA  length = 5
FEATURE             Location/Qualifiers
REGION              1..5
                    note = H2M288H-CDR3
source              1..5
                    mol_type = protein
                    organism = synthetic construct
SEQUENCE: 137
EAGDY                                                              5

SEQ ID NO: 138      moltype = AA  length = 16
FEATURE             Location/Qualifiers
REGION              1..16
                    note = H2M288L-CDR1
source              1..16
                    mol_type = protein
                    organism = synthetic construct
SEQUENCE: 138
KSSQSLLHSD GKTYLN                                                 16

SEQ ID NO: 139      moltype = AA  length = 7
FEATURE             Location/Qualifiers
REGION              1..7
                    note = H2M288L-CDR2
source              1..7
                    mol_type = protein
                    organism = synthetic construct
SEQUENCE: 139
LVSKLDS                                                            7

SEQ ID NO: 140      moltype = AA  length = 8
FEATURE             Location/Qualifiers
REGION              1..8
                    note = H2M288L-CDR3
source              1..8
                    mol_type = protein
                    organism = synthetic construct
SEQUENCE: 140
WQGTHFPT                                                           8

SEQ ID NO: 141      moltype = AA  length = 5
FEATURE             Location/Qualifiers
REGION              1..5
                    note = H2M289H-CDR1
source              1..5
                    mol_type = protein
                    organism = synthetic construct
SEQUENCE: 141
GFFMN                                                              5

SEQ ID NO: 142      moltype = AA  length = 17
FEATURE             Location/Qualifiers
REGION              1..17
                    note = H2M289H-CDR2
source              1..17
                    mol_type = protein
                    organism = synthetic construct
SEQUENCE: 142
RINPYNGDTF YNQKFND                                                17

SEQ ID NO: 143      moltype = AA  length = 12
FEATURE             Location/Qualifiers
REGION              1..12
                    note = H2M289H-CDR3
source              1..12
                    mol_type = protein
                    organism = synthetic construct
SEQUENCE: 143
ISGNYRGYAM DN                                                     12

SEQ ID NO: 144      moltype = AA  length = 16
FEATURE             Location/Qualifiers
REGION              1..16
                    note = H2M289L-CDR1
source              1..16
```

```
                            -continued mol_type = protein
                            organism = synthetic construct
SEQUENCE: 144
RSSQTILHTN GNTYLE                                                 16

SEQ ID NO: 145              moltype = AA  length = 7
FEATURE                     Location/Qualifiers
REGION                      1..7
                            note = H2M289L-CDR2
source                      1..7
                            mol_type = protein
                            organism = synthetic construct
SEQUENCE: 145
KVSNRFS                                                            7

SEQ ID NO: 146              moltype = AA  length = 9
FEATURE                     Location/Qualifiers
REGION                      1..9
                            note = H2M289L-CDR3
source                      1..9
                            mol_type = protein
                            organism = synthetic construct
SEQUENCE: 146
FQGSRVPPT                                                          9

SEQ ID NO: 147              moltype = AA  length = 5
FEATURE                     Location/Qualifiers
REGION                      1..5
                            note = H2M290H-CDR1
source                      1..5
                            mol_type = protein
                            organism = synthetic construct
SEQUENCE: 147
SYSMS                                                              5

SEQ ID NO: 148              moltype = AA  length = 17
FEATURE                     Location/Qualifiers
REGION                      1..17
                            note = H2M290H-CDR2
source                      1..17
                            mol_type = protein
                            organism = synthetic construct
SEQUENCE: 148
IISSGGSYIF YPDSVKG                                                17

SEQ ID NO: 149              moltype = AA  length = 5
FEATURE                     Location/Qualifiers
REGION                      1..5
                            note = H2M290H-CDR3
source                      1..5
                            mol_type = protein
                            organism = synthetic construct
SEQUENCE: 149
EAGDY                                                              5

SEQ ID NO: 150              moltype = AA  length = 16
FEATURE                     Location/Qualifiers
REGION                      1..16
                            note = H2M290L-CDR1
source                      1..16
                            mol_type = protein
                            organism = synthetic construct
SEQUENCE: 150
KSSQSLLHSD GKTYLN                                                 16

SEQ ID NO: 151              moltype = AA  length = 7
FEATURE                     Location/Qualifiers
REGION                      1..7
                            note = H2M290L-CDR2
source                      1..7
                            mol_type = protein
                            organism = synthetic construct
SEQUENCE: 151
LVSNLDS                                                            7

SEQ ID NO: 152              moltype = AA  length = 8
FEATURE                     Location/Qualifiers
REGION                      1..8
                            note = H2M290L-CDR3
```

|                |                                                                                      |    |
|----------------|--------------------------------------------------------------------------------------|----|
| source         | 1..8<br>mol_type = protein<br>organism = synthetic construct                         |    |
| SEQUENCE: 152<br>WQGTHFPT |                                                                           | 8  |
| SEQ ID NO: 153<br>FEATURE<br>REGION<br><br>source | moltype = AA length = 5<br>Location/Qualifiers<br>1..5<br>note = H2M291H-CDR1<br>1..5<br>mol_type = protein<br>organism = synthetic construct |    |
| SEQUENCE: 153<br>GYTMN |                                                                              | 5  |
| SEQ ID NO: 154<br>FEATURE<br>REGION<br><br>source | moltype = AA length = 17<br>Location/Qualifiers<br>1..17<br>note = H2M291H-CDR2<br>1..17<br>mol_type = protein<br>organism = synthetic construct |    |
| SEQUENCE: 154<br>LINPYNGNTR YNQKFQD |                                                                 | 17 |
| SEQ ID NO: 155<br>FEATURE<br>REGION<br><br>source | moltype = AA length = 5<br>Location/Qualifiers<br>1..5<br>note = H2M291H-CDR3<br>1..5<br>mol_type = protein<br>organism = synthetic construct |    |
| SEQUENCE: 155<br>EPSDY |                                                                              | 5  |
| SEQ ID NO: 156<br>FEATURE<br>REGION<br><br>source | moltype = AA length = 16<br>Location/Qualifiers<br>1..16<br>note = H2M291L-CDR1<br>1..16<br>mol_type = protein<br>organism = synthetic construct |    |
| SEQUENCE: 156<br>RSSQSLVHIN GNTYLH |                                                                  | 16 |
| SEQ ID NO: 157<br>FEATURE<br>REGION<br><br>source | moltype = AA length = 7<br>Location/Qualifiers<br>1..7<br>note = H2M291L-CDR2<br>1..7<br>mol_type = protein<br>organism = synthetic construct |    |
| SEQUENCE: 157<br>KVSKRFS |                                                                            | 7  |
| SEQ ID NO: 158<br>FEATURE<br>REGION<br><br>source | moltype = AA length = 9<br>Location/Qualifiers<br>1..9<br>note = H2M291L-CDR3<br>1..9<br>mol_type = protein<br>organism = synthetic construct |    |
| SEQUENCE: 158<br>SQSTHVPPT |                                                                          | 9  |
| SEQ ID NO: 159<br>FEATURE<br>REGION<br><br>source | moltype = AA length = 5<br>Location/Qualifiers<br>1..5<br>note = H2M292H-CDR1<br>1..5<br>mol_type = protein<br>organism = synthetic construct |    |
| SEQUENCE: 159<br>GYTMN |                                                                              | 5  |
| SEQ ID NO: 160<br>FEATURE<br>REGION | moltype = AA length = 17<br>Location/Qualifiers<br>1..17              |    |

```
                        note = H2M292H-CDR2
source                  1..17
                        mol_type = protein
                        organism = synthetic construct
SEQUENCE: 160
LINPSNGGTR YNQKFKD                                                    17

SEQ ID NO: 161          moltype = AA  length = 5
FEATURE                 Location/Qualifiers
REGION                  1..5
                        note = H2M292H-CDR3
source                  1..5
                        mol_type = protein
                        organism = synthetic construct
SEQUENCE: 161
EPSDY                                                                  5

SEQ ID NO: 162          moltype = AA  length = 16
FEATURE                 Location/Qualifiers
REGION                  1..16
                        note = H2M292L-CDR1
source                  1..16
                        mol_type = protein
                        organism = synthetic construct
SEQUENCE: 162
RSSQSLVHSN GNTYLH                                                     16

SEQ ID NO: 163          moltype = AA  length = 7
FEATURE                 Location/Qualifiers
REGION                  1..7
                        note = H2M292L-CDR2
source                  1..7
                        mol_type = protein
                        organism = synthetic construct
SEQUENCE: 163
KVSNRFS                                                                7

SEQ ID NO: 164          moltype = AA  length = 9
FEATURE                 Location/Qualifiers
REGION                  1..9
                        note = H2M292L-CDR3
source                  1..9
                        mol_type = protein
                        organism = synthetic construct
SEQUENCE: 164
SQSTHVPPT                                                              9

SEQ ID NO: 165          moltype = AA  length = 5
FEATURE                 Location/Qualifiers
REGION                  1..5
                        note = H2M293H-CDR1
source                  1..5
                        mol_type = protein
                        organism = synthetic construct
SEQUENCE: 165
NYGIF                                                                  5

SEQ ID NO: 166          moltype = AA  length = 17
FEATURE                 Location/Qualifiers
REGION                  1..17
                        note = H2M293H-CDR2
source                  1..17
                        mol_type = protein
                        organism = synthetic construct
SEQUENCE: 166
TVKSNGGSTY YPDSVKG                                                    17

SEQ ID NO: 167          moltype = AA  length = 5
FEATURE                 Location/Qualifiers
REGION                  1..5
                        note = H2M293H-CDR3
source                  1..5
                        mol_type = protein
                        organism = synthetic construct
SEQUENCE: 167
EGGDY                                                                  5

SEQ ID NO: 168          moltype = AA  length = 11
FEATURE                 Location/Qualifiers
```

```
REGION                    1..11
                          note = H2M293L-CDR1
source                    1..11
                          mol_type = protein
                          organism = synthetic construct
SEQUENCE: 168
KASQDVGTAV A                                                                    11

SEQ ID NO: 169            moltype = AA  length = 7
FEATURE                   Location/Qualifiers
REGION                    1..7
                          note = H2M293L-CDR2
source                    1..7
                          mol_type = protein
                          organism = synthetic construct
SEQUENCE: 169
WTSTRHI                                                                          7

SEQ ID NO: 170            moltype = AA  length = 9
FEATURE                   Location/Qualifiers
REGION                    1..9
                          note = H2M293L-CDR3
source                    1..9
                          mol_type = protein
                          organism = synthetic construct
SEQUENCE: 170
QQYSKNPLT                                                                        9

SEQ ID NO: 171            moltype = AA  length = 5
FEATURE                   Location/Qualifiers
REGION                    1..5
                          note = H2M294H-CDR1
source                    1..5
                          mol_type = protein
                          organism = synthetic construct
SEQUENCE: 171
SYGMS                                                                            5

SEQ ID NO: 172            moltype = AA  length = 17
FEATURE                   Location/Qualifiers
REGION                    1..17
                          note = H2M294H-CDR2
source                    1..17
                          mol_type = protein
                          organism = synthetic construct
SEQUENCE: 172
TINSNGGGTY YPDSVKG                                                              17

SEQ ID NO: 173            moltype = AA  length = 7
FEATURE                   Location/Qualifiers
REGION                    1..7
                          note = H2M294H-CDR3
source                    1..7
                          mol_type = protein
                          organism = synthetic construct
SEQUENCE: 173
PGSWFPY                                                                          7

SEQ ID NO: 174            moltype = AA  length = 16
FEATURE                   Location/Qualifiers
REGION                    1..16
                          note = H2M294L-CDR1
source                    1..16
                          mol_type = protein
                          organism = synthetic construct
SEQUENCE: 174
KSSQSLLDSD GKTYLH                                                               16

SEQ ID NO: 175            moltype = AA  length = 7
FEATURE                   Location/Qualifiers
REGION                    1..7
                          note = H2M294L-CDR2
source                    1..7
                          mol_type = protein
                          organism = synthetic construct
SEQUENCE: 175
LVSKLDS                                                                          7

SEQ ID NO: 176            moltype = AA  length = 9
```

-continued

```
FEATURE             Location/Qualifiers
REGION              1..9
                    note = H2M294L-CDR3
source              1..9
                    mol_type = protein
                    organism = synthetic construct
SEQUENCE: 176
WQGTHFPQT                                                              9

SEQ ID NO: 177      moltype = AA  length = 5
FEATURE             Location/Qualifiers
REGION              1..5
                    note = H2M295H-CDR1
source              1..5
                    mol_type = protein
                    organism = synthetic construct
SEQUENCE: 177
GYTMN                                                                  5

SEQ ID NO: 178      moltype = AA  length = 17
FEATURE             Location/Qualifiers
REGION              1..17
                    note = H2M295H-CDR2
source              1..17
                    mol_type = protein
                    organism = synthetic construct
SEQUENCE: 178
LINPYNGGTR YNQKFKG                                                    17

SEQ ID NO: 179      moltype = AA  length = 5
FEATURE             Location/Qualifiers
REGION              1..5
                    note = H2M295H-CDR3
source              1..5
                    mol_type = protein
                    organism = synthetic construct
SEQUENCE: 179
EPSDY                                                                  5

SEQ ID NO: 180      moltype = AA  length = 16
FEATURE             Location/Qualifiers
REGION              1..16
                    note = H2M295L-CDR1
source              1..16
                    mol_type = protein
                    organism = synthetic construct
SEQUENCE: 180
RSSQSLVHSN GNTYLH                                                     16

SEQ ID NO: 181      moltype = AA  length = 7
FEATURE             Location/Qualifiers
REGION              1..7
                    note = H2M295L-CDR2
source              1..7
                    mol_type = protein
                    organism = synthetic construct
SEQUENCE: 181
KVSKRFS                                                                7

SEQ ID NO: 182      moltype = AA  length = 9
FEATURE             Location/Qualifiers
REGION              1..9
                    note = H2M295L-CDR3
source              1..9
                    mol_type = protein
                    organism = synthetic construct
SEQUENCE: 182
SQSSHVPPT                                                              9

SEQ ID NO: 183      moltype = AA  length = 7
FEATURE             Location/Qualifiers
REGION              1..7
                    note = H2M296H-CDR1
source              1..7
                    mol_type = protein
                    organism = synthetic construct
SEQUENCE: 183
TSGMGVG                                                                7
```

-continued

| | | |
|---|---|---|
| SEQ ID NO: 184 | moltype = AA  length = 16 | |
| FEATURE | Location/Qualifiers | |
| REGION | 1..16 | |
| | note = H2M296H-CDR2 | |
| source | 1..16 | |
| | mol_type = protein | |
| | organism = synthetic construct | |
| SEQUENCE: 184 | | |
| HIWWDDDKRY NPALKS | | 16 |
| | | |
| SEQ ID NO: 185 | moltype = AA  length = 9 | |
| FEATURE | Location/Qualifiers | |
| REGION | 1..9 | |
| | note = H2M296H-CDR3 | |
| source | 1..9 | |
| | mol_type = protein | |
| | organism = synthetic construct | |
| SEQUENCE: 185 | | |
| IEGQRGFAY | | 9 |
| | | |
| SEQ ID NO: 186 | moltype = AA  length = 17 | |
| FEATURE | Location/Qualifiers | |
| REGION | 1..17 | |
| | note = H2M296L-CDR1 | |
| source | 1..17 | |
| | mol_type = protein | |
| | organism = synthetic construct | |
| SEQUENCE: 186 | | |
| KSSQSLLYSR NQKNYLA | | 17 |
| | | |
| SEQ ID NO: 187 | moltype = AA  length = 7 | |
| FEATURE | Location/Qualifiers | |
| REGION | 1..7 | |
| | note = H2M296L-CDR2 | |
| source | 1..7 | |
| | mol_type = protein | |
| | organism = synthetic construct | |
| SEQUENCE: 187 | | |
| WASTRES | | 7 |
| | | |
| SEQ ID NO: 188 | moltype = AA  length = 9 | |
| FEATURE | Location/Qualifiers | |
| REGION | 1..9 | |
| | note = H2M296L-CDR3 | |
| source | 1..9 | |
| | mol_type = protein | |
| | organism = synthetic construct | |
| SEQUENCE: 188 | | |
| QQYYSQPYT | | 9 |
| | | |
| SEQ ID NO: 189 | moltype = AA  length = 5 | |
| FEATURE | Location/Qualifiers | |
| REGION | 1..5 | |
| | note = H2M297H-CDR1 | |
| source | 1..5 | |
| | mol_type = protein | |
| | organism = synthetic construct | |
| SEQUENCE: 189 | | |
| SYGIF | | 5 |
| | | |
| SEQ ID NO: 190 | moltype = AA  length = 17 | |
| FEATURE | Location/Qualifiers | |
| REGION | 1..17 | |
| | note = H2M297H-CDR2 | |
| source | 1..17 | |
| | mol_type = protein | |
| | organism = synthetic construct | |
| SEQUENCE: 190 | | |
| TIKSNGGRTY YPDSVKG | | 17 |
| | | |
| SEQ ID NO: 191 | moltype = AA  length = 5 | |
| FEATURE | Location/Qualifiers | |
| REGION | 1..5 | |
| | note = H2M297H-CDR3 | |
| source | 1..5 | |
| | mol_type = protein | |
| | organism = synthetic construct | |
| SEQUENCE: 191 | | |
| EGGDY | | 5 |

```
SEQ ID NO: 192         moltype = AA   length = 16
FEATURE                Location/Qualifiers
REGION                 1..16
                       note = H2M297L-CDR1
source                 1..16
                       mol_type = protein
                       organism = synthetic construct
SEQUENCE: 192
RSSQSVVHSN GNTYLE                                                          16

SEQ ID NO: 193         moltype = AA   length = 7
FEATURE                Location/Qualifiers
REGION                 1..7
                       note = H2M297L-CDR2
source                 1..7
                       mol_type = protein
                       organism = synthetic construct
SEQUENCE: 193
KVSNRFS                                                                     7

SEQ ID NO: 194         moltype = AA   length = 9
FEATURE                Location/Qualifiers
REGION                 1..9
                       note = H2M297L-CDR3
source                 1..9
                       mol_type = protein
                       organism = synthetic construct
SEQUENCE: 194
FQGSRVPPT                                                                   9

SEQ ID NO: 195         moltype = AA   length = 5
FEATURE                Location/Qualifiers
REGION                 1..5
                       note = H2M298H-CDR1
source                 1..5
                       mol_type = protein
                       organism = synthetic construct
SEQUENCE: 195
RYSMS                                                                       5

SEQ ID NO: 196         moltype = AA   length = 17
FEATURE                Location/Qualifiers
REGION                 1..17
                       note = H2M298H-CDR2
source                 1..17
                       mol_type = protein
                       organism = synthetic construct
SEQUENCE: 196
IISTGGSYMF YPDSAKG                                                         17

SEQ ID NO: 197         moltype = AA   length = 5
FEATURE                Location/Qualifiers
REGION                 1..5
                       note = H2M298H-CDR3
source                 1..5
                       mol_type = protein
                       organism = synthetic construct
SEQUENCE: 197
EAGDY                                                                       5

SEQ ID NO: 198         moltype = AA   length = 16
FEATURE                Location/Qualifiers
REGION                 1..16
                       note = H2M298L-CDR1
source                 1..16
                       mol_type = protein
                       organism = synthetic construct
SEQUENCE: 198
KSSQSLLHSD GKTYLN                                                          16

SEQ ID NO: 199         moltype = AA   length = 7
FEATURE                Location/Qualifiers
REGION                 1..7
                       note = H2M298L-CDR2
source                 1..7
                       mol_type = protein
                       organism = synthetic construct
SEQUENCE: 199
```

LVSKLDS                                                                           7

SEQ ID NO: 200          moltype = AA  length = 8
FEATURE                 Location/Qualifiers
REGION                  1..8
                        note = H2M298L-CDR3
source                  1..8
                        mol_type = protein
                        organism = synthetic construct
SEQUENCE: 200
WQGTHFPT                                                                          8

SEQ ID NO: 201          moltype = AA  length = 5
FEATURE                 Location/Qualifiers
REGION                  1..5
                        note = H2M299H-CDR1
source                  1..5
                        mol_type = protein
                        organism = synthetic construct
SEQUENCE: 201
IYGIF                                                                             5

SEQ ID NO: 202          moltype = AA  length = 17
FEATURE                 Location/Qualifiers
REGION                  1..17
                        note = H2M299H-CDR2
source                  1..17
                        mol_type = protein
                        organism = synthetic construct
SEQUENCE: 202
TIHSNGGRIY YPDSVKG                                                               17

SEQ ID NO: 203          moltype = AA  length = 5
FEATURE                 Location/Qualifiers
REGION                  1..5
                        note = H2M299H-CDR3
source                  1..5
                        mol_type = protein
                        organism = synthetic construct
SEQUENCE: 203
EGGDY                                                                             5

SEQ ID NO: 204          moltype = AA  length = 11
FEATURE                 Location/Qualifiers
REGION                  1..11
                        note = H2M299L-CDR1
source                  1..11
                        mol_type = protein
                        organism = synthetic construct
SEQUENCE: 204
KASQDVGTAV A                                                                     11

SEQ ID NO: 205          moltype = AA  length = 7
FEATURE                 Location/Qualifiers
REGION                  1..7
                        note = H2M299L-CDR2
source                  1..7
                        mol_type = protein
                        organism = synthetic construct
SEQUENCE: 205
WASTRHT                                                                           7

SEQ ID NO: 206          moltype = AA  length = 9
FEATURE                 Location/Qualifiers
REGION                  1..9
                        note = H2M299L-CDR3
source                  1..9
                        mol_type = protein
                        organism = synthetic construct
SEQUENCE: 206
QQYRRYPLT                                                                         9

The invention claimed is:

1. An isolated antibody comprising:
a heavy chain variable region comprising
a heavy chain CDR1 comprising the amino acid sequence of SEQ ID NO: 24,
a heavy chain CDR2 comprising the amino acid sequence of SEQ ID NO: 25, and
a heavy chain CDR3 comprising the amino acid sequence of SEQ ID NO: 26, as well as a light chain variable region comprising
a light chain CDR1 comprising the amino acid sequence of SEQ ID NO: 27,
a light chain CDR2 comprising the amino acid sequence of SEQ ID NO: 28, and
a light chain CDR3 comprising the amino acid sequence of SEQ ID NO: 29;
or an antigen-binding fragment thereof selected from the group consisting of Fab, Fab', F(ab')$_2$, Fv, scFv (single chain Fv), diabody, scDb, tandem scFv, leucine zipper type, and sc(Fv)$_2$ (single chain (Fv)$_2$).

2. The antibody or antigen-binding fragment thereof according to claim 1, which is scFV.

* * * * *